(12) United States Patent
Schenk

(10) Patent No.: US 7,820,425 B2
(45) Date of Patent: *Oct. 26, 2010

(54) METHOD OF CRYOPRESERVING SELECTED SPERM CELLS

(75) Inventor: John L. Schenk, Fort Collins, CO (US)

(73) Assignee: XY, LLC, Navasota, TX (US)

(*) Notice: Subject to any disclaimer, the term of this patent is extended or adjusted under 35 U.S.C. 154(b) by 62 days.

This patent is subject to a terminal disclaimer.

(21) Appl. No.: 11/608,079

(22) Filed: Dec. 7, 2006

(65) Prior Publication Data

US 2007/0092860 A1    Apr. 26, 2007

Related U.S. Application Data

(60) Continuation of application No. 10/266,562, filed on Oct. 7, 2002, now abandoned, which is a continuation of application No. 09/577,246, filed on May 24, 2000, now abandoned, which is a division of application No. 09/478,299, filed on Jan. 5, 2000, now Pat. No. 7,208,265.

(60) Provisional application No. 60/167,423, filed on Nov. 24, 1999.

(51) Int. Cl.
    *C12N 9/24* (2006.01)

(52) U.S. Cl. .................. 435/200; 435/2; 435/325; 424/93.7

(58) Field of Classification Search .................. 435/200
    See application file for complete search history.

(56) References Cited

U.S. PATENT DOCUMENTS

| | | |
|---|---|---|
| 3,005,756 A | 10/1961 | VanDemark et al. |
| 3,499,435 A | 3/1970 | Rockwell et al. |
| 3,547,526 A | 12/1970 | Devereux |
| 3,644,128 A | 2/1972 | Lipner |
| 3,661,460 A | 5/1972 | Elking et al. |
| 3,687,806 A | 8/1972 | Van den Bovenkamp |
| 3,710,933 A | 1/1973 | Fulwyler et al. |
| 3,738,759 A | 6/1973 | Dittrich et al. |
| 3,756,459 A | 9/1973 | Bannister |
| 3,761,187 A | 9/1973 | Dittrich et al. |
| 3,761,941 A | 9/1973 | Robertson |
| 3,788,744 A | 1/1974 | Friedman et al. |
| 3,791,384 A | 2/1974 | Richter et al. |
| 3,791,517 A | 2/1974 | Friedman |
| 3,810,010 A | 5/1974 | Thom |
| 3,816,249 A | 6/1974 | Bhattacharya |
| 3,826,364 A | 7/1974 | Bonner et al. |
| 3,829,216 A | 8/1974 | Persidsky |
| 3,833,796 A | 9/1974 | Fetner et al. |
| 3,877,430 A | 4/1975 | Wieder |
| 3,893,766 A | 7/1975 | Hogg |
| 3,894,529 A | 7/1975 | Shrimpton |
| 3,906,929 A | 9/1975 | Augspurger |
| 3,909,744 A | 9/1975 | Wisner et al. |
| 3,916,143 A | 10/1975 | Farrell |
| 3,944,917 A | 3/1976 | Hogg et al. |
| 3,947,093 A | 3/1976 | Goshima et al. |
| 3,960,449 A | 6/1976 | Carleton et al. |
| 3,963,606 A | 6/1976 | Hogg |
| 3,973,003 A | 8/1976 | Colas |
| 3,973,196 A | 8/1976 | Hogg |
| RE29,141 E | 2/1977 | Hogg |
| 4,006,360 A | 2/1977 | Mueller |
| 4,007,087 A | 2/1977 | Ericsson |
| 4,009,260 A | 2/1977 | Ericsson |
| 4,014,611 A | 3/1977 | Simpson et al. |
| 4,056,324 A | 11/1977 | Gohde |
| 4,058,732 A | 11/1977 | Wieder |
| 4,067,965 A | 1/1978 | Bhattacharya |
| 4,070,617 A | 1/1978 | Kachel et al. |

(Continued)

FOREIGN PATENT DOCUMENTS

BR    9704313 (A)    4/1999

(Continued)

OTHER PUBLICATIONS

Australian Application No. 17552/01; Examiner's report dated Oct. 21, 2003.

(Continued)

*Primary Examiner*—Jon P Weber
*Assistant Examiner*—Tiffany M Gough
(74) *Attorney, Agent, or Firm*—Craig R. Miles; CR Miles, P.C.

(57) ABSTRACT

The present invention provides a method of cryopreserving sperm that have been selected for a specific characteristic. In a preferred embodiment, the method is employed to freeze sex-selected sperm. Although the cryopreservation method of the invention can be used to freeze sperm selected by any number of selection methods, selection using flow cytometry is preferred. The present invention also provides a frozen sperm sample that has been selected for a particular characteristic, such as sex-type. In preferred embodiments, the frozen sperm sample includes mammalian sperm, such as, for example, human, bovine, equine, porcine, ovine, elk, or bison sperm. The frozen selected sperm sample can be used in a variety of applications. In particular, the sample can be thawed and used for fertilization. Accordingly, the invention also includes a method of using the frozen selected sperm sample for artificial insemination or in vitro fertilization.

34 Claims, No Drawings

U.S. PATENT DOCUMENTS

| | | |
|---|---|---|
| 4,083,957 A | 4/1978 | Lang |
| 4,085,205 A | 4/1978 | Hancock |
| 4,092,229 A | 5/1978 | Bhattacharya |
| 4,110,604 A | 8/1978 | Haynes et al. |
| 4,148,718 A | 4/1979 | Fulwyler |
| 4,155,831 A | 5/1979 | Bhattacharya |
| 4,162,282 A | 7/1979 | Fulwyler et al. |
| 4,175,662 A | 11/1979 | Zold |
| 4,178,936 A | 12/1979 | Newcomb |
| 4,179,218 A | 12/1979 | Erdmann et al. |
| 4,189,236 A | 2/1980 | Hogg et al. |
| 4,191,749 A | 3/1980 | Bryant |
| 4,200,802 A | 4/1980 | Salzman et al. |
| 4,225,229 A | 9/1980 | Gohde |
| 4,225,405 A | 9/1980 | Lawson |
| 4,230,558 A | 10/1980 | Fulwyler |
| 4,255,021 A | 3/1981 | Brunsden |
| 4,263,508 A | 4/1981 | Leary et al. |
| 4,267,268 A | 5/1981 | Nelson, Jr. |
| 4,274,408 A | 6/1981 | Nimrod |
| 4,274,740 A | 6/1981 | Eidenschink et al. |
| 4,276,139 A | 6/1981 | Lawson |
| 4,302,166 A | 11/1981 | Fulwyler et al. |
| 4,317,520 A | 3/1982 | Lombardo et al. |
| 4,318,480 A | 3/1982 | Lombardo et al. |
| 4,318,481 A | 3/1982 | Lombardo et al. |
| 4,318,482 A | 3/1982 | Barry et al. |
| 4,325,483 A | 4/1982 | Lombardo et al. |
| 4,327,177 A | 4/1982 | Shrimpton |
| 4,339,434 A | 7/1982 | Ericsson |
| 4,341,471 A | 7/1982 | Hogg et al. |
| 4,348,107 A | 9/1982 | Leif |
| 4,350,410 A | 9/1982 | Minott |
| 4,352,558 A | 10/1982 | Eisert |
| 4,361,400 A | 11/1982 | Gray et al. |
| 4,362,246 A | 12/1982 | Adair |
| 4,367,043 A | 1/1983 | Sweet et al. |
| 4,395,397 A | 7/1983 | Shapiro |
| 4,395,676 A | 7/1983 | Hollinger et al. |
| 4,400,764 A | 8/1983 | Kenyon |
| 4,408,877 A | 10/1983 | Lindmo et al. |
| 4,422,761 A | 12/1983 | Frommer |
| 4,448,767 A | 5/1984 | Bryant |
| 4,474,875 A | 10/1984 | Shrimpton |
| 4,487,320 A | 12/1984 | Auer |
| 4,492,436 A | 1/1985 | Bergmann |
| 4,498,766 A | 2/1985 | Unterleitner |
| 4,501,366 A | 2/1985 | Thompson |
| 4,511,661 A | 4/1985 | Goldberg |
| 4,515,274 A | 5/1985 | Hollinger et al. |
| 4,523,809 A | 6/1985 | Taboada et al. |
| 4,538,733 A | 9/1985 | Hoffman |
| 4,545,677 A | 10/1985 | Chupp |
| 4,559,309 A | 12/1985 | Evenson |
| 4,573,796 A | 3/1986 | Martin |
| 4,585,736 A | 4/1986 | Dolbeare et al. |
| 4,598,408 A | 7/1986 | O'Keefe |
| 4,600,302 A | 7/1986 | Sage, Jr. |
| 4,605,558 A | 8/1986 | Shrimpton |
| 4,609,286 A | 9/1986 | Sage, Jr. |
| 4,629,687 A | 12/1986 | Schindler et al. |
| 4,631,483 A | 12/1986 | Proni et al. |
| 4,637,691 A | 1/1987 | Uehara et al. |
| RE32,350 E | 2/1987 | Bhattacharya |
| 4,654,025 A | 3/1987 | Cassou et al. |
| 4,659,185 A | 4/1987 | Aughton |
| 4,660,971 A | 4/1987 | Sage et al. |
| 4,661,913 A | 4/1987 | Wu et al. |
| 4,662,742 A | 5/1987 | Chupp |
| 4,673,288 A | 6/1987 | Thomas et al. |
| 4,673,289 A | 6/1987 | Gaucher |
| 4,680,258 A | 7/1987 | Hammerling et al. |
| 4,683,195 A | 7/1987 | Mullis et al. |
| 4,683,202 A | 7/1987 | Mullis |
| 4,691,829 A | 9/1987 | Auer |
| 4,698,142 A | 10/1987 | Muroi et al. |
| 4,702,598 A | 10/1987 | Böhmer |
| 4,704,891 A | 11/1987 | Recktenwald et al. |
| 4,710,635 A | 12/1987 | Chupp |
| 4,714,680 A | 12/1987 | Civin |
| 4,737,025 A | 4/1988 | Steen |
| 4,744,090 A | 5/1988 | Freiberg |
| 4,749,458 A | 6/1988 | Muroi et al. |
| 4,752,131 A | 6/1988 | Eisenlauer et al. |
| 4,756,427 A | 7/1988 | Gohde et al. |
| 4,758,729 A | 7/1988 | Monnin |
| 4,764,013 A | 8/1988 | Johnston |
| 4,765,737 A | 8/1988 | Harris et al. |
| 4,770,992 A | 9/1988 | den Engh et al. |
| 4,778,593 A | 10/1988 | Yamashita et al. |
| 4,780,406 A | 10/1988 | Dolbeare et al. |
| 4,780,451 A | 10/1988 | Donaldson |
| 4,786,165 A | 11/1988 | Yamamoto et al. |
| 4,790,653 A | 12/1988 | North, Jr. |
| 4,794,086 A | 12/1988 | Kasper et al. |
| 4,796,788 A | 1/1989 | Bond |
| 4,818,103 A | 4/1989 | Thomas et al. |
| 4,831,385 A | 5/1989 | Archer et al. |
| 4,836,038 A | 6/1989 | Baldwyn |
| 4,845,025 A | 7/1989 | Lary et al. |
| 4,846,785 A | 7/1989 | Cassou |
| 4,867,908 A | 9/1989 | Recktenwald et al. |
| 4,871,249 A | 10/1989 | Watson |
| 4,876,458 A | 10/1989 | Takeda et al. |
| 4,877,965 A | 10/1989 | Dandliker et al. |
| 4,887,721 A | 12/1989 | Martin et al. |
| 4,915,501 A | 4/1990 | Steen |
| 4,936,465 A | 6/1990 | Zold |
| 4,942,305 A | 7/1990 | Sommer |
| 4,954,715 A | 9/1990 | Zold |
| 4,957,363 A | 9/1990 | Takeda et al. |
| 4,959,354 A | 9/1990 | Barbetti |
| 4,965,204 A | 10/1990 | Civin |
| 4,979,093 A | 12/1990 | Laine et al. |
| 4,980,277 A | 12/1990 | Junilla |
| 4,981,580 A | 1/1991 | Auer |
| 4,983,038 A | 1/1991 | Ohki et al. |
| 4,987,539 A | 1/1991 | Moore et al. |
| 4,988,619 A | 1/1991 | Pinkel |
| 4,989,977 A | 2/1991 | North, Jr. |
| 4,999,283 A | 3/1991 | Zavos et al. |
| 5,005,981 A | 4/1991 | Schulte et al. |
| 5,007,732 A | 4/1991 | Ohki et al. |
| 5,017,497 A | 5/1991 | De Grooth |
| 5,021,244 A | 6/1991 | Spaulding |
| 5,030,002 A | 7/1991 | North, Jr. |
| 5,034,613 A | 7/1991 | Denk et al. |
| 5,040,890 A | 8/1991 | North, Jr. |
| 5,043,591 A | 8/1991 | Ludlow et al. |
| 5,055,393 A | 10/1991 | Kwoh et al. |
| 5,057,413 A | 10/1991 | Terstappen et al. |
| 5,072,382 A | 12/1991 | Kamentsky |
| 5,076,472 A | 12/1991 | Gross et al. |
| 5,079,959 A | 1/1992 | Miyake et al. |
| 5,084,004 A | 1/1992 | Ranoux |
| 5,087,295 A | 2/1992 | Gross et al. |
| 5,088,816 A | 2/1992 | Tomioka et al. |
| 5,089,714 A | 2/1992 | Ludlow et al. |
| 5,098,657 A | 3/1992 | Blackford et al. |
| 5,101,978 A | 4/1992 | Marcus |
| 5,116,125 A | 5/1992 | Rigler |
| 5,127,729 A | 7/1992 | Oetliker et al. |
| 5,132,548 A | 7/1992 | Borden et al. |
| 5,135,759 A | 8/1992 | Johnson |

| | | | | | |
|---|---|---|---|---|---|
| 5,138,181 A | 8/1992 | Lefevre et al. | 5,584,982 A | 12/1996 | Dovichi et al. |
| 5,142,140 A | 8/1992 | Yamazaki et al. | 5,589,457 A | 12/1996 | Wiltbank |
| 5,142,462 A | 8/1992 | Kashima | 5,596,401 A | 1/1997 | Kusuzawa |
| 5,144,224 A | 9/1992 | Larsen | 5,601,234 A | 2/1997 | Larue |
| 5,150,313 A | 9/1992 | Van den Engh et al. | 5,601,235 A | 2/1997 | Booker et al. |
| 5,158,889 A | 10/1992 | Hirako et al. | 5,601,533 A | 2/1997 | Hancke et al. |
| 5,159,397 A | 10/1992 | Kosaka et al. | 5,602,039 A | 2/1997 | Van den Engh |
| 5,159,403 A | 10/1992 | Kosaka | 5,602,349 A | 2/1997 | Van den Engh |
| 5,162,306 A | 11/1992 | Donaldson | 5,608,519 A | 3/1997 | Grouley et al. |
| 5,167,926 A | 12/1992 | Kimura et al. | 5,620,842 A | 4/1997 | Davis et al. |
| 5,180,065 A | 1/1993 | Touge et al. | 5,622,820 A | 4/1997 | Rossi |
| 5,182,617 A | 1/1993 | Yoneyama et al. | 5,627,037 A | 5/1997 | Ward et al. |
| 5,195,979 A | 3/1993 | Schinkel et al. | 5,633,503 A | 5/1997 | Kosaka |
| 5,199,576 A | 4/1993 | Corio et al. | 5,641,457 A | 6/1997 | Vardanega |
| 5,204,884 A | 4/1993 | Leary et al. | 5,643,796 A | 7/1997 | Van den Engh et al. |
| 5,215,376 A | 6/1993 | Schulte et al. | 5,650,847 A | 7/1997 | Maltsev et al. |
| 5,219,729 A | 6/1993 | Hodgen | 5,658,751 A | 8/1997 | Yue et al. |
| 5,247,339 A | 9/1993 | Ogino | 5,660,997 A | 8/1997 | Spaulding |
| 5,259,593 A | 11/1993 | Orme et al. | 5,663,048 A | 9/1997 | Winkfein et al. |
| 5,260,764 A | 11/1993 | Fukuda et al. | 5,665,315 A | 9/1997 | Robert et al. |
| 5,274,240 A | 12/1993 | Mathies et al. | 5,672,880 A | 9/1997 | Kain |
| 5,275,787 A | 1/1994 | Yuguchi et al. | 5,674,743 A | 10/1997 | Ulmer |
| 5,298,967 A | 3/1994 | Wells | 5,675,401 A | 10/1997 | Wangler et al. |
| 5,315,122 A | 5/1994 | Pinsky et al. | 5,682,038 A | 10/1997 | Hoffman |
| 5,316,540 A | 5/1994 | McMannis et al. | 5,684,575 A | 11/1997 | Steen |
| 5,317,162 A | 5/1994 | Pinsky et al. | 5,687,727 A | 11/1997 | Kraus et al. |
| 5,336,217 A | 8/1994 | Buys et al. | 5,690,815 A | 11/1997 | Krasnoff et al. |
| 5,346,990 A | 9/1994 | Spaulding | 5,690,895 A | 11/1997 | Matsumoto et al. |
| RE34,782 E | 11/1994 | Dandliker et al. | 5,691,133 A | 11/1997 | Critser et al. |
| 5,359,907 A | 11/1994 | Baker et al. | 5,693,534 A | 12/1997 | Alak et al. |
| 5,366,888 A | 11/1994 | Fry et al. | 5,696,157 A | 12/1997 | Wang et al. |
| 5,367,474 A | 11/1994 | Auer et al. | 5,700,692 A | 12/1997 | Sweet |
| 5,370,842 A | 12/1994 | Miyazaki et al. | 5,701,012 A | 12/1997 | Ho |
| 5,371,585 A | 12/1994 | Morgan et al. | 5,707,808 A | 1/1998 | Roslaniec et al. |
| 5,395,588 A | 3/1995 | North, Jr. et al. | 5,708,868 A | 1/1998 | Ishikawa |
| 5,400,179 A | 3/1995 | Ito | 5,712,807 A | 1/1998 | Bangham |
| 5,412,466 A | 5/1995 | Ogino | 5,719,666 A | 2/1998 | Fukuda et al. |
| 5,437,987 A | 8/1995 | Ten et al. | 5,719,667 A | 2/1998 | Miers |
| 5,439,362 A | 8/1995 | Spaulding | 5,726,009 A | 3/1998 | Connors et al. |
| 5,444,527 A | 8/1995 | Kosaka | 5,726,364 A | 3/1998 | Van den Engh |
| 5,447,841 A | 9/1995 | Grey et al. | 5,726,751 A | 3/1998 | Altendorf et al. |
| 5,447,842 A | 9/1995 | Simons | 5,730,941 A | 3/1998 | Lefevre et al. |
| 5,452,054 A | 9/1995 | Dewa et al. | 5,736,330 A | 4/1998 | Fulton |
| 5,457,526 A | 10/1995 | Kosaka | 5,739,902 A | 4/1998 | Gjelsnes et al. |
| 5,461,145 A | 10/1995 | Kudo et al. | 5,745,308 A | 4/1998 | Spangenberg |
| 5,464,581 A | 11/1995 | Van den Engh | 5,747,349 A | 5/1998 | den Engh et al. |
| 5,466,572 A | 11/1995 | Sasaki et al. | 5,759,767 A | 6/1998 | Lakowicz et al. |
| 5,467,189 A | 11/1995 | Kreikebaum et al. | 5,777,732 A | 7/1998 | Hanninen et al. |
| 5,469,375 A | 11/1995 | Kosaka | 5,780,230 A | 7/1998 | Li et al. |
| 5,471,294 A | 11/1995 | Ogino | 5,786,560 A | 7/1998 | Tatah et al. |
| 5,471,299 A | 11/1995 | Kaye et al. | 5,790,692 A | 8/1998 | Price et al. |
| 5,475,487 A | 12/1995 | Mariella, Jr. et al. | 5,793,485 A | 8/1998 | Gourley |
| 5,480,774 A | 1/1996 | Hew et al. | 5,796,112 A | 8/1998 | Ichie |
| 5,480,775 A | 1/1996 | Ito et al. | 5,798,276 A | 8/1998 | Haugland et al. |
| 5,483,469 A | 1/1996 | Van den Engh et al. | 5,799,830 A | 9/1998 | Carroll et al. |
| 5,488,469 A | 1/1996 | Yamamoto et al. | 5,804,436 A | 9/1998 | Okun et al. |
| 5,492,534 A | 2/1996 | Atheyde | 5,815,262 A | 9/1998 | Schrof et al. |
| 5,494,795 A | 2/1996 | Guerry et al. | 5,819,948 A | 10/1998 | Van den Engh |
| 5,495,719 A | 3/1996 | Gray, Jr. | 5,824,269 A | 10/1998 | Kosaka et al. |
| 5,496,272 A | 3/1996 | Chung et al. | 5,831,723 A | 11/1998 | Kubota et al. |
| 5,503,994 A | 4/1996 | Shear et al. | 5,835,262 A | 11/1998 | Iketaki et al. |
| 5,514,537 A | 5/1996 | Chandler | 5,840,504 A | 11/1998 | Blecher |
| 5,523,573 A | 6/1996 | Hanninen et al. | 5,844,685 A | 12/1998 | Gontin |
| 5,532,155 A | 7/1996 | Ranoux | 5,846,737 A | 12/1998 | Kang |
| 5,547,849 A | 8/1996 | Baer et al. | 5,866,344 A | 2/1999 | Georgiou |
| 5,548,395 A | 8/1996 | Kosaka | 5,868,767 A | 2/1999 | Farley et al. |
| 5,548,661 A | 8/1996 | Price et al. | 5,872,627 A | 2/1999 | Miers |
| 5,550,058 A | 8/1996 | Corio et al. | 5,873,254 A | 2/1999 | Arav |
| 5,556,764 A | 9/1996 | Sizto et al. | 5,874,266 A | 2/1999 | Paisson |
| 5,558,998 A | 9/1996 | Hammond et al. | 5,876,942 A | 3/1999 | Cheng et al. |
| 5,559,032 A | 9/1996 | Pomeroy et al. | 5,880,457 A | 3/1999 | Tomiyama et al. |
| 5,578,449 A | 11/1996 | Fr asch et al. | 5,880,474 A | 3/1999 | Norton et al. |
| 5,579,159 A | 11/1996 | Ito | 5,883,378 A | 3/1999 | Irish et al. |

| Patent | Kind | Date | Inventors |
|---|---|---|---|
| 5,888,730 | A | 3/1999 | Gray et al. |
| 5,891,734 | A | 4/1999 | Gill et al. |
| 5,893,843 | A | 4/1999 | Rodrigues |
| 5,895,764 | A | 4/1999 | Sklar et al. |
| 5,895,922 | A | 4/1999 | Ho |
| 5,899,848 | A | 5/1999 | Haubrich |
| 5,909,278 | A | 6/1999 | Deka et al. |
| 5,912,257 | A | 6/1999 | Prasad et al. |
| 5,916,144 | A | 6/1999 | Prather et al. |
| 5,916,449 | A | 6/1999 | Ellwart et al. |
| 5,917,733 | A | 6/1999 | Bangham |
| 5,919,360 | A | 7/1999 | Contaxis, III et al. |
| 5,919,621 | A | 7/1999 | Brown |
| 5,934,885 | A | 8/1999 | Farrell et al. |
| 5,962,238 | A | 10/1999 | Sizto et al. |
| 5,972,710 | A | 10/1999 | Weigl et al. |
| 5,973,842 | A | 10/1999 | Spangenberg |
| 5,985,216 | A | 11/1999 | Rens et al. |
| 5,985,538 | A | 11/1999 | Stachecju |
| 5,990,479 | A | 11/1999 | Weiss et al. |
| 5,991,028 | A | 11/1999 | Cabib et al. |
| 5,998,140 | A | 12/1999 | Dervan et al. |
| 5,998,212 | A | 12/1999 | Corio et al. |
| 6,002,471 | A | 12/1999 | Quake |
| 6,003,678 | A | 12/1999 | Van den Engh |
| 6,042,025 | A | 3/2000 | Crampton et al. |
| 6,042,249 | A | 3/2000 | Spangenberg |
| 6,050,935 | A | 4/2000 | Ranoux et al. |
| 6,071,689 | A | 6/2000 | Seidel et al. |
| 6,079,836 | A | 6/2000 | Burr et al. |
| 6,086,574 | A | 7/2000 | Carroll et al. |
| 6,087,352 | A | 7/2000 | Trout |
| 6,090,947 | A | 7/2000 | Dervan et al. |
| 6,097,485 | A | 8/2000 | Lievan |
| 6,111,398 | A | 8/2000 | Graham |
| 6,117,068 | A | 9/2000 | Gourley et al. |
| 6,119,465 | A | 9/2000 | Mullens et al. |
| 6,120,735 | A | 9/2000 | Zborowski et al. |
| 6,128,133 | A | 10/2000 | Bergmann |
| 6,130,034 | A | 10/2000 | Aitken |
| 6,132,961 | A | 10/2000 | Gray et al. |
| 6,133,044 | A | 10/2000 | Van den Engh |
| 6,133,995 | A | 10/2000 | Kubota |
| 6,139,800 | A | 10/2000 | Chandler |
| 6,140,121 | A | 10/2000 | Ellington et al. |
| 6,143,535 | A | 11/2000 | Paisson |
| 6,143,901 | A | 11/2000 | Dervan |
| 6,146,837 | A | 11/2000 | van de Winkel |
| 6,149,867 | A | 11/2000 | Seidel et al. |
| 6,153,373 | A | 11/2000 | Benjamin et al. |
| 6,154,276 | A | 11/2000 | Mariella, Jr. |
| 6,175,409 | B1 | 1/2001 | Nielsen et al. |
| 6,177,277 | B1 | 1/2001 | Soini |
| 6,193,647 | B1 | 2/2001 | Beebe et al. |
| 6,201,628 | B1 | 3/2001 | Basiji et al. |
| 6,207,392 | B1 | 3/2001 | Weiss et al. |
| 6,208,411 | B1 | 3/2001 | Vaez-Iravani |
| 6,211,477 | B1 | 4/2001 | Cardott et al. |
| 6,214,560 | B1 | 4/2001 | Yguerabide et al. |
| 6,221,654 | B1 | 4/2001 | Quake et al. |
| 6,221,671 | B1 | 4/2001 | Groner et al. |
| 6,238,920 | B1 | 5/2001 | Nagai et al. |
| 6,247,323 | B1 | 6/2001 | Maeda |
| 6,248,590 | B1 | 6/2001 | Malachowski |
| 6,256,096 | B1 | 7/2001 | Johnson |
| 6,263,745 | B1 | 7/2001 | Buchanan et al. |
| 6,283,920 | B1 | 9/2001 | Eberle et al. |
| 6,296,810 | B1 | 10/2001 | Ulmer |
| 6,309,815 | B1 | 10/2001 | Tash et al. |
| 6,316,234 | B1 | 11/2001 | Bova |
| 6,317,511 | B1 | 11/2001 | Horiuchi |
| 6,322,901 | B1 | 11/2001 | Bawendi et al. |
| 6,323,632 | B1 | 11/2001 | Husher et al. |
| 6,326,144 | B1 | 12/2001 | Bawendi et al. |
| 6,328,071 | B1 | 12/2001 | Austin |
| 6,329,158 | B1 | 12/2001 | Hoffman et al. |
| 6,332,540 | B1 | 12/2001 | Paul et al. |
| 6,357,307 | B2 | 3/2002 | Buchanan et al. |
| 6,368,786 | B1 | 4/2002 | Saint-Ramon et al. |
| 6,372,422 | B1 | 4/2002 | Seidel et al. |
| 6,372,506 | B1 | 4/2002 | Norton |
| 6,384,951 | B1 | 5/2002 | Basiji et al. |
| 6,395,305 | B1 | 5/2002 | Buhr et al. |
| 6,400,453 | B1 | 6/2002 | Hansen |
| 6,411,835 | B1 | 6/2002 | Modell et al. |
| 6,411,904 | B1 | 6/2002 | Chandler |
| 6,416,190 | B1 | 7/2002 | Grier et al. |
| 6,423,505 | B1 | 7/2002 | Davis |
| 6,423,551 | B1 | 7/2002 | Weiss et al. |
| 6,432,630 | B1 | 8/2002 | Blankenstein |
| 6,432,638 | B2 | 8/2002 | Dervan et al. |
| 6,452,372 | B1 | 9/2002 | Husher et al. |
| 6,454,945 | B1 | 9/2002 | Weigl et al. |
| 6,456,055 | B2 | 9/2002 | Shinabe et al. |
| 6,463,314 | B1 | 10/2002 | Haruna |
| 6,465,169 | B2 | 10/2002 | Walderich et al. |
| 6,473,176 | B2 | 10/2002 | Basiji et al. |
| 6,482,652 | B2 | 11/2002 | Furlong et al. |
| 6,489,092 | B1 | 12/2002 | Benjamin et al. |
| 6,495,333 | B1 | 12/2002 | Willmann et al. |
| 6,495,366 | B1 | 12/2002 | Briggs |
| 6,503,698 | B1 | 1/2003 | Dobrinsky et al. |
| 6,511,853 | B1 | 1/2003 | Kopf-Sill et al. |
| 6,514,722 | B2 | 2/2003 | Paisson et al. |
| 6,524,860 | B1 | 2/2003 | Seidel et al. |
| 6,528,802 | B1 | 3/2003 | Karsten et al. |
| 6,534,308 | B1 | 3/2003 | Palsson et al. |
| 6,537,829 | B1 | 3/2003 | Zarling et al. |
| 6,540,895 | B1 | 4/2003 | Spence et al. |
| 6,563,583 | B2 | 5/2003 | Ortyn et al. |
| 6,576,291 | B2 | 6/2003 | Bawendi et al. |
| 6,577,387 | B2 | 6/2003 | Ross, III et al. |
| 6,580,504 | B1 | 6/2003 | Ortyn et al. |
| 6,587,203 | B2 | 7/2003 | Colon |
| 6,589,792 | B1 | 7/2003 | Malachowski |
| 6,590,911 | B1 | 7/2003 | Spinelli et al. |
| 6,596,143 | B1 | 7/2003 | Wang et al. |
| 6,596,499 | B2 | 7/2003 | Jalink |
| 6,604,435 | B2 | 8/2003 | Buchanan et al. |
| 6,613,525 | B2 | 9/2003 | Nelson et al. |
| 6,617,107 | B1 | 9/2003 | Dean |
| 6,618,143 | B2 | 9/2003 | Roche et al. |
| 6,618,679 | B2 | 9/2003 | Loehrlein et al. |
| 6,641,708 | B1 | 11/2003 | Becker et al. |
| 6,642,018 | B1 | 11/2003 | Koller et al. |
| 6,658,357 | B2 | 12/2003 | Chandler |
| 6,664,550 | B2 | 12/2003 | Rader et al. |
| 6,667,830 | B1 | 12/2003 | Iketaki et al. |
| 6,671,044 | B2 | 12/2003 | Ortyn et al. |
| 6,673,095 | B2 | 1/2004 | Nordquist |
| 6,674,525 | B2 | 1/2004 | Bardell et al. |
| 6,698,627 | B2 | 3/2004 | Garcia et al. |
| 6,700,130 | B2 | 3/2004 | Fritz |
| 6,703,621 | B2 | 3/2004 | Wolleschensky |
| 6,706,163 | B2 | 3/2004 | Seul et al. |
| 6,707,555 | B1 | 3/2004 | Kusuzawa et al. |
| 6,713,019 | B2 | 3/2004 | Ozasa et al. |
| 6,729,369 | B2 | 5/2004 | Neas et al. |
| 6,746,873 | B1 | 6/2004 | Buchanan et al. |
| 6,752,298 | B2 | 6/2004 | Garcia et al. |
| 6,753,161 | B2 | 6/2004 | Koller et al. |
| 6,761,286 | B2 | 7/2004 | Py et al. |
| 6,761,288 | B2 | 7/2004 | Garcia |
| 6,767,706 | B2 | 7/2004 | Quake |
| 6,780,377 | B2 | 8/2004 | Hall et al. |
| 6,782,768 | B2 | 8/2004 | Buchanan et al. |

| | | |
|---|---|---|
| 6,789,706 B2 | 9/2004 | Abergel et al. |
| 6,789,750 B1 | 9/2004 | Miyasaka et al. |
| 6,789,759 B2 | 9/2004 | Heldt |
| 6,793,387 B1 | 9/2004 | Neas et al. |
| 6,813,017 B1 | 11/2004 | Hoffman et al. |
| 6,819,411 B1 | 11/2004 | Sharpe et al. |
| 6,849,394 B2 | 2/2005 | Rozenboom et al. |
| 6,849,423 B2 | 2/2005 | Mutz et al. |
| 6,861,265 B1 | 3/2005 | Van den Engh |
| 6,941,005 B2 | 9/2005 | Lary et al. |
| 7,015,310 B2 | 3/2006 | Remington et al. |
| 7,094,527 B2 | 8/2006 | Seidel et al. |
| 7,105,355 B2 | 9/2006 | Kurabayashi et al. |
| 7,195,920 B2 | 3/2007 | Seidel et al. |
| 7,208,265 B1 | 4/2007 | Schenk |
| 7,221,453 B2 | 5/2007 | Sharpe et al. |
| 2001/0006416 A1 | 7/2001 | Johnson |
| 2002/0047697 A1 | 4/2002 | Husher et al. |
| 2002/0058332 A1 | 5/2002 | Quake et al. |
| 2002/0064809 A1 | 5/2002 | Mutz et al. |
| 2002/0096123 A1 | 7/2002 | Whittier et al. |
| 2002/0113965 A1 | 8/2002 | Roche et al. |
| 2002/0115055 A1 | 8/2002 | Matta |
| 2002/0119558 A1 | 8/2002 | Seidel et al. |
| 2002/0131957 A1 | 9/2002 | Gavin |
| 2002/0141902 A1 | 10/2002 | Ozasa et al. |
| 2002/0171827 A1 | 11/2002 | Van den Engh |
| 2002/0182590 A1 | 12/2002 | Strange et al. |
| 2002/0186375 A1 | 12/2002 | Asbury et al. |
| 2002/0186874 A1 | 12/2002 | Price et al. |
| 2002/0198928 A1 | 12/2002 | Bukshpan et al. |
| 2003/0002027 A1 | 1/2003 | Fritz |
| 2003/0048433 A1 | 3/2003 | Desjonqueres |
| 2003/0059764 A1 | 3/2003 | Ravkin et al. |
| 2003/0059945 A1 | 3/2003 | Dzekunov et al. |
| 2003/0078703 A1 | 4/2003 | Potts |
| 2003/0096405 A1 | 5/2003 | Takayama et al. |
| 2003/0098421 A1 | 5/2003 | Ho |
| 2003/0113765 A1 | 6/2003 | Dempcy et al. |
| 2003/0119050 A1 | 6/2003 | Shai |
| 2003/0119206 A1 | 6/2003 | Shai |
| 2003/0129091 A1 | 7/2003 | Seidel et al. |
| 2003/0157475 A1 | 8/2003 | Schenk |
| 2003/0165812 A1 | 9/2003 | Takayama et al. |
| 2003/0175917 A1 | 9/2003 | Cumming |
| 2003/0175980 A1 | 9/2003 | Hayenga et al. |
| 2003/0190681 A1 | 10/2003 | Shai |
| 2003/0207461 A1 | 11/2003 | Bell et al. |
| 2003/0209059 A1 | 11/2003 | Kawano |
| 2004/0005582 A1 | 1/2004 | Shipwast |
| 2004/0031071 A1 | 2/2004 | Morris et al. |
| 2004/0034879 A1 | 2/2004 | Rothstein et al. |
| 2004/0049801 A1 | 3/2004 | Seidel |
| 2004/0053243 A1 | 3/2004 | Evans |
| 2004/0055030 A1 | 3/2004 | Maxwell et al. |
| 2004/0061070 A1 | 4/2004 | Hansen |
| 2004/0061853 A1 | 4/2004 | Blasenheim |
| 2004/0062685 A1 | 4/2004 | Norton et al. |
| 2004/0107150 A1 | 6/2004 | Neas et al. |
| 2004/0132001 A1 | 7/2004 | Seidel et al. |
| 2005/0003472 A1 | 1/2005 | Muhammad |
| 2005/0011582 A1 | 1/2005 | Haug |
| 2005/0064383 A1 | 3/2005 | Bashkin et al. |
| 2005/0112541 A1 | 5/2005 | Durack |
| 2005/0214733 A1 | 9/2005 | Graham |
| 2005/0244805 A1 | 11/2005 | Ludwig et al. |
| 2005/0282245 A1 | 12/2005 | Ludwig et al. |
| 2006/0118167 A1 | 6/2006 | Neas et al. |
| 2006/0147894 A1 | 7/2006 | Sowter |
| 2006/0263829 A1 | 11/2006 | Evans et al. |
| 2006/0281176 A1 | 12/2006 | Seidel et al. |
| 2007/0026378 A1 | 2/2007 | Schenk |
| 2007/0026379 A1 | 2/2007 | Seidel et al. |
| 2007/0042342 A1 | 2/2007 | Seidel et al. |
| 2007/0092860 A1 | 4/2007 | Schenk |
| 2007/0099171 A1 | 5/2007 | Schenk |
| 2007/0099260 A1 | 5/2007 | Seidel et al. |
| 2007/0117086 A1 | 5/2007 | Evans et al. |

FOREIGN PATENT DOCUMENTS

| | | |
|---|---|---|
| BR | 9704313 | 6/1999 |
| CA | 1029833 | 4/1978 |
| CA | 1 250 808 | 3/1989 |
| CA | 2113957 A1 | 1/1994 |
| CN | 03109426.0 | 12/2005 |
| CN | 100998524 | 7/2007 |
| DE | 69028526 | 2/1997 |
| DE | 195 49 015 C1 | 4/1997 |
| DE | 198 82 943.3 | 2/2001 |
| EP | 0025296 A2 | 3/1981 |
| EP | 0 046 345 A2 | 2/1982 |
| EP | 0 068 404 B1 | 1/1983 |
| EP | 0071538 A1 | 2/1983 |
| EP | 0 026 770 B1 | 3/1983 |
| EP | 0 029 662 B1 | 2/1984 |
| EP | 0 025 296 B1 | 5/1985 |
| EP | 0140616 | 5/1985 |
| EP | 0 158 147 A2 | 10/1985 |
| EP | 0160201 A2 | 11/1985 |
| EP | 0189702 A1 | 8/1986 |
| EP | 0 229 814 B1 | 7/1987 |
| EP | 0 246 604 A2 | 11/1987 |
| EP | 0288029 B1 | 4/1988 |
| EP | 0276166 A2 | 7/1988 |
| EP | 0 289 677 A2 | 11/1988 |
| EP | 0 316 173 A1 | 5/1989 |
| EP | 0 317 809 A2 | 5/1989 |
| EP | A-0 366794 | 5/1990 |
| EP | 0 409 293 A2 | 1/1991 |
| EP | 0461618 | 12/1991 |
| EP | 0 463 562 A1 | 1/1992 |
| EP | 0468100 A1 | 1/1992 |
| EP | 0 474 187 A2 | 3/1992 |
| EP | 0 316 172 B1 | 7/1992 |
| EP | 0 316 171 B1 | 9/1992 |
| EP | 0570102 A1 | 3/1993 |
| EP | 0538786 A | 4/1993 |
| EP | 0 279 000 B1 | 7/1993 |
| EP | 0 553 951 A1 | 8/1993 |
| EP | 0 288 029 B1 | 1/1994 |
| EP | 0 381 694 B1 | 6/1994 |
| EP | 0 361 504 B1 | 7/1994 |
| EP | 606847 A2 | 7/1994 |
| EP | 0 289 200 B2 | 8/1994 |
| EP | 0 555 212 B1 | 10/1994 |
| EP | 0 361 503 B1 | 11/1994 |
| EP | 0 696 731 A2 | 2/1996 |
| EP | 0 705 978 A2 | 4/1996 |
| EP | 0 711 991 A1 | 5/1996 |
| EP | 0 471 758 B1 | 9/1996 |
| EP | 0 736 765 A1 | 10/1996 |
| EP | 0 545 284 B1 | 2/1997 |
| EP | 0 360 487 B1 | 7/1997 |
| EP | 0 412 431 B1 | 10/1997 |
| EP | 0 526 131 B1 | 1/1998 |
| EP | A-0 478155 | 1/1998 |
| EP | 0 822 404 A3 | 2/1998 |
| EP | 0 822 401 A2 | 4/1998 |
| EP | 0781985 A3 | 7/1998 |
| EP | 0 556 748 B1 | 10/1998 |
| EP | 0 430 402 B1 | 1/1999 |
| EP | 0 529 666 B1 | 4/2000 |
| EP | 0 994 342 A3 | 4/2000 |
| EP | 0 752 133 B1 | 6/2000 |
| EP | 1 018 644 A2 | 7/2000 |

| | | | | | |
|---|---|---|---|---|---|
| EP | 1 118 268 A1 | 7/2001 | WO | WO 99/60397 A1 | 11/1999 |
| EP | 1 147 774 A1 | 10/2001 | WO | WO 9957955 | 11/1999 |
| EP | 0 534 033 B1 | 11/2001 | WO | WO 99/61888 A2 | 12/1999 |
| EP | 0 925 494 B1 | 12/2001 | WO | WO 00/06193 A1 | 2/2000 |
| EP | 0 748 316 B1 | 5/2002 | WO | WO 00/12204 | 3/2000 |
| EP | 0 662 124 B1 | 6/2002 | WO | WO 00/36396 | 6/2000 |
| EP | 1 245 944 A3 | 10/2002 | WO | WO 00/49387 | 8/2000 |
| EP | 1 249 502 A2 | 10/2002 | WO | WO 00/54026 | 9/2000 |
| EP | 1250897 A1 | 10/2002 | WO | WO 00/56444 | 9/2000 |
| EP | 1 380 304 A2 | 1/2004 | WO | WO 00/70080 | 11/2000 |
| EP | 1403633 A3 | 4/2004 | WO | WO 01/02836 A1 | 1/2001 |
| EP | 1 100 400 B1 | 5/2004 | WO | 0129538 | 4/2001 |
| EP | 1 257 168 B1 | 2/2005 | WO | WO 01/28700 A1 | 4/2001 |
| FR | 2574656 A1 | 6/1986 | WO | WO 0129538 | 4/2001 |
| FR | A-2 635453 | 2/1990 | WO | WO 01/37655 A1 | 5/2001 |
| FR | 2 647 668 A | 12/1990 | WO | WO 01/40765 A2 | 6/2001 |
| FR | 2699678 A1 | 6/1994 | WO | WO 01/40765 A3 | 6/2001 |
| GB | 1471019 | 4/1977 | WO | WO 01/42757 A2 | 6/2001 |
| GB | 2 121 976 A | 1/1984 | WO | WO 01/51612 A1 | 7/2001 |
| GB | 2 122 369 A | 1/1984 | WO | WO 01/61313 A2 | 8/2001 |
| GB | 2 125 181 A | 2/1984 | WO | WO 01/68110 | 9/2001 |
| GB | 2 136 561 A | 9/1984 | WO | WO 01/68226 A2 | 9/2001 |
| GB | 2 137 352 A | 10/1984 | WO | WO 01/71348 A1 | 9/2001 |
| GB | 2145112 | 2/1985 | WO | WO 01/75161 A2 | 10/2001 |
| GB | 2 144 542 A | 3/1985 | WO | WO 0175176 | 10/2001 |
| GB | 2 153 521 A | 8/1985 | WO | WO 01/85913 A2 | 11/2001 |
| GB | 2 243 681 A | 11/1991 | WO | WO 01/85913 A3 | 11/2001 |
| GB | 2 360 360 A | 9/2001 | WO | WO 01/90295 A1 | 11/2001 |
| JP | 61139747 (A) | 6/1986 | WO | WO 02041906 A2 | 11/2001 |
| JP | 61159135 (A) | 7/1986 | WO | WO 01/95815 A2 | 12/2001 |
| JP | 2024535 | 1/1990 | WO | WO 02/01189 A1 | 1/2002 |
| JP | 4126064 (A) | 4/1992 | WO | WO 02/04666 A2 | 1/2002 |
| JP | 4126065 (A) | 4/1992 | WO | WO 02/19594 | 3/2002 |
| JP | 4126066 (A) | 4/1992 | WO | WO 02/19943 A1 | 3/2002 |
| JP | 4126079 (A) | 4/1992 | WO | WO 02/20850 A2 | 3/2002 |
| JP | 4126080 (A) | 4/1992 | WO | WO 02/21102 A2 | 3/2002 |
| JP | 4126081 (A) | 4/1992 | WO | WO 02/23163 A1 | 3/2002 |
| SU | 1056008 | 11/1983 | WO | WO 02/25269 A2 | 3/2002 |
| SU | 1260778 A1 | 9/1986 | WO | WO 02/26114 A2 | 4/2002 |
| WO | WO 84/01265 A1 | 4/1984 | WO | WO 02/28311 A1 | 4/2002 |
| WO | WO 85/04014 A1 | 9/1985 | WO | WO 02/29106 A2 | 4/2002 |
| WO | WO 88/07198 | 9/1988 | WO | 02041906 A2 | 5/2002 |
| WO | WO 89/04470 A1 | 5/1989 | WO | WO 02/41906 A2 | 5/2002 |
| WO | WO 89/04471 A1 | 5/1989 | WO | WO 02/43486 A1 | 6/2002 |
| WO | WO 90/13315 A1 | 11/1990 | WO | WO 02/43574 A3 | 6/2002 |
| WO | 9105236 | 4/1991 | WO | WO 02/44319 A2 | 6/2002 |
| WO | WO 9105236 | 4/1991 | WO | WO 02/052244 A2 | 7/2002 |
| WO | WO 92/08120 A1 | 5/1992 | WO | WO 02/054044 A2 | 7/2002 |
| WO | WO 92/17288 A1 | 10/1992 | WO | WO 02/057775 A1 | 7/2002 |
| WO | WO 93/10803 | 6/1993 | WO | WO 02/060880 A1 | 8/2002 |
| WO | WO 93/17322 A1 | 9/1993 | WO | WO 03020877 A2 | 8/2002 |
| WO | WO 94/22001 A1 | 9/1994 | WO | WO 02/077637 A1 | 10/2002 |
| WO | WO 96/04542 A1 | 2/1996 | WO | WO 02/092161 A1 | 11/2002 |
| WO | WO 96/12171 A2 | 4/1996 | WO | WO 02/092247 A1 | 11/2002 |
| WO | WO 96/12172 | 4/1996 | WO | WO 03/008102 A1 | 1/2003 |
| WO | WO 96/12173 A1 | 4/1996 | WO | WO 03/008937 A2 | 1/2003 |
| WO | WO 96/31764 | 10/1996 | WO | WO 03/012403 A1 | 2/2003 |
| WO | WO 96/33806 A1 | 10/1996 | WO | WO 03/016875 A2 | 2/2003 |
| WO | WO 97/29354 A1 | 8/1997 | WO | 03020877 A2 | 3/2003 |
| WO | WO 97/30338 A1 | 8/1997 | WO | WO 03/056330 A2 | 7/2003 |
| WO | WO 97/35189 A1 | 9/1997 | WO | WO 03/056335 A2 | 7/2003 |
| WO | WO 97/43620 A1 | 11/1997 | WO | WO 03/072765 A1 | 9/2003 |
| WO | WO 89/04472 A1 | 5/1998 | WO | WO 03/078065 A1 | 9/2003 |
| WO | WO 98/34094 A1 | 8/1998 | WO | WO 03/078972 A1 | 9/2003 |
| WO | WO 98/48259 | 10/1998 | WO | WO 04001401 | 12/2003 |
| WO | WO 98/57152 A1 | 12/1998 | WO | WO 2004/006916 A1 | 1/2004 |
| WO | WO 99/05504 A2 | 2/1999 | WO | WO 2004/009237 A2 | 1/2004 |
| WO | WO 99/33956 A1 | 7/1999 | WO | WO 2004/009237 A3 | 1/2004 |
| WO | WO 99/38883 A1 | 8/1999 | WO | WO 2004/012837 A2 | 2/2004 |
| WO | WO 99/42810 A1 | 8/1999 | WO | WO 2004/012837 A3 | 2/2004 |
| WO | WO 99/44035 | 9/1999 | WO | WO 2004/017041 A2 | 2/2004 |
| WO | WO 99/44037 A1 | 9/1999 | WO | WO 2004/017041 A3 | 2/2004 |
| WO | WO 99/47906 A1 | 9/1999 | WO | WO 2004/024227 A2 | 3/2004 |

| | | | |
|---|---|---|---|
| WO | WO 2004/024227 A3 | 3/2004 | |
| WO | WO 2004/046712 A2 | 6/2004 | |
| WO | WO 2004/059282 A2 | 7/2004 | |
| WO | WO 2004/003697 A2 | 10/2004 | |
| WO | WO 2004/087177 A1 | 10/2004 | |
| WO | WO 2004/088283 A2 | 10/2004 | |
| WO | WO 2004/104178 A2 | 12/2004 | |
| WO | WO 2004/104178 A3 | 12/2004 | |
| WO | WO 2005/094852 A2 | 10/2005 | |
| WO | WO 2005/095590 A2 | 10/2005 | |
| WO | WO 2005/095960 A1 | 10/2005 | |
| WO | WO 2006/015056 A2 | 2/2006 | |
| WO | WO 2006012597 A2 | 2/2006 | |
| WO | 2006060770 A2 | 8/2006 | |
| WO | WO 2006060770 A2 | 8/2006 | |
| WO | 2007016090 A2 | 2/2007 | |
| WO | WO 2007016090 A2 | 2/2007 | |

OTHER PUBLICATIONS

Australian Application No. 17552/01; Notice of Acceptance dated Jul. 29, 2005.
Australian Application No. 17552/01, Statement of Grounds and particulars of Opposition filed by Monsanto; Mar. 8, 2006.
Chinese Application No. 00818617.0, Notification of First Office Action.
European Appliction No. 00980567.9, Certificate of Grant of Patent dated Feb. 2, 2005.
European Appliction No. 00980567.9, European examination report dated Jun. 23, 2003.
European Appliction No. 00980567.9; Opposition filed by Greenpeace Nov. 2, 2005 (This documents in filed herewith in German. A translation will be forwarded to the Examiner once it is received.).
European Appliction No. 00980567.9; Opposition filed by Monsanto Oct. 31, 2005.
European Appliction No. 00980567.9;Opposition filed by European Union Parliament Nov. 5, 2005 (This documents in filed herewith in German. A translation will be forwarded to the Examiner once it is received.).
European Appliction No. 05001937.1, European Search Report dated May 4, 2005.
New Zealand Application No. 519078, Examination Report dated Jul. 3, 2004.
New Zealand Application No. 519078, Letters Patent No. 519078 dated Nov. 22, 2000.
New Zealand Application No. 530441, Examination Report dated Jan. 8, 2004.
U.S. Appl. No. 09/478,299, Office Action dated Apr. 18, 2003.
U.S. Appl. No. 09/478,299, Office Action dated May 13, 2005.
U.S. Appl. No. 09/478,299, Office Action dated Aug. 26, 2004.
U.S. Appl. No. 09/478,299, Office Action dated Sep. 6, 2001.
U.S. Appl. No. 09/478,299, Office Action dated Dec. 4, 2003.
U.S. Appl. No. 09/478,299; Office Action dated Feb. 9, 2006.
U.S. Appl. No. 11/092,313, Office Action dated Oct. 6, 2006.
U.S. Appl. No. 11/092,313, Response to Election filed by Applicant on Sep. 11, 2006.
Abdel-Ghaffar, A. E., et al., "Rabbit Semen Metabolism" in Rabbit Production in Hot Climates Baselga and Marai (eds); International Conference of Rabbit Production in Hot Climates 1994, p. 305-312.
Akhtar, S., et al., "Prevalence of Five Stereotypes of Bluetongue Virus in a Rambouillet Sheep Flock in Pakistan", Veterinary Record 136, p. 495. (1995).
Aldrich, S. L., et al., "Parturition and Periparturient Reproductive and Metabolic Hormone Concentration in Prenatally Androgenized Beef Heifers", J. Anim. Sci. 73:3712. (1995).
Amann, R. P. et al., "Issues Affecting Commercialization of Sexed Sperm" Therio. 52:1441. (1999).
Amann, R. P., et al. "Prospects For Sexing Mammalian Sperm," Animal Reproduction Laboratory College of Veterinary Medicine and Biomedical Sciences, Colorado State University. (1982).

Amann, R.P. "Fertilizing Potential Vitro of Semen from Young Beef Bulls Containing a High or Low Percentage of Sperm with a Proximal Droplet" Theriogenology 54: 1499-1515, 2000.
Amann, Rupert P. "Cryopreservation of Sperm" 1999, Encyclopedia of Reproduction 1:733-783.
American Meat and Science Association in Cooperation with National Livestock and Meat Board, "Research Guidelines for Cookery and Sensory Evaluation and Instrumental Tenderness Measurements for Fresh Meat". (1995).
Amoah, E. A. and Gelaye, S., "Biotechnological Advances in Goat Reproduction", J. Anim. Sci. 75(2): 578-585. (1996).
Anderson, V. K., et al., Intrauterine and tiefzervikale Insemination mit Gefriersperma bein Schat (Intrauterine and Deep Cervical Insemination With Frozen Semen in Sheep). Zuchthygiene 8:113-118. (1973).
Arriola, J. and Foote, R.H.: "Glycerolation and Thawing Effects on Bull Spermatozoa frozen in Detergent-Treated Egg Yok and Whole Egg Extenders," J Dairy Sci, 70:1664-1670 (1987).
Asbury, Charles A. "Fluorescence Spectra of DNA Dyes Measured in a Flow Cytometer," University of Washington Feb. 19, 1996.
Bagley, C. P. "Nutritional Management of Replacement Beef Heifers: a Review" J. Anim. Science 71:3155-3163. (1993).
Bailey, C. M. et al., "Nulliparous Versus Primiparous Crossbred Females for Beef", J. Anim. Sci. 69:1403. (1991).
Baker, R.D., et al., "Effect of Volume of Semen, Number of Sperm and Drugs on Transport of Sperm in Artificially Inseminated Gilts", J. Anim. Sci. 27:88-93. (1968).
Bakker Schut, Tom C. "A New Principle of Cell Sorting by Using Selective Electroportation in a Modified Flow Cytometry," University of Twente, Mar. 10, 1990.
Barnes, F. L. and Eyestone, W. H., "Early Cleavage and the Maternal Zygotic Transition in Bovine Embryos", Therio. vol. 33, No. 1, pp. 141-149. (1990).
Batellier, F. et al., "Advances in Cooled Semen Technology" Animal Reproduction Science 68 p. 181-190 (2001).
Becker, S.E. and Johnson, A. L. "Effects of Gonadotropin-Releasing Hormone Infused in a Pulsatile or Continuous Fashion on Serum Gonadotropin Concentrations and Ovulation in the Mare", J. Anim. Sci. 70:1208-1215. (1992).
Bedford, S .J. and Hinrichs, K., "The Effect of Insemination Volume on Pregnancy Rates of Pony Mares", Therio. 42:571-578. (1994).
Behrman, S. J., et al., "Freeze Preservation of Human Sperm" American Journal of Obstetrics and Gynecology vol. 103 (5) p. 654-664 Mar. 1, 1969.
Bellows, R. A., et al., "Cause and Effect Relationships Associated With Calving Difficulty and Calf Birth Weight", J. Anim. Sci. 33:407. (1971).
Berardinelli, J. G., et al., "Source of Progesterolle Prior to Puberty in Beef Heifers". J. Anim. Sci. 49:1276. (1979).
Berger, G. S. "Intratubal Insemination", Fertil. Steril. 48:328-330, (1987).
Bergfeld, E. G., et al., "Ovarian Follicular Development in Prepubertal Heifers is Influenced by Level of Dietary Energy Intake", Bio. of Repro. 51:1051. (1994).
Berry, B. W., et al., "Beef Carcass Maturity Indicators and Palatability Attributes", J. Anim. Sci. 38:507 (1974).
Beyhan, Z., et al., "Sexual Dimorphism in IVF Bovine Embryos Produced by Sperm Sorted by High Speed Flow Cytometry", abstr. Therio. 49(1): 359 (1998).
Beyhan, Z., et al., 1999 Sexual Dimorphism In IVM-IVF Bovine Embryos Produced from X and Y Chromosome-Bearing Spermatozoa Sorted By High Speed Flow Cytometry. Theriogenology. 52: 35-48.
Bigos, Martin "Nine Color Eleven Parameter Immunophenotyping Using Three Laser Flow Cytometry," Stanford University Dec. 22, 1998.
Bioxcell, Bovine Sperm Preservation, Advertisement Jun. 28, 2005.
Bond, J., et al., "Growth and Carcass Traits of Open Beef Heifers Versus Beef Heifers That Have Calved", Nutrition Reports International 34:621. 1986.
Boucque, C. V., et al., "Beef-Production With Maiden and Once-Calved Heifers", Livestock Prod. Sci. 7:121. 1980.

Bourdon, R. M. and J. S. Brinks. "Simulated Efficiency of Range Beef—Production III. Culling Strategies and Nontraditional Management-Systems", J. Anim. Sci. 65:963. 1987.

Bracher, V. and Allen, W.R., "Videoendoscopic Examination of the Mare's Uterus: I. Findings in Normal Fertile Mares", Equine Veterinary Journal, vol. 24, p. 274-278. 1992.

Braselton, W. E. and McShan, W. H., "Purification and Properties of Follicle Stimulating and Luteinizing Hormones From Horse Pituitary Glands" Arch. Biochem. Biophys. 139:45-48. 1970.

Braun, J. et al, "Effect of Different Protein Supplements on Motility and Plasma Membrane Integrity of Frozen- Thawed Stallion Spermatozoa", Cryobiology (1995) 32:487-492.

Brethour, J. R. and Jaeger, J. R., "The Single Calf Heifer System", Kansas Agric. Sta. Rep of Progress 570. 1989.

Brinsko, S.P. et al., "Artificial Insemination and Preservation of Semen." Veterinary Clinics of North America:Equine Practice vol. 8 No. 1 Apr. 1992 pp. 205-218.

Bristol, F. "Breeding Behavior of a Stallion at Pasture With 20 Mares in Synchronized Oestrus" J. Reprod. Fertil. Suppl. 32:71. 1982.

Brookes, A. J. and O'Byrne, M., "Use of Cow-Heifers in Beef Production" J. of the Royal Agricultural Society of England 126:30. 1965.

Buchanan, B. R., et al, "Insemination of Mares with Low Numbers of Either Unsexed or Sexed Spermatozoa", Therio. vol. 53, p. 1333-1344. 2000.

Buchanan, B.R. "Pregnancy Rates in Mares Following a Single Insemination with a Low Number of Spermatozoa into the Tip of the Uterine Horn" Theriogenology p. 395.

Burns, P. D. and Spitzer, J.C., "Influence of Biostimulation on Reproduction in Postpartum Beef-Cows", J. Anim. Sci. 70:358. 1992.

Burwash, L. D., et al., "Relationship of Duration of Estrus to Pregnancy Rate in Normally Cycling, Non Lactating Mares" J.A.V.M.A. 165:714-716. 1974.

Byerley, D. J., et al., "Pregnancy Rates of Beef Heifers Bred Either on Puberal or Third Estrus". J Anim. Sci. 65:645. 1987.

Caslick, E. A., "The Vulva and the Vulvo-Vaginal Orifice and its Relation to Genital Health of the Thoroughbred Mare", Cornell Veterinarian, vol. 27, p. 178-187. 1937.

Catt, et al., "Assessment of Ram and Boar Spermatozoa During Cell-Sorting by Flow Cytometry", Reproduction Dom Animal, vol. 32, pp. 251-258. 1997.

Catt, S. L., et al., "Birth of a Male Lamb Derived from an In Vitro Matured Oocyte Fertilized by Intracytoplasmic Injection of a Single Presumptive Male Sperm", Veterinary Record 139, p. 494-495. 1996.

Cave-Penney, Tony, "Sexed Semen Offers Faster Genetic Gain", Farming News, Livestock Supplement, Feb. 1997, p. 28.

Celestron: Telescope Basics: www.celestron.com/tb-2ref/htm; 4 pages.

Chandler, J. E., "Videomicroscopic Comparison of Bull Sperm and Leukocyte Chromosome Areas as Related to Gender", J Dairy Sci 73, p. 2129-2135. 1990.

Chandler, J. E., et al, "Bovine Spermatozoal Head Size Variation and Evaluation of a Separation Technique Based on this Size", Therio. 52, p. 1021-1034. 1999.

Chen, S.H. "Effects of Oocyte Activation and Treatment of Spermatozoa on Embryonic Development Following Intracytoplasmic Sperm Injection in Cattle" Theriogenology 48: 1265-1273, 1997.

Chen, Y. et al., Survival of Bull Spermatozoa Seeded and Frozen at Different Rates in Egg Yolk-Tris and Whole Milk Extenders, 1993 J Dairy Sci 76:1028-1034.

Chin, W. W. and Boime, I. 1990. In Glycoprotein Hormones. Serona Symp. Norwell, MA. pp. 19-20.

Choi, Y.H. "Developmental Cappacity of Equine Oocytes Matured and Cultured in Equine Trophoblast-Conditioned Media" Theriogenoogy 56: 320-339, 2001.

Chung, Y. G., et al. "Artificial insemination of Superovulated Heifers With 600,000 Sexed Sperm". J Anim. Sci. Suppl. 1. 836:215. 1998 abstr.

Clement, F., et al., "Which Insemination Fertilizes When Several Successive Inseminations are Performed Before Ovulation" 7th Int. Symp. Eq. Repro. 151. 1998 abstr.

Cran, D. G., et al, "Production of Lambs by Low Dose Intrauterine Insemination With Flow Cytometrically Sorted and Unsorted Semen", Therio. p. 267. 1997.

Cran, D. G., et al., "Sex Preselected in Cattle: A Field Trial", Veterinary Record 136, 1995, p. 495-496.

Cran, D. G., et al., "Production of Bovine Calves Following Separation of X- and Y-Chromosome Bearing Sperm and In Vitro Fertilization". Vet. Rec. 132:40-41. 1993.

Cran, D. G., et al., "The Predetermination of Embryonic Sex Using Flow Cytometrically Separated X and Y Spermatozoa" Human Reproduction Update 1996, vol. 2 (4) p. 355-63.

Crowley, J. P. "The facts of Once-Bred Heifer Production" School of Agric., Univ. of Aberdeen, Scotland. 1973.

Cui, K. et al, "X Larger than Y", Nature 366, p. 177-118, 1993.

Cui, K., "Size Differences Between Human X and Y Spermatozoa and Prefertilization Diagnosis", Molecular Human Reproduction, vol. 3, No. 1, pp. 61-67. 1997.

Curran, S. "Fetal Gender Determination" in *Equine Diagnostic Ultrasonography* 1st ed. Rantanen, N.W. and McKinnon A.O. (eds.) Williams and Williams, 1998, p. 165-69.

da Silva, Coutinho M.A.. "Effect of time of oocyte collection and site of insemination on oocyte transfer in mares." Animal Reproduction and Biotechnology Laboratiory, Colorado State Uniuversity, Fort Collins Journal of Animal Science 2002. 80:1275-1279.

DakoCytomation, "MoFlo® Sorters" http://www.dakocytomation.us/prod_productrelatedinformation?url=gprod_moflo_index.htm one page, printed Jun. 26, 2003.

Database up 1 BR9704313 (Alves, De Resende et al) Jun. 4, 1999.

Day, B. N., et al. Birth of Piglets Preselected for Gender Following In Vitro Fertilization of In Vitro Matured Pig Oocytes by X and Y Bearing Spermatozoa Sorted by High Speed Flow Cytometry. Therio. 49(1): 360. 1998 abstr.

de Leeuw, F.E. et al:"Effects of carious cryoprotective agents and membrane-stabilizing compounds on bull sperm emebrane integrity after cooling and freezing" Cryobiology US, Academic Press Inc 1993 pp. 32-44.

Dean, P.N., et al. "Hydrodynamic Orientation of Spermatozoa Heads for Flow Cytometry". Biophys. J. 23:7-13. 1978.

Demick, D.S., et al. "Effect of Cooling, Storage, Glycerization and Spermatozoal Numbers on Equine Fertility" J. Anim. Sci. 43:633-637. 1976.

DenDaas, J. H. G., et al. "The relationship between the number of spermatozoa inseminated and the reproductive efficiency of dairy bulls" J Dairy Sci. 81: 1714-1723. 1998.

Denham, A. "In-vitro studies on Sandhill Range Forage as Related to Cattle Preference", M.S. Thesis. Colorado State University. 1965.

Denk, Winfried. "Two-Photon Molecular Excitation in Laser-Scanning Microscopy," Handbook of Biological Confocal Microscopy. 1995.

Deutscher, G. H. "Extending Interval From Seventeen to Nineteen Days in the Melengestrol Acetate-Prostaglandin Estrous Synchronization Program for Heifers". The Professional Animal Scientist 16:164. 2000.

Diagnostic Products Corporation, "Coat-A-Count" http://www.Progesterone.com. 1998.

Dikeman, M. E. "Cattle Production Systems to Meet Future Consumer Demands" J. Anim. Sci. 59:1631, 1984.

Dinnyes, A., et al., "Timing of the First Cleavage Post- Insemination Affects Cryosurvival of In Vitro-produced Bovine Blastocysts", Molec. Reprod. Develop. 53, p. 318-324. 1999.

Dippert, K.D. "Fertilization Rates in Superovulated and Spontaneously Ovulating Mares" Theriogenology 41: 1411-1423, 1994.

Donaldson, L. E., "Effect of Insemination Regimen on Embryo Production in Superovulated Cows", The Veterinary Record, Jul. 13, p. 35-37, 1985.

Donoghue, A.M., et al. "Timing of Ovulation after Gonadotropin Induction and its Importance to Successful Intrauterine Insemination in the Tiger (*Panthera tigris*)" J. Reprod. Fertil. 107:53-58. 1996.

Douglas, R. H., "Review of Induction of Superovulation and Embryo Transfer in the Equine" Therio. 11:33-46. 1979.

Douglas, R. H., et al. "Induction of Ovulation and Multiple Ovulation on Seasonally-Anovulatory Mares with Equine Pituitary Fractions." Therio. 2(6): 133-142. 1974.

Doyle, S. P., et al. "Artificial Insemination of Lactating Angus Cows with Sexed Semen". Proc. Western Sect. Am. Soc. Anim. Sci. 50:203. 1999.

Dresser D.W. et at. Analysis of DNAcontent ofLiving Spermatozoa Using Flow Cytometry Technique Journal of Reproduction and Fertility, 1993, vol. 98, pp. 357-365.

Duchamp, G., et al. "Alternative Solutions to hCG Induction of Ovulation in the Mare" J. Reprod. Fertil. Suppl. 35:221-228. 1987.

Evans, M. J. and Irvine, C. H. G. "Induction of Follicular Development, Maturation and Ovulation by Gonadotropin Releasing Hormone Administration to Acyclic Mares" Bio. Reprod. 16:452-462. 1977.

Ferrell, C. L. Effects of Post-Weaning Rate of Gain on Onset of Puberty and Productive Performance of Heifers of Different Breeds. J. Anim. Sci. 55:1272. 1982.

Ferrell, C. L. and T. G. Jenkins. "Energy-Utilization by Mature, Nonpregnant, Nonlactating Cows of Different Types" J. Anim. Sci. 58:234. 1984.

Field, R. A., et al., "Bone-Ossification and Carcass Characteristics of Wethers Given Silastic Implants Containing Estradiol", J. Anim. Sci. 68:3663-3668. 1990.

Field, R. et al., "Growth, Carcass, and Tenderness Characteristics of Virgin, Spayed, and Single-Calf Heifers", J. Anim. Sci. 74:2178. 1996.

Fitzgerald, B. P., et al. "Effect of Constant Administration of a Gonadotropin-Releasing Hormone Agonist on Reproductive Activity in Mares: Preliminary Evidence on Suppression of Ovulation During the Breeding Season." Am. J. Vet. Res. 54:1746-1751. 1993.

Fluharty, F. L., et al., "Effects of Age at Weaning and Diet on Growth of Calves",Ohio State University Dept. of Animal Scieneces. 1966 Ohio Agri. Res. And Den. Circular, 156:29 1966.

Foote, et al. Motility and Fertility of Bull Sperm Frozen-Thawed Differently in Egg Yolk and Milk Extenders Containing Detergent, 1987 J Dairy Sci 70:2642-2647.

Foote, R.H., "Buffers and Extenders: What Do They Do? Why Are They Important?" Proc of the NAAB Tech. Conf. On Artificial Insemination and Reproduction, 62-70 (1984).

Foulkes, J. A., et al. "Artificial Insemination of Cattle Using Varying Numbers of Spermatozoa." Vet. Rec. 101:205. 1977.

Francon, M. and Yamamoto, T., "Un Noveau et tres simple dispositif interferentiel applicable as microscope" Optica Acta 9, p. 395-408. 1962.

Fugger, E. F. "Clinical Experience with Flow Cytometric Separation of Human X- and Y-Chromosome Bearing Sperm", Therio. vol. 52, pp. 1435-1440.1999.

Fuller, Robert R. "Characterizing Submicron Vesicles With Wavelenth-Resolved Fluorescence in Flow Cytometry," University of Illinois, May 13, 1996.

Fulwyler, M. J. "Electronic Separation of Biological Cells by Volume." Science. 150:910. 1965.

Fulwyler, M. J. "Hydrodynamic Orientation of Cells." J of Histochem. and Cytochem. 25:781-783. 1977.

Garner, D. L., et al. "Quantification of the X and Y Chromosome-Bearing Spermatozoa of Domestic Animals by Flow Cytometry." Biol. Reprod. 28:312-321. 1983.

Ginther, O. J., "Sexual Behavior Following Introduction of a Stallion into a Group of Mares" Therio. vol. 19 (6) Jun. 1983.

Ginther, O. J., "Some Factors Which Alter Estrus Cycle in Mares." J. Anim. Sci. 33:1158. 1971 abstr.

Ginther, O. J., Reproductive Biology of the Mare. (2nd Ed.) Equiservices, Cross Plains, WI. 1992.

Gledhill, B. L. "Gender Preselection: Historical, Technical and Ethical Perspective." Semen Reprod. Endocrinol. 6:385-395. 1988.

Gombe, S. and Hansel, W. "Plasma Luteinizing Hormone (LH) and Progesterone Levels in Heifers on Restricted Energy Intakes." J. Anim. Sci. 37:728. 1973.

Goppert-Mayer,"Uber Elementarakte mit zwei Quantensprungen Von Maria Copper—Mayer".

Gottlinger et al., "Operation of a Flow Cytometer", Flow Cytometry and Cell Sorting, A. Radbruch (Ed.), 1992, pp. 7-23.

Gourley, D. D. and Riese, R. L. "Laparoscopic Artificial Insemination in Sheep." Vet. Clin. N. Amer: Food Anim. Prac. 6(3): 615-633 (1990).

Graham, J. Analysis of Stallion semen and its Relation to Fertility. Abstract Complete article from Reproductive Technology vol. 12 # 1 Apr. 1996 now included in XYIDS000213.

Graham, J.K. and Hammerstedt, R.H.: "Differential Effects of Butylated Hydroxytoluene Analogs on Bull Sperm Subjected to Cold-Induced Membrane Stress," Cryobiology, 29:106-117 (1992).

Graham, James K., "Effect of Cholesterol-Loaded Cyclodextrins in Semen Extenders", Proceedings of the 19th Technical Conference on Artificial Insemination & Reproduction, 2003, pp. 91-95.

Gravert, H. O., "Genetic Aspects of Early Calving." In: J.C. Taylor (Ed.) *The Early Calving of Heifers and Its Impact on Beef Production*. 59 (1975).

Gregory, K. E., et al., "Characterization of Biological Types of Cattle—Cycle III: II Growth Rate and Puberty in Females" J. Anim. Sci. 49:461 (1979).

Grimes, I. F, and T. B. Turner. "Early Weaning of Fall Born Calves II. Post Weaning Performance of Early and Normal Weaned Calves". I. Prod. Agric. 4:168 (1991).

Grondahl, C., et al, "In Vitro Production of Equine Embryos", Biology of Reproduction, Monograph Series I, p. 299-307 (1995).

Guillou, F. and Combarnous, Y. "Purification of Equine Gonadotropins and Comparative Study of Their Acid-Dissociation and Receptor-Binding Specificity." Biochemica Et Biophysica Acta 755:229-236 (1983).

Gurnsey, M. P., and Johnson, L.A., "Recent Improvements in Efficiency of Flow Cytometric Sorting of X and Y-Chromosome Bering Sperm of Domestic Animals: a Review" New Zealand Society of Animal Protection, three pages (1998).

Hall, J. B., et al., "Effect of Age and Pattern of Gain on Induction of Puberty with a Progestin in Beef Heifers." J. Anim. Sci. 75:1606 (1997).

Hamamatsu, "Technical Information, Optical Detector Selection: A Delicate Balancing Act", web page, http://www.optics.org/hamamatsu/photodiode.html, printed on Apr. 15, 2000. 6 pages total.

Hamano, K., et al., "Gender Preselection in Cattle with Intracytoplasmically Injected, Flow Cytometrically Sorted Sperm Heads", Biology of Reproduction 60, p. 1194-1197 (1999).

Hammerstedt, et al., "Cryopreservation of Mammalian Sperm: What We Ask Them to Survive," Journal of Andrology, 11:1:73-88 (1990).

Harrison, L.A., et al., "Comparison of HCG, Buserelin and Luprostiol for Induction of Ovulation in Cycling Mares." Eq. Vet. Sci. 3:163-166 (1991).

Harte, F. J. "System of Production of Beef From Once Calved Heifers." In: J.C. Taylor (Ed.) *The Early Calving of Heifers and its Impact on Beer Production*. 123 (1975).

Early Calving of Heifers and its Impact on Beef Production. 123 (1975).

Hawk, H. W., et al., "Fertilization Rates in Superovulating Cows After Deposition of Semen on the Infundibulum Near the Uterotubal Junction or After Insemination with High Numbers of Sperm", XP-002103478, Therio. vol. 29, No. 5, p. 1131-1142 (1988).

Hermesmeyer, G. N., et al. "Effects of Prenatal Androgenization and Implantation on the Performance and Carcass Composition of Lactating Heifers in the Single-Calf Heifer System." The Professional Animal Scientist 15:173. 1999.

Herweijer, Hans. "High-Speed Photodamage Cell Selection Uing Bromodeoxyuridine/Hoechst 33342 Photosensitized Cell Killing," Sep. 23, 1987.

Herzenberg, Leonard A. "Flourescence-activated Cell Sorting," pp. 108-117.

Hilton, G. G., et al., "An Evaluation of Current and Alternative Systems for Quality Grading Carcasses of Mature Slaughter Cows." J. Anim. Sci. 76:2094. 1998.

Ho, L., et al., "Influence of Gender, Breed and Age on Maturity Characteristics of Sheep." J. Anim. Sci. 67:2460-2470. 1989.

Hofferer, S., et al. "Induction of Ovulation and Superovulation in Mares Using Equine LH and FSH Separated by Hydrophobic Interaction Chromatography." J. Reprod. Fertil. 98:597-602. 1993.

Hohenboken, W. D. "Applications of sexed semen in cattle production." Therio. 52:1421. 1999.

Holtan, D. W., et al., "Estrus, Ovulation and Conception Following Synchronization With Progesterone, Prostaglandin F2a and Human Chorionic Gonadotropin in Pony Mares." J. Anim. Sci. 44:431-437. 1977.

Horan, Paul K. "Quantitative Single Cell Ana,lysis and Sorting, Rapid Analysis and sorting of cells is emerging as an important new technology in research and medicine."

Householder, D. D., et al. "Effect of Extender, Number of Spermatozoa and hCG on Equine Fertility." J. Equine Vet. Sci. 1:9-13. 1981.

Howard, J. G., et al., "Comparative Semen Cryopreservation in Ferrets (*Mustela putorious furo*) and Pregnancies After Laparoscopic Intrauterine Insemination With Frozen-Thawed Spermatozoa." J. Reprod. Fertil. 92:109-118. 1991.

Howard, J. G., et al., "Sensitivity to Exogenous Gonadotropins for Ovulation and Laparoscopic Artificial Insemination in the Cheetah and Clouded Leopard." Biol. Reprod. 56:1059-1068. 1997.

Hunter, R. H. F. "Transport and Storage of Spermatozoa in the Female Tract." Proc 4th Int. Congress Anim. Repro. and A. I. 9:227-233. 1980.

Hyland, J. H., et al., "Gonadotropin Releasing Hormone (GnRH) Delivered by Continuous Infusion Induces Fertile Estrus in Mares During Seasonal Acyclity" Proceedings of the Annual Convention of the American Association of Equine Practitioners (34th) 989, p. 181-190.

IMV Technologies, Protocol of Bioxcell with Fresh Semen, 1 page, 2000.

IMV Technologies, Protocol of Bioxcell with Frozen Semen, 2 pages, 2000.

Irvine, C H. G. and Alexander, S. L. "GnRH" Chapter 4 in Equine Reproduction, McKinnon and Voss eds. Lea and Febiger. Philadelphia, London. p. 37. (1993).

Iwazumi, Y., et al., "Superovulation Using CIDR in Holstein Cows" J. of Reprod. Dev. vol. 40 (3) 1994, pp. 259-266.

Jafar, et al., "Sex Selection in Mammals: A Review", Therio. vol. 46, p. 191-200. (1996).

Jakubiczka, S. et al. "A Bovine Homologue of the Human TSPY Gene." Genomics. 1993, vol. 17, No. 3, pp. 732-735.

Jarriage, R. "Age of Cows at First Calving in France." In: J.C. Taylor (Ed.) *The Early Calving of Heifers and its Impact on Beef Production*. 10. (1975).

Jasko, D. J., et al., "Effect of Insemination Volume and Concentration of Spermatozoa on Embryo Recovery in Mares", Therio. 37:1233-1239, (1992).

Jasko, D. J., et al., "Pregnancy Rates Utilizing Fresh, Cooled and Frozen-Thawed Stallion Semen", American Association of Equine Practitioners 38th Annual Convention Proceedings, 1992, p. 649-60.

Johnson, A. L. "Pulsatile Administration of Gonadotropin Releasing Hormone Advances Ovulation in Cycling Mares", Biol. Reprod. 35:1123-1130, (1986).

Johnson, A. L., et al. "Use of Gonadotropin-Releasing Hormone (GnRH) Treatment to Induce Multiple Ovulations in the Anestrous Mare" Eq. Vet. Sci. 8:130-134, (1988).

Johnson, L.A., "Flow Cytometric Determination of Spermatozoa Sex Ratio in Semen Purportedly Enriched for X or Y Bearing Spermatozoa", Therio. 29:265 abstr.

Johnson, L.A., "Gender Preselection in Domestic Animals Using Flow Cytometrically Sorted Sperm" J. Anim. Sci. (Suppl I) 70:8-18. (1992).

Johnson, L.A., "The Safety of Sperm Selection by Flow Cytometry" Ham. Reprod. 9(5): 758. (1994).

Johnson, L.A., "Advances in Gender Preselection in Swine" Journal of Reproduction and Fertility Supplement, vol. 52, p. 255-266 (1997).

Johnson, L.A., "Gender Preselection in Humans? Flow Cytometric Separation of X and Y Spermatozoa for the Prevention of X-Linked Diseases" Human Reproduction vol. 8 No. 10, p. 1733-1739 (1993).

Johnson, L.A., "Gender Preselection in Mammals: An Overview", Deutsch. Tierarztl. Wschr, vol. 103, p. 288-291 (1996).

Johnson, L.A., "Isolation of X- and Y-Bearing Spermatozoa for Sex Preselection." Oxford Reviews of Reproductive Biology. Ed. H. H. Charlton. Oxford University Press. 303-326. (1994).

Johnson, L.A., "Sex Preselection by Flow Cytometric Separation of X and Y Chromosome Bearing Spermatozoa Based on DNA Difference: a Review." Reprod. Fertil. Dev. 7:893-903. (1995).

Johnson, L.A., "Sex Preselection in Rabbits: Live Births from X and Y Sperm Separated by DNA and Cell Sorting", Biology of Reproduction 41, pp. 199-203 (1989).

Johnson, L.A., "Sex Preselection in Swine: Altered Sex Rations in Offspring Following Surgical Insemination of Flow Sorted X- and Y-Bearing Sperm", Reproduction in Domestic Animals, vol. 26, pp. 309-314 (1991).

Johnson, L.A., "Sex Preselection in Swine: Flow Cytometric Sorting of X- and Y- Chromosome Bearing Sperm to Produce Offspring", Boar Semen Preservation IV, p. 107-114. (2000).

Johnson, L.A., "Successful Gender Preselection in Farm Animals", Agricultural Biotechnology, p. 439-452. (1998).

Johnson, L.A., et al. "Sex Preselection: High-speed Flow Cytometric Sorting of X and Y Sperm for Maximum Efficiency", Therio. vol. 52, p. 1323-1341 (1999).

Johnson, L.A., et al., "Enhanced Flow Cytometric Sorting of Mammalian X and Y Sperm: High Speed sorting and Orienting Nozzle for Artificial Insemination", Therio. 49(1): 361 (1988) abstr.

Johnson, L.A., et al., "Flow Sorting of X and Y Chromosome-Bearing Spermatozoa into Two Populations", Gamete Res. 16:203-212. (1987).

Johnson, L.A., et al., "Improved Flow Sorting Resolution of X- and Y-Chromosome Bearing Viable Sperm Separation Using Dual Staining and Dead Cell Gating" Cytometry 17 (suppl 7): 83, (1994).

Johnson, L.A., et al., "Flow Cytometry of X- and Y-Chromosome Bearing Sperm for Dna Using an Improved Preparation Method and Staining with Hoechst 33342." Gamete Research 17: 203-212. (1987).

Johnson, L.A., et al., "Modification of a Laser-Based Flow Cytometer for High-Resolution DNA Analysis of Mammalian Spermatozoa" Cytometry 7, pp. 268-273 (1986).

Joseph, R. L. "Carcass composition and meat quality in once calved heifers." In: J.C. Taylor (Ed.) *The Early Calving of Heifers and its Impact on Beef Production*. 143. (1975).

Joseph, R. L. and J. P. Crowley. "Meat Quality of Once-Calved Heifers." Irish J. of Agric. Research 10:281. (1971).

Kachel, V., et al., "Uniform Lateral Orientation, Caused by Flow Forces, of Flat Particles in Flow-Through Systems", The Journal of Histochemistry and Cytochemistry, vol. 25, No. 7, pp. 774-780. (1997).

Kanayama, K., et al., "Pregnancy by Means of Tubal Insemination and Subsequent Spontaneous Pregnancy in Rabbits." J. Int. Med. Res. 20:401-405. (1992).

Karabinus, et al., "Effects of Egg Yolk-Citrate and Milk Extenders on Chromatin Structured Viability of Cryopreserved Bull Sperm", Journal of Dairy Science, vol. 74, No. 11, p. 3836-3848. (1999).

Keeling, P. "A Modeling Study of Once-Bred Heifer Beef Production." Proceedings of the New Zealand Society of Animal Production. 51. (1991).

Kilicarslan, M. R., et al., "Effect of GnRH and hCG on Ovulation and Pregnancy in Mares." Vet. Rec. 139:119-120. (1996).

Kinder, J. E., et al. "Endocrine Basis for Puberty in Heifers and Ewes." J. Repro. and Fertility, p. 393. (1995).

Kinder, J. E., et al., "Endocrine Regulation of Puberty in Cows and Ewes." J. Repro. and Fertility, Suppl. 34:167. (1987).

Kinoshita, Shuichi. "Spectroscopic Properties of Fluorescein in Living Lymphocytes," Osaka Uinversity Aug. 7, 1986.

Klindt, J. and J. D. Crouse. "Effect of Ovariectomy and Ovariectomy with Ovarian Autotransplantation on Feedlot Performance and Carcass Characteristics of Heifers." J. Anim. Sci. 68:3481. (1990).

Klosterman, E. W. and C. F. Parker. "Effect of Size, Breed and Sex Upon Feed Efficiency in Beef Cattle." North Central Regional Research Publication 235, Ohio Agric. Research and Development Center 1090:3. (1976).

Kniffen, D. M., et al., "Effects of Long-Term Estrogen Implants in Beef Heifers." J. Anim. Sci. 77:2886. (1999).

Kobata, Akira, "Structures and Functions of the Sugar Chains of Human Chorionic Gonadotropin", in *Glycoprotein Hormones* Chin, W.W. and Boime, I., eds. Serono Symposia, Norwell, MA. p. 19-20. 1990.

Koch, R. M., et al., "Characterization of Biological Types of Cattle -Cycle-II .3." Carcass Composition, Quality and Palatability. J. Anim. Sci. 49:448. (1919).

Kommisrud E., et al. "Comparison of Two Processing Systems for Bull Semen with Regard to Post-Thaw Motility and Nonreturn Rates." Theriogenology, vol. 45, 1996, pp. 1515-1521.

Lapin, D. R. and Ginther, O. J. "Induction of Ovulation and Multiple Ovulations in Seasonally Anovulatory and Ovulatory Mares with an Equine Pituitary Extract." J. Anim. Sci. 44:834-842. (1977).

Laster, D. B., "Factors Affecting Dystocia and Effects of Dystocia on Subsequent Reproduction in Beef-Cattle." J. Anim. Sci. 36:695. (1973).

Lawrenz, R. "Preliminary Results of Non-Surgical Intrauterine Insemination of Sheep With Thawed Frozen Semen." J S Afr. Vet. Assoc. 56(2): 61-63. (1985).

Levinson, G., et al., "DNA-based X-Enriched Sperm Separation as an Adjunct to Preimplantation Genetic Testing for the Preparation of X-linked Disease." Mol. Human Reprod. 10:979-982. (1995).

Lightwave Electronics, "Xcyte," www.LightwaveElecronics.com.

Lindsey, A. C., et al., "Low Dose Insemination of Mares Using Non-Sorted and Sex-Sorted Sperm" Animal Reproduction Science 68 p. 279-89 (2001).

Lindsey, A., et al., "Hysteroscopic Insemination of Mares with Nonfrozen Low-dose Unsexed or Sex-sorted Spermatozoa", pp. 1-15 currently unpublished.

Linge, F. "Faltforsok med djupfrost sperma (Field Trials With Frozen Sperm)." Farskotsel. 52:12-13. (1972).

Liu, Z, et al. "Survival of Bull Sperm Frozen at Different rates in Media Varying in Osmolarity." Cryobiology, vol. 27, 1998, pp. 219-230.

Lonergan, P., et al., "Effect of Time Interval from Insemination to First Cleavage on the Development of Bovine Embryos In Vitro and In Vivo", Therio. p. 326 (1999).

Long, C.R., et al., "In Vitro Production of Porcine Embryos From Semen Sorted for Sex With a High Speed Cell Sorter: Comparison of Two Fertilization Media." Therio. 49(1): 363 (1998) abstr.

Loy, R. G. and Hughes, J.P. "The Effects of Human Chorionic Gonadotropin on Ovulation, Length of Estrus, and Fertility in the Mare." Cornell Vet. 56:41-50 (1965).

Lu, K. H. et al., "In Vitro Fertilization of Bovine Oocytes with Flow-Cytometrically Sorted and Unsorted Sperm from Different Bulls" Therio. abstr.

Lu, K. H., et al., "In Vitro Fertilization with Flow-Cytometrically-Sorted Bovine Sperm", Therio 52, p. 1393-1405. (1999).

Lynch, I. M., et al., "Influence of timing of gain on growth and reproductive performance of beef replacement heifers." J. Anim. Sci. 75:1715. (1997).

Macmillan, K. L. and Day, A.M., "Prostaglandin F2a: A Fertility Drug in Dairy Cattle?", Animal Research Station, Private Bag, Hamilton, New Zealand, Therio. vol. 18, No. 3, p. 245-253 (1982).

Manni, Jeff. "To-Photon Excitation Expands the Capabilities of Laser-Scanning Microscopy,".

Manning, S.T., et al., "Development of Hysteroscopic Insemination of the Uterine Tube in the Mare", Proceedings of the Annual Meeting of the Society for Theriogenology, 1998, p. 84-85.

Martin, A. H., et al., "Characteristics of Youthful Beef Carcasses in Relation to Weight, Age and Sex. III. Meat Quality Attributes." Canadian J. Anim. Sci. 51:305. (1971).

Martin, L. C., et al., "Genetic-effects on Beef Heifer Puberty and Subsequent Reproduction." J. Anim. Sci. 70:4006. (1992).

Martinez, E. A., et al., "Successful Low-Dose Insemination by a Fiberoptic Endoscope Technique in the Sow", Proceedings Annual Conference of the International Embryo Transfer Society, Netherlands, Therio. vol. 53 p. 201, Jan. 2000.

Matsuda, Y. and Tobari, I. "Chromosomal Analysis in Mouse Eggs Fertilized In Vitro With Sperm Exposed to Ultraviolet Light (UV) and Methyl and Ethyl Methanesulfonate (MMS and EMS)." Mutat. Res. 198:131-144. (1988).

Matulis, R. J., "Growth and carcass characteristics of cull cows after different times-on-feed." J. Anim. Sci. 65:669. (1987).

Mauleon, P. "Recent research related to the physiology of puberty." In: J.C. Taylor (ed.) *The Early Calving of Heifers and its Impact on Beef Production.* (1975).

Maxwell, W. and Johnson, L., "Chlortetracycline Analysis of Boar Spermatozoa After Incubation, Flow Cytometric Sorting, Cooling, or Cryopreservation", Molecular Reproduction and Development 46, p. 408-418. (1997).

Maxwell, W. M. C., et al., "Fertility of Superovulated Ewes After Intrauterine or Oviductal Insemination with Low Numbers of Fresh or Frozen-Thawed Spermatozoa." Reprod. Fertil. Dev. 5:57-63. (1993).

Maxwell, W. M. C., et al., "The Relationship Between Membrane Status and Fertility of Boar Spermatozoa After Flow Cytometric Sorting in the Presence or Absence of Seminal Plasma" Reprod. Fertil. Dev. vol. 10 p. 433-40 (1998).

Maxwell, W. M. C., et al., "Viability and Membrane Integrity of Spermazota after Dilution and Flow Cytometric Sorting in the Presence or Absence of Seminal Plasma." Reprod. Fertil. Dev. 8:1165-78. (1997).

McCormick, R. J. "The Flexibility of the Collagen Compartment of Muscle." Meat Sci. 36:79. (1994).

McCue, P.M. "Superovulation" Vet. Clin. N. Amer. Eq. Prac. 12:1-11. (1996).

McCue, P.M., et al., "Oviductal insemination in the mare." 7th Internat. Symp. Eq. Reprod. 133 (1997) abstr.

McDonald, L. E. "Hormones of the Pituitary Gland." Veterinary Pharmacology and Therapeutics. 6th ed. Edited by N. H. Booth and L. E. McDonald. Ames, Iowa State Univ. Press. p. 590 (1988).

McKenna, T. et al., "Nonreturn Rates of Dairy Cattle Following Uterine Body or Cornual Insemination." J. Dairy Sci. 73:1179-1783 (1990).

McKinnon, A.O. and Voss, J. L. *Equine Reproduction.* Lea and Febiger. Philadelphia, London (1993).

McKinnon, A.O., et al., "Predictable Ovulation in Mares Treated With an Implant of the GnRH Analogue Deslorelin." Eq. Vet. J. 25:321-323. (1993).

McKinnon, A.O., et al., "Repeated Use of a GnRH Analogue Deslorelin (Ovuplant) for Hastening Ovulation in the Transitional Mare." Eq. Vet. J. 29:153-155. (1996).

McLeod, John H., "The Axicon: A New type of Optical Element", Journal of the Optical Society of America, vol. 44 No. 8, Aug. 1954, Eastman Kodak Company, Hawk-Eye Works, Rochester, New York.

McNutt, T. L. et al., "Flow Cytometric Sorting of Sperm: Influence on Fertilization and Embryo/Fetal Development in the Rabbit", Molecular Reproduction and Development, vol. 43, p. 261-267 (1996).

Meilgaard, M., et al., "Sensor Evaluation Techniques." CRC Press Inc., Boca Raton, FL. (1991).

Meinert, C., et al., "Advancing the Time of Ovulation in the Mare With a Short-Term Implant Releasing the GnRH Analogue Deslorelin", Equine Veterinary Journal, 25, p. 65-68 (1993).

Melamed et al, "An Historical Review of the Development of Flow Cytometers and Sorters", 1979, pp. 3-9.

Mendes Jr., J.O.B. "Effect of heparin on cleavage rates and embryo production with four bovine sperm prepration protocols" Theriogenology 60 (2003) 331-340.

Menke,E. A Volume Activated Cell Sorter Journal of Histo chemistry and Cyto Chemistry, 1977, vol. 25,No. 7, pp. 796-803.

Merton, J., et al., "Effect of Flow Cytometrically Sorted Frozen/Thawed Semen on Success Rate of In Vitro Bovine Embryo Production", Therio. 47, p. 295. (1997).

Metezeau P. et al. Improvement of Flow Cytometry Analysis and Sorting of Bull Spermatozoa by Optical Monitoring of Cell Orientation as Evaluated by DAN Specific Probing Molecular Reproduction and Development, 1991,vol. 30 pp. 250-257.

Meyers, P. J., et al., "Use of the GnRH Analogue, Deslorelin Acetate, in a Slow Release Implant to Accelerate Ovulation in Oestrous Mares." Vet. Rec. 140:249-252. (1997).

Michaels, C., "Beef A. I. Facilities That Work", Proc. Fifth N.A.A.B Tech. Conf. A. I. Reprod. Columbia, MO. pp. 20-22.

Michel, T. H., et al., "Efficacy of Human Chorionic Gonadotropin and Gonadotropin Releasing Hormone for Hastening Ovulation in Thoroughbred Mares." Eq. Vet. J. 6:438-442. (1986).

Miller, S. J. "Artificial Breeding Techniques in Sheep." Morrow, D.A. (ed): Current Therapy in Therio 2. Philadelphia, WB Saunders. (1986).

Mirskaja, L. M. and Petropavloskii, V.V. "The Reduction of Normal Duration of Heat in the Mare by the Administration of Prolan." Probl. Zivotn. Anim. Breed. Abstr. 5:387. (1937).

Moe, P. W., "Energetics of Body Tissue Mobilization." J. of Dairy Sci. 54:548.

Molinia, F. C., et al., "Successful Fertilization After Superovulation and Laparoscopic Intrauterine Insemination of the Brushtail Possum *Trichosurus vulpecula*, and Tammar Wallaby, *Macropus eugenii*." J. Reprod. Fertil. 112:9-17. (1998).

Moran, C., et al., "Puberty in Heifers -a Review." Animal Reproduction Sci. 18:167. (1989).

Moran, D. M. et al., "Determination of Temperature and Cooling Rate Which Induce Cold Shock in Stallion Spermatozoa", Therio. vol. 38 p. 999-1012 (1992).

Morcom, C. B. and Dukelow, W.R. "A Research Technique for the Oviductal Insemination of Pigs Using Laparoscopy." Lab. Anim. Sci. p. 1030-1031. (1980).

Morgan, J. B., et al., "National Beef Tenderness Survey." J. Anim. Sci. 69: 3274. (1991).

Morris, L. H., et al., "Hysteroscopic Insemination of Small Numbers of Spermatozoa at the Uterotubal Junction of Preovulatory Mares", Journal of Reproduction and Fertility, vol. 118, pp. 95-100 (2000).

Morris, S. T., et al., "Biological efficiency: How relevant is this concept to beef cows in a mixed livestock seasonal pasture supply context?" Proceedings of the New Zealand Society of Animal Production 54:333. (1994).

Moseley, W. M., et al., "Relationship of Growth and Puberty in Beef Heifers Fed Monensin" J. Anim. Sci. vol. 55 No. 2 p. 357-62 (1982).

Mount, D. E. "Fibrous and Non-fibrous Carbohydrate Supplementation to Ruminants Grazing Forage From Small Grain Crops." M.S. Thesis. Abstr. Colorado State University. (2000).

Muller, W. and Gautier, F. "Interactions of Heteroaromatic Compounds with Nucleic Acids." Euro. J Biochem. 54:358. (1975).

Mullis, K. B. and F. A. Faloona, "Specific Synthesis of DNA in Vitro Via a Polymerase-Catalyzed Chain Reaction" Methods in Enzymology vol. 155 p. 335-350 (1978).

Munne, S. "Flow Cytometry Separation of X and Y Spermatozoa Could be Detrimental to Human Embryos", Hum. Reprod. 9(5): 758 (1994).

Myers, S. E., "Performance and Carcass Traits of Early-Weaned Steers Receiving Either a Pasture Growing Period or a Finishing Diet at Weaning." J. Anim. Sci. 77:311. (1999).

Myers, S. E., et al., "Comparison of Three Weaning Ages on Cow-Calf Performance and Steer Carcass Traits." J. Anim. Sci. 77:323. (1999).

Myers, S. E., et al., "Production Systems Comparing Early Weaning to Normal Weaning With or Without Creep Feeding for Beef Steers." J. Anim. Sci. 77:300. (1999).

Nix, J. P., et al., "Serum Testosterone Concentration, Efficiency of Estrus Detection and Libido Expression in Androgenized Beef Cows." Therio. 49: 1195. (1998).

Nowshari, et al., "Superovulation of Goats with Purified pFSH Supplemented with Defined Amounts of pLH", Therio. vol. 43, p. 797-802 (1995).

Nrc. "Nutrient Requirements for Beef Cattle." National Academy of Sci. National Research Council, Washington, DC. (1996).

O'Brien, Justine K. et al., "Preliminary Developments of Sperm Sorting Technology in Non-human Primates", Biology of Reproduction 2001(Su;;I. 1) 64:158.

Olive, M.D., "Detection of Enterotoxigenic *Escherichia coli* after Polymerase Chain Reaction Amplification with a Tehrmostable DNA Polymerase", J of Clinical Microbiology, Feb. 1989 p. 261-265.

Olson, S.E. and Seidel, G. E. Jr., "Reduced Oxygen Tension and EDTA improve Bovine Zygote Development in a Chemically Defined Medium", J. of Anim. Sci. 78, pp. 152-157. (2000).

Owen, J. B. "The Maiden Female-A Means of Increasing Meat Production." Proc. Symp. On the Use of Once Bred Heifers and Gilts. (1973).

Ozhin F.V. et al. Artificial insemination of farm animals. Moscow, Izdatelstvo Selskohozyaastvennoi Literatury, 1961, pp. 350-361 and pp. 380-393.

Pace, M. M. and Sullivan, J. J. "Effect of Timing of Insemination, Numbers of Spermatozoa and Extender Components on Pregnancy Rates in Mares Inseminated with Frozen Stallion Semen." J. Reprod. Fertil. Suppl. 23:115-121.

Parrish, J. J., et al., "Capacitation of Bovine Sperm by Heparin", Department of Meat and Animal Science, Biology Of Reproduction 38, p. 1171-1180 (1988).

Patterson, D. J., et al., "Estrus Synchronization with an Oral Progestogen Prior to Superovulation of Postpartum Beef Cows" Therio. 48, 1025-33 (1997).

Peippo, J., et al., "Sex Diagnosis of Equine Preimplantation Embryos Using the Polymerase Chain Reaction", Therio. vol. 44:619-627 (1995).

Penfold, L.M.et at., "Comparative Motility of X and Y Chromosome-Bearing Bovine Sperm Separated on the Basis of Dna Content", Mol. Reprod. And Develop. 1998, vol. 50,pp. 323-327.

Perry, E. J., "Historical Background" The Artificial Insemination of Farm Animals. 4th ed. E. J. Perry (ed.) New Brunswick, Rutgers University Press, pp. 3-12. (1968).

Petersen, G. A., et al, "Cow and Calf Performance and Economic-Considerations of Early Weaning of Fall-Born Beef Claves", J. Anim. Sci., 64:15, pp. 15-22. (1987).

Petit, M. "Early Calving in Suckling Herds." In: J.C. Taylor (ed.) *The Early Calving of Heifers and its Impact on Beef Production*. p. 157-176. (1975).

Picket B.W., et al., "Livestock Production Science," 1998.

Pickett, B. W, et al., "Factors Influencing the Fertility of Stallion Spermatozoa in an A. I. Program." Proc. 8th International Congress Anim. Reprod. A. I. Krakow, Poland. 4:1049-1052. (1976).

Pickett, B. W., et al., "Effect of Seminal Extenders on Equine Fertility." J. Anim. Sci. 40:1136-1143. (1975).

Pickett, B. W., et al., "Influence of Seminal Additives and Packaging Systems on Fertility of Bovine Spermatozoa." J. Anim. Sci. Suppl. II. 47:12. (1978).

Pickett, B. W., et al., "Management of the Mare for Maximum Reproductive Efficiency." CSU Anim. Repro. Lab. Bull. No. 06. Fort Collins CO. (1989).

Pickett, B. W., et al., "Procedures for Preparation, Collection, Evaluation and Insemination of Stallion Semen." CSU Exp. Sta. Artira. Reprod. Lab. Gen. Series Bull. 935. (1973).

Pickett, B. W., et al., "Recent Developments in Artificial Insemination in Horses", Livestock Production Science, 40, p. 31-36 (1994).

Pickett, B. W., et al., "The Effect of Extenders, Spermatozoal Numbers and Rectal Palpation on Equine Fertility." Proc. Fifth N.A.A.B Tech. Conf. A. I. Reprod. Columbia, MO. pp. 20-22. (1974).

Pinkel et al., "Flow Chambers and Sample Handling", Flow Cytometry: Instrumentation and Data Analysis, Van Dilla et al. (Eds.), 1985, pp. 77-128.

Pinkel, D., et al, "Flow Cytometric Determination of the Proportions of X- and Y- Chromosome-Bearing Sperm in Samples of Purportedly Separated Bull Sperm", J. of Anim. Sci., vol. 60, p. 1303-1307 (1998).

Pinkel, D., et al., "High Resolution DNA Content Measurements of Mammalian Sperm", Cytometry 3:1-9. (1982).

Pinkel, D., et al., "Sex Preselection in Mammals? Separation of Sperm Bearing the Y and "O" Chromosomes in the Vole Microtus Oregoni", Science vol. 218 p. 904 (1982).

Piston, D.W. "Three-dimensionally resolved NAD(P)H cellular metabolic redox imaging of the in situ cornea with two-photon excitation laser scanning microscopy," Journal of Microscopy, vol. 178, Nov. 29, 1994.

Polge, E. J., "Historical Perspective of AI: Commercial Methods of Producing Sex Specific Semen, IVF Procedures", Proceedings of the 16th Technical Conference on Artificial Insemination & Reproduction, Cambridge, England, pp. 7-11. (1996).

Polge, et al, "Revival of Spermatozoa After Vitrification and Dehydration at Low Temperatures," Nature, 164:666 (1994).

Preza, C. et al, "Determination of Direction-Independent Optical Path-Length Distribution of Cells Using Rotational-Diversity Transmitted-Light Differential Interference Contrast (DIC) Images", Presented at the Multidimensional Microscopy: Image Acquisition and Processing V, p. 1-11 (1998).

Prokofiev M.I. Regoulyatsia Razmnozhenia Selskokhozyastvennykh Zhivotnykh, Leningrad, Naouka Publishing House, 1983, pp. 181-195.

Province, C.A., et al., Cooling Rates, Storage, Temperatures and Fertility of Extended Equine Spermatozoa Therio. vol. 23 (6) p. 925-934, Jun. 1985.

Pursel, et al, "Effect of Orvus ES Paste on Acrosome Morphology, Motility and Fertilizing Capacity of Frozen-Thawed Boar Sperm," Journal of Animal Science, 47:1:198-202 (1978).

Purvis, H. T. and J. C. Whittier. "Effects of Ionophore Feeding and Anthelmintic Administration on Age and Weight at Puberty in Spring-Born Beef Heifers." J. Anim. Sci. 74:736-744. (1996).

Randel, R. D. "Nutrition and Postpartum Rebreeding in Cattle." J. Anim. Sci. 68:853. (1990).

Rath, D., et al., "Low Dose Insemination Technique in the Pig", Boar Semen Preservation IV, p. 115 118. (2000).

Rath, D., et al., "Production of Piglets Preselected for Sex Following in Vitro Fertilization with X and Y Chromosome-Bearing Spermatozoa Sorted by Flow Cytometry", Therio. 47, p. 795-800 (1997).

Rathi, R. et al., "Evaluation of In Vitro Capacitation of Stallion Spermatoza", Biology of Reproduction 2001,vol. 65, pp. 462-470.

Recktenwald, Diether. "Cell Separation Methods and Applications," New York 1997.

Reiling, B.A., et al., "Effect of Prenatal Androgenization on Performance, Location, and Carcass and Sensory Traits on Heifers in Single Calf Heifer System", J. Anim. Sci., 1995, 73: 986, p. 986-992.

Reiling, B.A., et al., "Effects of Prenatal Androgenization and Lactation on Adipose Tissue Metabolism in Finishing Single-Calf Heifers" J. Anim. Sci. vol. 75 p. 1504-1512 (1997).

Reiling, B.A., et al., "Effects of prenatal Androgenization, Melengestrol Acetate, and Synovex-H on Feedlot Performance, Carcass, and Sensory Traits of Once-Calved Heifers" J. Anim. Sci. vol. 74 p. 2043-51 (199).

Rens, W., et al., "A Novel Nozzle for More Efficient Sperm Orientation to Improve Sorting Efficiency of X and Y Chromosome-Bearing Sperm", Technical Notes, Cytometry 33, p. 476-481 (1998).

Rens, W., et al., "Improved Flow Cytometric Sorting of X- and Y-Chromosome Bearing Sperm: Substantial Increase in Yield of Sexed Semen", Molecular Reproduction and Development, p. 50-56(1999).

Rieger, D., et al, "The Relationship Between the Time of First Cleavage of Fertilized Cattle Oocytes and Their Development to the Blastocyst Stage", Therio. 1999, p. 190.

Rigby, S. L., et al., "Pregnancy Rates in Mares Following Hysterscopic or Rectally-Guided Utero-Tubal insemination with Low Sperm Numbers" Abstracts/Animal Reproduction Science vol. 68 p. 331-333 (2001).

Riggs, B.A. "Integration of Early Weaning and Use of Sexed Semen in a Single-Calf Heifer System to Increase Value of Non-Replacement Heifers" MS Thesis, Colorado State University, Spring 2000.

Ritar, A. and Ball, A., "Fertility of Young Cashmere Goats After Laparoscopic Insemination." J. Agr. Sci. 117: p. 271-273. (1991).

Roberts, J. R., Veterinary Obstetrics and Genital Diseases. Ithaca, New York. p. 740-749. (1971).

Romero-Arredondo, A. "Effects of Bovine Folicular Fluid on Maturation of Bovine Oocytes" Theriogenology 41: 383-394, 1994.

Romero-Arrendondo, A. "Effects of Follicular Fluid dring In Virto Maturation of Bovine Oocytes on In Vitro Fertilization and Early Embryonic Development" Biology of Reproduction 55, 1012-1016 1996.

Romita, A. "Some Considerations on the Beef Situation in Italy." In: J.C. Taylor (ed.) The Early Calving of Heifers and its Impact on Beef Production. 23. (1975).

Roser, J. F., et al., "Reproductive Efficiency in Mares With Anti-hCG Antibodies." Proc 9th Int. Congr. Anim. Repro. and A. I. 4:627 (1980) abstr.

Roth, T. L., et al., "Effects of Equine Chorionic Gonadotropin, Human Chorionic Gonadotropin, and Laparoscopic Artificial Insemination on Embryo, Endocrine, and Luteal Characteristics in the Domestic Cat." Bio. Reprod. 57:165-171 (1997).

Roux, M., et al., "Early Calving Heifers Versus Maiden Heifers for Beef-Production from Dairy herds. I. The Effects of Genotype (Friesian and Carloads x Friesian) and Two Feeding Levels in the Rearing Period on Growth and Carcass Quality." Livestock Prod. Sci. 16:1 (1987).

Rowley, H. S., et al., "Effect of Insemination Volume on Embryo Recovery in Mares." J. Equine Vet. Sci. 10:298-300 (1990).

Roy, J. H., "Rearing Dairy-Herd Replacements." Journal of the Society of Dairy Technology 31:7379 (1978).

Rutter, L. M., et al., "Effect of Abomasal Infusion of Propionate on the GnRH-Induced Luteinizing Hormone Release in Prepuberal Heifers." J. Anim. Sci. 56:1167 (1983).

Salamon, S., Artificial Insemination of Sheep, Chippendale, New South Whales. Publicity Press. p. 83-84 (1976).

Salisbury, G. W. and VanDemark, N. L. "Physiology of Reproduction and Artificial Insemination of Cattle." San Francisco: Freeman and Company. p. 442-551 (1978) (1961 & 1978 Combined) Chapters 16 and 17 are the complete article.

Schenk, J. L. "Applying Semen Sexing Technology to the AI Industry", Proceedings of the 18th Technical Conference on Artificial insemination & Reproduction, 2000.

Schenk, J. L, et al., "Imminent Commercialization of Sexed Bovine Sperm", Proceedings, The Range Beef Cow Symposium XVL, p. 89-96 (1999).

Schenk, J. L., "Cryopreservation of Flow-Sorted Bovine Spermatozoa", Therio. vol. 52, 1375-1391 (1999).

Schiewe, M. C., et al., "Transferable Embryo Recovery Rates Following Different Insemination Schedules in Superovulated Beef Cattle" Therio. 28 (4) Oct. 1997, pp. 395-406.

Schillo, K. K., et al, "Effects of Nutrition and Season on the Onset of Puberty in the Beef Heifer." J. Anim. Sci. 70:3994 (1992).

Schmid, R. L., et al, "Fertilization with Sexed Equine Spermatozoa Using Intracytoplasmic Sperm Injection and Oviductal Insemination ", 7th International Symposium on Equine Reproduction, pp. 139 (1998) abstr.

Schnell, T. D., et al, "Performance, Carcass, and Palatability Traits for Cull Cows Fed High-Energy Concentrate Diets for 0, 14, 28, 42, or 56 days." J. Anim. Sci. 75:1195. (1997).

Schoonmaker, J. P., et al., "Effects of Age at Weaning and Implant Strategy on Growth of Steer Calves." J. Anim. Sci. (Suppl. II) 76:71. (1998) abstr.

Seidel, G. E. Jr. "Cryopreservation of Equine Embryos" Veterinary Cliniics of North America: Equine Practice vol. 12, No. 1, Apr. 1996.

Seidel, G. E. Jr. "Sexing Bovine Sperm" The AABP Proceedings—vol. 34.

Seidel, G. E. Jr. Sexing mammalian spermatozoa and embryos-state of the art Journal of Reproduction and Fertility Supp 54, 477-487 1999.

Seidel, G. E. Jr. "Uterine Horn Insemination of Heifers With Very Low Nos. Of Nonfrozen and Sexed Spermatozoa", Atlantic Breeders Cooperative, Therio. 48: pp. 1255-1264, (1997).

Seidel, G. E. Jr et al., "Current Status of Sexing Mammalian Spermatozoa," Society for Reproduction and fertiity, pp. 733-743, 2002.

Seidel, G. E. Jr., "Commercilizing Repreductive Biotechnology—The Approach used by XY, Inc.," Theriogenology, p. 5, 1999.

Seidel, G. E. Jr. et al., "Insemination of Heifers with Sexed Sperm", Therio, vol. 52, pp. 1407-1421 (1999).

Seidel, G. E. Jr., "Use of Sexed Bovine Sperm for In Vitro Fertilization and Superovulation", Animal Reproduction and Biotech Lab, CSU, Proceedings of the 2000 CETA/ACTE Convention, Charlottetown, Prince Edward Island, Aug. 2000, pp. 22-24.

Seidel, G. E. Jr., "Artificial Insemination With X-and Y-Bearing Bovine Sperm", Animal Reproduction and Biotechnology Laboratory, Colorado State University, (1996).

Seidel, G. E. Jr., "Status of Sexing Semen for Beef Cattle", Texas A & M University 45th Annual Beef Cattle Short Course and Trade Show Proceedings, Aug. 9-11, p. III24-III27, (1999).

Seidel, G. E. Jr., et al, "Insemination of Heifers With Very Low Numbers Of Frozen Spermatozoa", CSU, Atlantic Breeders Cooperative, Lancaster, PA, DUO Dairy, Loveland, CO, Jul. 1996.

Seidel, G. E. Jr., et al, "Insemination of Holstein Heifers With Very Low Numbers of Unfrozen Spermatozoa", CSU, Atlantic Breeders Cooperative, (1995).

Seidel, G. E. Jr., et al, "Sexing Mammalian Sperm—Overview", Therio. 52: 1267-1272, (1999).

Seidel, G. E. Jr., et al., "Artificial Insemination of Heifers with Cooled, Unfrozen Sexed Semen", Therio, vol. 49 pp. 365 (1998) abstr.

Seidel, G. E. Jr., et al., "Insemination of Heifers with Sexed Frozen or Sexed Liquid Semen." Therio. 51. (in press) (1999) abstr.

Seidel, G. E. Jr., Economics of Selecting for Sex: The Most Important Genetic Trait, Theriogenology 59, (2003), pp. 585-598.

Sell, R. S., et al., "Single-calf Heifer Profitability Compared to Other North Dakota Beef Production Systems." Department of Ag. Eco., North Dakota State University, Ag. Econ. Rpt. 20.

Senger, P. L., et al., "Influence of Cornual Insemination on Conception in Dairy Cattle." J Anim. Sci. 66:3010-3016. (1988).

Shabpareh, V. "Methods for Collecting and Maturing Equine Oocytes in Vitro" Theriogenology 40: 1161-1175, 1993.

Shackelford, S. D., et al, "Effects of Slaughter Age on Meat Tenderness and USDA Carcass Maturity Scores of Beef Females." J. Anim. Sci. 73:3304. (1995).

Shapiro, Howard M. MD., PC. "Practical Flow Cytometry Third Edition," New York 1994.

Sharpe, J.C., et al., "A New Optical Configuration for Flow Cytometric Sorting of Aspherical Cells" Horticulture and Food Research Institute of New Zealand Ltd., Hamilton, New Zealand (PNS) Nov. 2, 1997 Abstract.

Sharpe, Johnathan, Thesis; "An Introduction of Flow Cytometry", Ch. 2-2.2, 1997.

Sharpe, Johnathan, Thesis; "Gender Preselection-Principle Scientific Options," Ch. 3.4-3.4.8, 1997.

Sharpe, Johnathan, Thesis; "Sperm Sexing using Flow Cytometry," Ch. 3.5-3.5.8, 1997.

Sharpe, Johnathan, Thesis; "Sperm Sexing-Method of Johnson et al," Ch. 3.6-4.3.4, 1997.

Shelton, J. N. and Moore, N.W. "The Response of the Ewe to Pregnant Serum Mare Gonadotropin and to Horse Anterior Pituitary Extract." J. Reprod. Fertil. 14:175-177. (1967).

Shilova, A. V., et al., "The Use of Human Chorionic Gonadotropin for Ovulation Date Regulation in Mares." VIIIth Int. Congress On Anim. Repro. and A. I. 204-208. (1976).

Shorthose, W. R. and P. V. Harris. "Effect of Animal Age on the Tenderness of Selected Beef Muscles." J. Food Sci. 55:1-. (1990).

Silbermann, M., "Hormones and Cartilage. Cartilage: Development, Differentiation, and Growth." pp. 327-368. Academic Press, Inc. (1983).

Simon, M., "The Effect of Management Option on the Performance of Pregnant Feedlot Heifers." M.S. Thesis. Kansas State University. (1983).

Skogen-Hagenson, M. J. et al; "A High Efficiency Flow Cytometer," The Journal of Histochemistry and Cytochemistry, vol. 25, No. 7, pp. 784-789, 1977, USA.

Smith, G. C., et al, "USDA Maturity Indexes and Palatability of Beef Rib Steaks." J. of Food Quality 11:1. (1988).

Smith, G. C., et al., "Relationship of USDA Maturity Groups to Palatability of Cooked Beef." J. of Food Sci. 47:1100. (1982).

Smith, R. L., et al, Influence of Percent Egg Yolk during Cooling and Freezing on Survival of Bovine Spermatozoa, Dairy Science 1979 J 62:1297-1303.

Solsberry G.U., Van-Denmark N.L., Theory and practice of artificial cow insemination in USA, Moscow, KOLOS Publishing House, 1966, p. 346.

Spectra Physics, The Solid State Laser Company, "Vangaurd 4 Watts of UV from a Quasi-CW, All Solid State Laser," http://www.splasers.com/products/isl_products/vangaurd.html three pages, printed Nov. 14, 2002.

Spectra-Physics Products, "Fcbar" http://www.splasers.com/products/oem_products/ov_fcbar.html two pages printed Nov. 14, 2002.

Spectra-Physics, The Solid State Laser Company, Vanguard 2000-HMD 532, www.specra-physics.com.

Spectra-Physics, The Solid State Laser Company, Vanguard 350-HMD 355, www.specra-physics.com.

Squires, E. L, et al., "Effect of Dose of GnRH Analog on Ovulation in Mares." Therio. 41:757-769. (1994).

Squires, E. L., "Simultaneous Analysis of Multiple Sperm Attributes by Flow Cytometry", Diagnostic Techniques and Assisted Reproductive Technology, The Veterinary Clinics of North America, Equine Practice, vol. 12, No. 1, p. 127-130 (1996).

Squires, E. L., "Early Embryonic Loss" *Equine Diagnostic Ultrasonography*, first ed., Rantanen & McKinnon. Williams and Wilkins, Baltimore, Maryland, p. 157-163 (1998).

Squires, E. L., et al, "Cooled and Frozen Stallion Semen", Bulletin No. 9, Colorado State University, Ft. Collins, CO. (1999).

Squires, E.L., "Procedures for Handling Frozen Equine Semen for Maximum Reproductive Efficiency", pp. 1, 39-41, 81-89.

Staigmiller, R.B. "Superovulation of Cattle with Equine Pituitary Extract and Porcine FSH" Theriogenology 37: 1091-1099 1992.

Stap J. et al Improving the Resolution of Cryopreserved X- and Y-Sperm During DNA Flow Cytometric Analysis with the Addition of Percoll to quench the Fluorescence of Dead Sperm: Academic Medical Center, University of Amsterdam (1998) Journal of Animal Science vol. 76 1998, pp. 1896-1902.

Steel, N. L., "Cost Effectiveness of Utilizing Sexed-Semen in a Commercial Beef Cow Operation", MS Thesis, Colorado State University, Summer 1998.

Steinkamp: "Flow Cytometry" vol. 55, No. 9, Sep. 1984 pp. 1375-1400, New York Review of Scientific Instruments Abstract Only.

Stellflug, J. N., "Plasma Estrogens in Periparturient Cow." Therio 10:269. (1978).

Stevenson, J. S., et al., "Detection of Estrus by Visual Observation and Radiotelemetry in Peripubertal, Estrus-Synchronized Beef Heifers." J. Anim. Sci. 74:729. (1996).

Story, C. E., et al., "Age of Calf at Weaning of Spring-Calving Beef Cows and the Effect on Cow and Calf Performance and Production Economics." J. Anim. Sci. 78:1403. (2000).

Stovel R.T. A Means for Orienting Flat Cells in flow systems Biophysical Journal, 1978,vol. 23,pp. 1-5.

Sullivan, J. J., et al., "Duration of Estrus and Ovulation Time in Nonlactating Mares Given Human Chorionic Gonadotropin During Three Successive Estrous Periods." J.A.V.M.A. 162:895-898. (1973).

Sumner, A. T. and Robinson, J. A., "A Difference in Dry Mass Between the Heads of X and Y-Bearing Human Spermatozoa", J Reprod Fertil. 48, p. 9-15 (1976).

Swanson, E. W. "Future Research on Problems of Increasing Meat Production by Early Calving." In: J.C. Taylor (ed.) *The Early Calving of Heifers and its Impact on Beef Production*. (1975).

Swenson, S. L., et al., "PRRS Virus Infection in Boars: Isolation From Semen and Effect on Semen Quality" from the 1995 Research Investment Report, Iowa State University, Veterinary Clinical Sciences, Iowa State University.

Taljaard, T. L., et al., "The Effect of the Laparoscopic Insemination Technique on the Oestrus Cycle of the Ewe." J. South Afr. Vet. Assoc. 62(2): 60-61. (1991).

Tatum, J. D., et al., "Carcass Characteristics, Time on Feed and Cooked Beef Palatability Attributes." J. Anim. Sci. 50:833. (1980).

Taylor, C. S., "Efficiency of Food Utilization in Traditional and Sex-Controlled Systems of Beef Production", AFRC Animal Breeding Research Organization, West Mains Road, Edinburg EH9 3JQ, pp. 401-440.

Tervit, H.R., et al., "Successful Culture In Vitro of Sheep and Cattle Ova", Agricultural Research Council, Unit of Reprod. Physio. and Biochem., Univ of Cambridge, p. 493-497 (1972).

Thun, Rico, et al., Comparison of Biociphos-Plus® and TRIS-Egg Yolk Extender for Cryopreservation of Bull Semen; Theriogenology Symposium, Dec. 1999, vol. 52, #8.

Time-Bandwidth Products "GE—100—XHP", www.tbsp.com, 2 pages, Jan. 2002.

Unruh, J. A. "Effects of Endogenous and Exogenous Growth-Promoting Compounds on Carcass Composition, Meat Quality and Meat Nutritional-Value." J. Anim. Sci. 62:1441. (1986).

USDA "Official United States Standards for Grades of Carcass Beef." Agric, Marketing Serv., USDA, Washington, DC. (1997).

Van Dilla, Martin, "Overview of Flow Cytometry: Instrumentation and Data Analysis", Flow Cytometry: Instrumentation and Data Analysis, Van Dilla et al. (Eds.), 1985, pp. 1-8.

van Munster, E. B., "Geslachtsbepaling met interferometrie", Derde prijs NtvN-prijsvraag voor pas-gepromoveerden 65/4, (Sex Determination with Interferometry) p. 95-98 (1999).

van Munster, E. B., et al, "Difference in Sperm Head Volume as a Theoretical Basis for Sorting X & Y-Bearing Spermatozoa: Potentials and Limitations", Therio 52, pp. 1281-1293 (1999).

van Munster, E. B., et al, "Difference in Volume of X- and Y-chromosome Bearing Bovine Sperm Heads Matches Difference in DNA Content" Cytometry vol. 35 p. 125-128 (1999).

van Munster, E. B., et al, "Measurement-Based Evaluation of Optical Path Length Distributions Reconstructed From Simulated Differential Interference Contrast Images", J of Microscopy 191, Pt. 2, p. 170-176 (1998).

van Munster, E. B., et al, "Reconstruction of Optical Pathlength Distributions From Images Obtained by a Wide Field Differential Interference Contrast Microscope", J of Microscopy 188, Pt. 2, p. 149-157 (1997).

Vazquez, J. J. et al., "Nonsurgical Uterotubal Insemination in the Mare", Proceedings of the 44th Annual Convention of the American Association of Equine Practitioners, vol. 44, pp. 68-69 (1998).

Vazquez, J. M., et al., "A. I. In Swine; New Strategy for Deep Insemination with Low Number of Spermatozoa Using a Non-surgical Methodology", 14th International Congress on Animal Reproduction, vol. 2, Stockholm, Jul. 2000, p. 289.

Vazquez, J., et al., "Development of a Non-surgical Deep Intra Uterine Insemination Technique", Boar Semen Preservation IV, IVth International Conference on Boar Semen Preservation, Maryland, pp. 262-263.

Vazquez, J., et al., "Hyposmotic Swelling Test as Predictor of the Membrane Integrity in Boar Spermatozoa", Boar Semen Preservation IV, IVth International Conference on Boar Semen Preservation, Maryland, pp. 263.

Vazquez, J., et al., "Successful low dose insemination by a fiber optic Endoscope technique in the Sow", Proceedings Annual Conference of the International Embryo Transfer Society, Netherlands, Theriogenology, vol. 53 Jan. 2000.

Vidament, M., et al., "Equine Frozen Semen Freezability and Fertility Field Results." Therio. 48:907. (1997).

Vincent, B.C., et al, "Carcass Characteristics and Meat Quality of Once-Calved Heifers." Canadian J. Anim. Sci. 71:311. (1991).

Vogel, T., et al, "Organization and Expression of Bovine TSPY", Mammalian Genome, vol. 8, pp. 491-496 (1997).

Voss, J. L. and Pickett, B. W., "Reproductive Management of the Broodmare." CSU Exp. Sta. Anim. Reprod. Lab. Gen. Series. Bull. 961. (1976).

Voss, J. L., et al., "Effect of Number and Frequency of Inseminations on Fertility in Mares." J. Reprod. Fertil. Suppl. 32:53-57. (1982).

Voss, J. L., et al., Effect of Human Chorionic Gonadotropin on Duration of Estrous Cycle and Fertility of Normally Cycling, Nonlactating Mares. J.A.V.M.A. 165:704-706. (1974).

Waggoner, A. W., et al., "Performance, Carcass, Cartilage Calcium, Sensory and Collagen Traits of Longissimus Muscles of Open Versus 30-month-old Heifers That Produced One Calf." J. Anim. Sci. 68:2380. 1990.

Watson, "Recent Developments and Concepts in the Cryopreservvation of Spermatozoa and the Assessment of Their Post-Thawing Function," Reprod. Fertil. Dev. 7:871-891 (1995) Abstract.

Welch G., et al., Fluidic and Optical Modifications to a FACS IV for Flow Sorting of X- and Y-Chromosome Bearing Sperm Based on DNA. Cytometry 17 (Suppl. 7): 74. (1994).

Welch, G., et al., "Flow Cytometric Sperm Sorting and PCR to Confirm Separation of X- and Y-Chromosome Bearing Bovine Sperm", Animal Biotechnology, 6, pp. 131-139 (1995).

Wheeler, T. L., et al., "Effect of Marbling Degree on Beef Palatability in Bos-taurus and Bos-indicus cattle." J. Anim. Sci. 72:3145. (1994).

Wickersham, E. W. and L. H. Schultz. "Influence of Age at First Breeding on Growth, Reproduction, and Production of Well-Fed Holstein Heifers." J. Dairy Sci. 46:544. (1963).

Wilhelm, K.M. et al, "Effects of Phosphatidylserine and Cholesterol Liposomes on the Viability, Motility, and Acrosomal Integrity of Stallion Spermatozoa Prior to and after Cryopreservation", Cryobiology 33:320, 1996.

Wilson, C. G., et al., "Effects of Repeated hCG Injections on Reproductive Efficiency in Mares." Eq. Vet. Sci. 4:301-308. (1990).

Wilson, D. E. et al., "Mammal Species of the World", Smithsonian Institution Press, 1993, 1206 pp.

Wilson, M.S. "Non-surgical Intrauterine Artificial Insemination in Bitches Using Frozen Semen." J. Reprod. Fertil. Suppl. 47:307-311. (1993).

Windsor, D. P., et al, "Sex Predetermination by Separation of X and Y Chromosome-bearing Sperm: A Review", Reproduction of Fertilization and Development 5, pp. 155-171, (1993).

Wintzer et al.:"Krankheiten des Pferdes Ein Leitfaden fur Studium and Praxiz," 1982, nParey, Berlin Hamburg XP002281450.

Woods, G. L. and Ginther, O. J. "Recent Studies Related to the Collection of Multiple Embryos in Mares." Therio. 19:101-108. (1983).

Woods, J., et al., "Effects of Time of Insemination Relative to Ovulation on Pregnancy Rate and Embryonic-Loss Rate in Mares." Eq. Vet. J. 22(6): 410-415. (1990).

Zhou, Hongwei, et al. "Research on and Development of Flow Cell Sorting Apparatuses," Gazette of Biophysics, vol. 13, ed. 3, 1997.

Hamamatsu, "Photomultiplier Tubes," web page, http://www.optics.org/hamamatsu/pmt.html. Printed on Apr. 15, 2000 4.

Hermesmeyer, G.N. ,et al. Effects of Lactation and Prenatal Androgenization on the Performance, Carcass Composition, and Longissimus muscle sensory characteristics of heifers in the single-calf heifer system. The Professional Animal Scientist 15: 14-23.

Seidel, G. E. Jr., "Fertility of Bulls on the Edge of the Dose-Response Curve for Numbers of Sperm per Inseminate"; Proceedings of the 17th Technical comference on Artificial Insemination & Reproduction, 1998.

Hollinshead, F.K. et al. "In vitro and in vivo assessment of functional capacity of flow cytometrically sorted ram spermatozoa after freezing and thawing." Reprod. Fertil. And Develop. 2003. vol. 15, pp. 351-359.

Hollinshead F. K. et al. "Production of lambs of predetermined sex after the insemination of ewes with low Nos. Of frozen-thawed sorted X- or Y- Chromosome-bearing spermatozoa", Reprod. Fertil. And Develop. 2002, vol. 14, pp. 503-508.

Hollinshead F. K. et al. "Sex-Sorting and Re-cryopreservation of Frozen-Thawed Ram Sperm for In Vitro Embryo Production" Theriogenology , vol. 59. (2003) pp. 209.

Dhali et al. Vitrification of Buffalo (Bubalus Bubalis)Oocytes, Embryo Theriogenology vol. 53, pp. 1295-1303 (2000).

Borini et al. Cryopreservation of Mature Oocytes: The use of a trypsin inhibitor enhances fertilization and obtained embryos rates, Fertil. Steril. (1997), vol. 68 (Suppl.).

Hamamatsu Photonics K.K. Electronic Tube Center, Photomultiplier Tubes, Brochure Dec. 1997.

Johnson, L. A., et al. The Beltsville Sperm Sexing Technology: High-speed sperm sorting gives improved sperm output for in Vitro fertiliation and AI, Journal of Animal Science,vol. 77, Suppl 2/J, Dairy Sci. vol. 82, Suppl. Feb. 1999 pp. 213-220.

Peters D., The LLNL high-speed sorter: Design features,operational characteristics, and bioloical utility, Cyometry, 6:290-301 (1985).

Rens W., et al Slit-scan flow cytometry for consistent high resdolution DNA analysis of X- and Y- chromosome bearing sperm, Cytometry 25:191-199 (1996).

van Munster, E. B. Interferometry in flor to sort unstained X- and Y-Chromosome-Bearing Bull Spermatozoa, Cytometry 47:192-199 (2002).

Scmid, R. L., et al. Effects of follicular fluid or progesterone on in vitro maturation of equine oocytes before intracytoplasmic sperm injection with non-sorted and sex-sorted spermatozoa, Journal of Reproduction and Fertility 56:519-525, 2000.

Brink, Z et al. A reliable procedure for superovulating cattle to obtain zygotes and early emryos for microinjection, Theriogenology vol. 41, p. 168, (1994).

Spectra-Physics, The Solid State Laser Company, Vanguard 350-HMD 355, User's Manual, Dec. 2002.

Photon, Inc. Light MeasuringSolutions, NanoScan for High-powered beam Applications, 2005.

Fluorescense Lifetime Systems, www.picoquant.com, Jan. 28, 2005 pp. 2.

NCI ETI Branch, Flow CytometryCore Laboratory, http://home.ncifcrf.gov/ccr/flowcore/ndyag.htm, pp. 5, May 11, 2004.

NCI ETI Branch, Flow CytometryCore Laboratory, http://home.ncifcrf.gov/ccr/flowcore/IsrII.htm, pp. 14, May 11, 2004.

Saacke,R.G., Can Spermatozoa with abnormal heads gain access to the ovum in artificially inseminated super- and single-ovulating cattle?, Theriogenology 50:117-128. 1998.

Hawk, H.W., Gamete Transport in the Superovulated Cow: Theriogenology: Jan. 1998 vol. 29 No. 1 pp. 125-142.

Blecher, S.R., et al. A new approach to immunological sexing of sperm, Theriogenology, 59, pp. 1309-1321, 1999 Vol.

Wheeler, M. B., et al. Application of sexed semen technology to in vitro embryo production in cattle, Theriogenology, vol. 65 (2006) 219-227.

Garverick, H. A., et al. mRNA and protein expression of P450 aromatase (AROM) and estrigen receptors (ER) α and β during early development of bovine fetal ovaries; The society for the study of reproduction 38th annual meeting Jul. 24-27, 2005; Abstract only.

Bodmer, M., et al., Fertility in heifers and cows after low does insemination with sex-sorted and non-sorted sperm under field conditions; Theriogenology, vol. 64, (2005) 1647-1655.

Schenk J. L., et al. Embryo production from superovulated cattle following insemination of sexed sperm, Theriogenology, 65 (2006) 299-307.

Garner, D. L., Flow cytometric sexing of mammalian sperm, Theriogenology, 65 (2006) 943-957.

Habermann F. A., et al., Validation of sperm sexing in the cattle (Bos taurus) by dual colour flourescence in situ hybridization; J Anim Breed Genet. Apr. 2005; 122 Suppl 1:22-7 (Abstract only).

Johnson, L. A., Sexing mammalian sperm for production of offspring: the state-of-the-art; Animal Reproduction Science; 60-61 (2000) pp. 93-107.

Seidel, G.E. Jr., et al., Methods of Ovum Recovery and Factors Affecting Fertilization of Superovulated Bovine Ova, Control of Reproduction in the Cow, Sneenan ed., 1978, pp. 268-280.

Hawk, H. W. et al., Effect of Unilateral Cornual Insemination upon Fertilization Rate in Superovulating and Single-Ovulating Cattle, Journal of Animal Sciences, 1986 vol. 63, pp. 551-560.

Andersson, M. et al., Pregnancy Rates in Lactating Holstein-Greisian Cows after Artificial Insemination with Sexed Sperm. Reprod. Dom. Anim 41, 95-97, 2006.

Morton, K. M., et al., In vitro and in vivo survival of bisected sheep embryos derived from frozen-thawed unsorted, and frozen-thawed sex-sorted and refrozen-thawed ram spermatozoa; Theriogenology, 65 (2006) 1333-1345.

Wilson, R. D., et al., In vitro production of bovine embryos using sex-sorted sperm, Theriogenology, 65 (2006) 1007-1015.

Johnson, L.A., et al, 1996 Gender preselection in mammals. XX Beltsville Symposium in Agricultural Research Technolgy's Role in the Genetic Improvement of Farm Animals. pp. 151-164, Amer. Soc. Anim. Sci. IL, USA.

Smorag, Z., et al., Cattle Sex Regulation by Separation of X and Y Spermatozoa—Preliminary Results of Field Experiment in Poland, Reproduction, Fertility and Development 17(2) 306-306; Jan. 1, 2005.

Crichton, E., et al. (Abstract) Artificial Insemination of Lactating Holstein Cows with Sexed Sperm, Reproduction, Fertility and Development 18(2) 281-281, Dec. 14, 2005.

Lindsey, A.C., et al. Hysteroscopic insemination of low Nos. Of flow sorted fresh and frozen/thawed stallion spermatozoa, Equine Vet J. Mar. 2002;34(2):106-7.

Drobnis, E. Z, Cold shock damage is due to lipid phase transitions in cell membranes : a demonstration using sperm as a model, Journal of experimental zoology (J. exp. zool.) 1993, vol. 265, No. 4, pp. 432-437 (22 ref.).

Hagele, W.C., et al., Effect of Separating Bull Semen into X and Y Chromosome-bearing Fractions on the Sex Ratio of Resulting Embryos; Cran J. Comp. Med, 1984: 48:294-298.

U.S. Appl. No. 11/422,735, filed May 25, 2006 entitled Apparatus, Methods and Processes for Sorting Particles and for Providing Sex-Sorted Animal Sperm.

Suh, T.K, et al., Pressure during flow sorting of bull sperm affects post-thaw motility characteristics; Theriogenology vol. 59, No. 1, Jan. 2003 p. 516.

Rath, D, et al., In Vitro Production of Sexed Embryos for Gender Preselection: High-speed sorting of X-Chromosome-Bearing Sperm to Produce Pigs After Embryo Transfer, J. Anim. Sci. 1999, 77:3346-3352.

Auchtung, T.L., et al., Effects of Photoperiod During the Dry Period on Prolactin, Prolactin Receptor, and Milk Production of Dairy Cows; Journal of Dairy Sci. 88: 121-127; American Dairy Sci. Assoc., 2005.

Bailey, T. et al., Milk Production Evaluation in First Lactation Heifers; 1999 Virginia Cooperation Extension/Dairy Science Publication 404-285.

Belloin, J.C., Milk and Dairy products: prduction and processing costs Food and Agriculture Organization of United Nations Rome 1988 FAO; web page where found: www.fao.org/docrep/003/x6931e/X6931E00.htm.

Kume, Shin-ichi; Dept of Animal Nutrition National Institute of Animal Industry Tsukuba 305, Japan the Dairy Industry $IN Asia B. Japan; www.agnet.org/library/article/eb384b.html.

Crichton,E. et al., 347 Artificial Insemination of Lactating Holstein Cows with sexed sperm: Abstract CSORP Publishing—Reproduction, Fertility and Development www.publish.csiro.au/nid/44/paper/RDv18n2Ab347.htm.

Lopez, H. et al., Relationship Between Level of Milk Production and Multiple Ovulation in Lactating Dairy Cows Journal of Dairy Sci. 88:2783-2793; American Dairy Science Association, 2005.

Managing the Dairy Cow During the Dry Period; Dairy Cattle Production 341-450A; Macdonald Campus of McGill University/Faculty of Agricultural & Environmental Sciences/Department of Animal Science.

Milk Production and Biosynthesis University of Guelph/Dairy Science and Technology www.foodsci.uoguelph.ca/dairyedu/biosyntheses.html.

Milk Production, Released Jul. 18, 2006, by the National Agricultural Statistics Service (Mass), Agri. Stats. Board, US Dept of Agri.

DeVries, A. Economic Value of Pregnancy in Dairy Cattle Journal of Dairy Sci. 89:3876-3885/American Dairy Sci. Assoc. 2006.

Garner, D.L. et al., Viability Assessment of Mammalian Sperm Using SYBR-14 and Propidium Lodide, 1996, Biology of Reproduction, vol. 53, pp. 276-284.

Salisbury, G.W. et al., Substrate-Free Epididymal-Like Bovine Spermatozoa, J Repord Fertil, 1963, vol. 6, pp. 351-359.

Wong, P.Y.D., et al. Potassium Movement During sodium-Induced Motility Initiation in the Rat Caudal Epididymal Spermatozoa; Biology of Reproduction 28, 206-212 (1983).

Shirai, H., et al. Regulation of Sperm Motility in Starfish; Development, Growth, and Differentiation; 24, (5), 419-428 (1982).

Padilla, A.W. et al. Extender and Centrifugation Effects on the Motility Patterns of Slow-Cooled Stallion Spermatozoa; J. Anim. Sci 1991, 69:3308-3313.

Ohta H., et al., Acquisition and Loss of Potential for Motility Ofspermatozoa of the Japanese Eel Anguilla Japonica, National Research Institute of Aquaculture, Nansei, Mie.

Morisawa, M. The Process of the Initiation of Sperm Motility; Laboratory of Physiology, Ocean Research Institute, University of Tokyo.

McGrady, A.V., et al. Cholinergic Effects on Bull and Chimpanzee Sperm Motility; Biology of Reproduction 15, 248-253 (1976).

Klinc, P. Dissertation—Improved Fertility of Flowcytometrically Sex Selected Bull Spermatozoa, School of Veterinary Medicine Hanover Germany, 2005.

Jones, J.M. et al Acidification of Intracellular pH in Bovine Spermatozoa Suppresses Motility and Extends Viable Life, Journal of Andrology, vol. 21, No. 5, September/October 616-624.

Jenkins, A. D., et al. Concentrations of Seven Elements in the Intraluminal Fluids of the Rat Seminiferous Tubules, ReteTestis, and Epididymis; Biology of Reproduction 23, 981-987 (1980).

Darszon, A., et al. Ion Channels in Sperm Physiology, Physiological Reviews, vol. 27, No. 2, Apr. 1999.

Christen, R., et al. Metabolism of Sea Urchin Sperm, the Journal of Biological Chemistry, vol. 25, No. 9, Issue of May 10, pp.

Babcock, D. F., et al. Potassium-dependent increases in cytosolic pH stimulate metabolism and motility of mammalian sperm, Proc. Natl. Acad. Sci. USA, vol. 80, pp. 1327-1331, Mar. 1983.

Zilli, L., et al. Adenosine Triphosphate Concentration and β-D-Glucuron idase Activity as Indicators of Sea Bass Semen Quality; Biology of Reproduction 70,1679-1684 (2004) Published online before print Feb. 11, 2004.

Hanania, E. G, et al. A novel Automated Method of Scanning Cytometry and Laser-Induced Necrosis Applied to Tumor Cell Purging, Blood. Nov. 15, 1999, vol. 94, No. 10, suppl 1 part 1.

Parallel Korean Application 10-2002-7006696; Notice of Grounds for Refusal dated Oct. 30, 2006.

U.S. Appl. No. 10/266,562, filed Oct. 7, 2002.

Pursley, J.R. et al., Reproductive Management of Lactating Dairy Cows Using Synchronization of Ovulation; 1997 J. Dairy Sci 80:301-306.

Bagnato, A., Genetic and Breeding; Phenotypic Evaluation of Fertility Traits and Their Association with Milk Production of Italian Friesian Cattle; 1994 J. Dairy Sci 77:874-882.

Panskowski, J., A., et al. Use of Prostaglandin F2a as a Postpartum Reproductive Management Tool for Lactating Dairy Cows; 1995 J. Dairy Sci 78:1477-1488.

Scipioni, R. L., et al., Short Communication: An Electronic Probe Versus Milk Protesterone as Aids for Reproductive Management of Small Dairy Herds; 1999 J. Dairy Sci 82:1742-1745.

Fricke, P. M., Scanning the Fugure—Ultrasonography as a Reproductive Management Tool for Dairy Cattle; J. Dairy Sci 85:1918-1926.

Grant, V. J., et al., Sex-Sorted Sperm and Fertility: An Alternative View; Biology of Reproduction 76, 184-188 (2007).

Garner, D. L., Sex-Sorting Mamallian Sperm: Concept to Application in Aminals; Journal of Andrology, vol. 22, No. 4 Jul./Aug. 2001.

Tubman, L.M. et al., Characteristics of calves produced with sperm sexed by flow cytometry/cell sorting; 2004 Amer. Society of Animal Sciences; 82:1029-1036.

Weigel, K. A., Exploring the Role of Sexed Semen in Dairy Production Systems; J. Dairy Sci. 87: (E.Suppl.): E120-E130; 2004 American Dairy Science Assoc.

Ferre, L., et al., In vitro-derived embryo production with sexed and unsexed semen from different bulls; Reproduction Fertility and Development, vol. 16, Part 1/2, p. 253, 2004.

Dalton, J.C., et al., Effect of Time of Insemination on Number of Accessory Sperm, Fetilization Rate, and Embryo Quality in Nonlactating Dairy Cattle. J Dairy Sci. 84:2413-2418.

Dransfield, M.B.G., et al., Timing of Inseminatio for Dairy Cows Identified in Estrus by a Radiotelemetric Etrus Detection System. 1998 J Dairy Sci. 81: 1874-1882.

Maatje, K. et al. Predicting Optimal Time of Insemination in Cows that Show Visual Signs of Estrus by Estimating onset of Estrus with Pedometers.

Nebel, R.L. et al. Timing of Artificial Insemination of Dairy Cows: Fixed Time Once Daily Versus Morning and Afternoon 1994 J Dairy Sci. 77:3185-3191.

Pursley, J. Richard, et al. Effect of Time of Artificial Insemination on Pregnancy Rates, Calving Rates, Pregnancy Loss, and Gender Ratio After Synchronization of Ovulation in Lactating Dairy Cows. 1998 J Dairy Sci. 81: 2139-2144.

Rozeboom, K. J. et al. Late Estrus or Metestrus Insemination After Estrual Inseminations Decreases Farrowing Rate and Litter Size in Swine J. Animal Sci. 1997. 75: 2323-2327.

Peeler, I. D. et al. Pregnancy Rates After Times Al of Heifers Following Removal of Intravaginal Progesterone Inserts, J. Dair Sci., 87:2868-2873; 2004.

Rath, D. Low Dose Insemination in the Sow—A Review, Reprod. Dom Anim. 37, 201-205 (2002) www.blackwell.de/synergy.

Lukaszewicz, M. et al. Attempts on freezing the Greylag (Anser anser L.) gander semen Animal Reproduction Science 80 (2004) 163-173.

Foote, R. H. et al. Sperm Numbers Inseminated in Dairy Cattle and Nonreturn Rates Revisited 1997 J Dairy Science 80:3072-3076.

Conely, H.H. et at. Intensification by Intrauterine Devices of Sperm Loss from the Sheep Uterus Biology of Reproduction 2, 401-407 (1970).

Chrenek, Peter et al. Fertilizing Capacity of Transgenic and Non-Transgenic Rabbit Spermatozoa after Heterospermic Insemination Bull Vet. Inst. Pulawy 49, 307-310, 2005.

Bakst, Murray R. Fate of Fluorescent Stained Sperm following Insemination: New Light on Ovicucal Sperm Transport and Storage in the Turkey.

Johnson L.A., et al. use of boar spermatozoa for artificial insemination, II. Fertilization Capacity of fresh and frozen spermatozoa in gilts inseminated either at a fixed time or according to walsmeta readings, Journal of Animal Science, vol. 54 No. 1, 1982 pp. 126-131.

Pursel, V. G., et al. Distribution and morphology of fresh and frozen-thawed sperm in the reproductive tract of gilts after artificial insemination; Biology of Reproduction 19, 69-76 (1978).

Purdy, P. H. et al., Effect of Adding Cholesterol to Bull Sperm Membranes on Sperm Capacitation, the Acrosome Reaction, and Fertility, Biology of Reproduction 71, 522-527 (2004).

Purdy, P. H. et al., Effect of cholesterol-loaded cyclodextrin on the cryosurvival of bull sperm, Cryobiology 48 (2004) 36-45.

Moce E., et al., Cholesterol-loaded cyclodextrins added to fresh bull ejaculates improve sperm cryosurvival, J. Anim. Sci, 2006, 84:826-833.

Ereth, B.A., et al. Integration of Early Weaning and Sexed Semen into a Single-Calf Heifer System to Increase Value of Non-Replacement Heifers; Proceedings, Western Section, American Society of Animal Science, vol. 51,441-443, Jun. 2000.

Ereth, B.A., et al. Integration of Early Weaning and Sexed Semen into a Single-Calf Heifer System to Increase Value of Non-Replacement Heifers; Abstract Only, Journal of Animal Science, vol. 78, Supplement 2, 2000.

Bavister, B.D. et al., The effects of Sperm Extracts and Energy Sources on the Motility and Acromosome Reaction of hamster Spermatozoa in vitero; Biology of Reproduction 16, 228-237 (1997).

Fattouh, El-S.M. et al., Effect of Caffine on the Post-Thaw Motility of Buffalo Spermatozoa; Theriogenology, Jul. 1991, vol. 36 No. 1.

Koh-ichi Hamano, et al., Gender Preselection in Cattle with Intracytoplasmically injected, flow cytometrically sorted sperm heads, Biology of Reproduction 60, 1194-1197 (1990).

Hollinshead, F.K. et al., Birth of lambs of pre-determined sex after in vitro production of embryos using frozen-thawed sex-sorted and re-frozen-thawed ram spermatozoa, Reproduction (Cambridge, England) May 2004, vol. 127, o. 5, pp. 557-568.

Nikkei Biotech, Supplement, Latest Information of Biological Instruments and Reagents, 1988, pp. 93-94.

U.S. Appl. No. 11/092,509, response to Restriction filed Jun. 12, 2006.

U.S. Appl. No. 11/092,509, OA mailed Jul. 21, 2006.

U.S. Appl. No. 11/092,338, Response to restriction filed Jan. 16, 2007.

U.S. Appl. No. 11/092,509, Resonse to OA filed Dec. 21, 2006.

U.S. Appl. No. 11/092,509, FOA dated Mar. 26, 2007.

U.S. Appl. No. 11/092,338, Non-Final Office action mailed May 18, 2007.

Pyruvate Stain—U.S. Appl. No. 11/092,509, Response to NonFinal OA dated Jul. 10, 2007.

U.S. Appl. No. 11/092,509, Advisory Action dated Sep. 13, 2007 & Notice of Appeal w Pre-Appeal Conf Request dated Sep. 26, 2007.

U.S. Appl. No. 11/092,338, Response to OA filed Oct. 18, 2007.

U.S. Appl. No. 11/092,509, Pre-Appeal Conf Decision dated Nov. 21, 2007.

Parallel Application, New Zealand Patent Application No. 530441, Response to Office Action, dated Jul. 19, 2005, 4 pages.

Parallel Application, Korea Patent Application No. 10-2002-7006696, Decision for Patent Grant and Certificate of Patent dated Jul. 25, 2007 and Sep. 5, 2007, 6 pages.

Parallel Application, Israel Patent Application No. 149802, Notification of Defects in Patent Application, dated May 3, 2007, 2 pages.

Parallel Application, Chinese Patent Application No. 00818617.0, English Translation of the Second Office Action, dated Dec. 12, 2006, 2 pages.

Parallel Application, Chinese Patent Application No. 00818617.0, English Translation of the Third Office Action, dated Jul. 6, 2007, 1 page.

Parallel Application, Chinese Patent Application No. 00818617.0, Decision of Granting Patent Right for Invention, 1 page.
Parallel Application, Australia Patent Application No. 2005239755, Examiner's first report, dated Aug. 24, 2007, 2 pages.
Parallel Application, Australia Patent Application No. 2005203165, Examiner's first report, dated Feb. 21, 2007, 2 pages.
Parallel Application, New Zealand Patent Application No. 552281, Examination Report, dated Jan. 5, 2007, 2 pages.
Parallel Application, New Zealand Patent Application No. 530441, Notice of Acceptance of Complete Specification, dated Sep. 5, 2005 and Letters Patent Certificate dated Jan. 12, 2006, 2 pages.
Parallel Application, European Patent No. 1257168, Summons to attend oral proceedings, dated Jun. 20, 2007, 4 pages.
Parallel Application, European Patent No. 1257168, Proprietor's Submissions, dated Nov. 30, 2007, 96 pages.
Parallel Application, European Patent No. 1257168, Response to Oppositions, dated Aug. 8, 2006, 10 pages.
Parallel Application, European Patent No. 1257168, English translation of Greenpeace Opposition, dated Oct. 31, 2005, 4 pages.
Parallel Application, European Patent No. 1257168, English translation of European Parliament Opposition, dated Nov. 2, 2005, 8 pages.
Parallel Application, European Patent No. 1257168, Comment in the name of Hiltrud Breyer dated Nov. 29, 2007, German and English translation (20 pages).
Grossfield, R., "Experiments to Improve the Quality of Sex-Sorted Fresh and Frozen Porcine Spermatozoa", PhD Thesis of the Faculty of Agricultural Sciences, Georg-August-Universitat, Gottingen.
Rath, D. "On the Status of Gender-Specific Sperm Sorting", Review lecture ET Conference 2002, Department of Animal Production and Animal Behavior, Mariensee.
Parallel Isreal Patent No. 149802; Office Action dated Mar. 2, 2008.
Parallel Australia Aplication No. 200503165; Office Action dated Feb. 14, 2008.
Parallel Australia Aplication No. 2005239755; Office Action dated Aug. 24, 2007.
de Graaf, S.P. et al., Birth of offspring of pre-determined sex after artificial insemination of frozen-thawed, sex-sorted and re-frozen-thawed ram spermatozoa, Theriogenology, 67 (2007) 391-398.
O'Brien, J.K. et al., Development fo sperm sexing and associated assisted reproductive technology for sex preselection of captive bottlenose dolphins, Reproduction Fertility and Development, 2006, 18, 319-329.
Zhang, M, et al., In vitro fertilization with flow-sorted buffalo sperm, Reproduction Fertility and Development, 2005, 18(2), 283-284.
Schenk, J.L. et al., Insemination of cow elk with sexed frozen semen, 2003 Theriogenology 59, 514.
BD Biosciences Brochure, BD FACSCalibur Flow Cytometer, the Automated, Multicolor Flow Cytometry System, 2006.
Johnson, L. A. et al., Cryopreservation of flow cytometrically sorted boar sperm: effects on in vivo embryo developmen; J. Anim Sci. vol. 78, Suppl 1/J. Dairy Sci., vol. 83, Suppl 1, 2000.
Lindsey, A., et al., "Hysteroscopic Insemination of Fresh and Frozen Unsexed and Sexed Equine Spermatozoa", pp. 152-153, Proc. 5th Int. Symp. Equine Embryo Transfer, p. 13, 2000.
Presicce, G.A., et al., First established pregnancies in mediterranean italian buffaloes (bubalus bubalis) following deposition of sexed spermatozoa near the utero tubal junction, Reproduction in Domestic Animals, vol. 40, No. 1, Feb. 2005 , pp. 73-75(3).
Dielemann, S.J., Superovulation in cattle: from understanding the biological mechanisms to genomics of the oocyte; $23^{rd}$ Annual Meeting A.E.T.E.—Alghero; Sep. 2007.
Hasler, J. F., Factors influencing the success of embryo transfer in cattle; $23^{rd}$ World Buiatrics Congress, Quebec, Canada Jul. 2004.
Mapletoft, R. J. et al., Superovulation in perspective, Bioniche Animal Health, Dec. 2002.
Bahr, G.F. et al., Considerations of volume, mass, DNA, and arrangement of mitochondria in the midpiece of bull spermatozoa, Experimental Cell Research 60 (1970) 338-340.
Baumber, J., et al., "The Effect of Reactive Oxygen Species on Equine Sperm Motility, Viability, Acrosomal Integrity, Mitochondrial Membrane Potential, and Membrane Lipid Peroxidation", 2000, Journal of Andrology, vol. 21 (6),pp. 895-902.

BD LSR II Flow Cytometer, BD Biosciences Clontech Discovery labware Immunocytometry systems Pharmingen Jan. 28, 2004.
Bermudez, D.et al., The immediate effect of IR, laser radiation on rat, germ, cells, was studied by cytophotometric quantification, Scisearch 2001.
Sequent Biotechnologies Inc., Welcome to the Sequent Biotechnologies Inc. website., http://www.sequentbiotech.com/ Dec. 6, 2003.
Sabuer K. et al."Effects of Angiotensin II on the Acrosome Reaction in Equine Spermatozoa" Journal of Reproduction and Fertility vol. 120, 2002 p. 135-142.
Brooks, D.E., Manipulation of Mammalian Gametes in Vitro, Biennial Report, Waite Agricultural Research Institute 1986-1989.
Bruemmer, J.E. et al., "Effect of Pyruvate on the Function of Stallion Spermatozoa Stored for up to 48 Hours", Journal of Animal Science 2002, vol. 80*1, pp. 12-18.
Catt, S.L. et al., Hoechst staining and exposure to UV laser during flow cytometric sorting does not affect the frequency of detected endogenous DNA nicks in abnormal and normal human spermatozoa, Molecular Human Reproduction vol. 3 No. 9 pp. 821-825,(1997).
Chaudhry, P., et al., Casein Kinase II activity and polyamine-stimulated protein phosphorylation of cytosolic and plasma membrane protiens in bovine sperm, Archives of Biochemistry and Biophyeics vol. 271, No. 1 pp. 98-106, May 15, 1989.
Chen, Y. et al., Effects of sucrose, trehalose, hypotaurine, taurine, and blood serum on survival of frozen bull sperm, Cryobiology 30,423-431 (1993).
Chapter 16 Semen processing, storage, thawing, and handling, http://nongae.gsnu.ac.kr/~cspark/teaching/chap16.html Sep. 23, 2002.
Conover,J. et al., Pre-loading of mouse oocytes with DNA-specific fluorochrome (Hoechst 33342) permits rapid detection of sperm-oocyte fusion, Journals of Reproductive & Fertility Ltd. 82, 681-690 (1988).
Cressman, B.E. MD, et al., Effect of sperm dose on pregnancy rate from intrauterine insemination: a retrospective analysis, Texas Medicine, 92:74-79 (1996).
Crissman, H.A. et al., Use of DIO-C5-3 to improve hoechst 33342 uptake, resolution of DNA content, and survival of CHO cells, Experimental cell research 174: 338-396 (1988).
Graves, C.N., et al., "Metabolism of Pyruvate by Epididymal-Like Bovine Spermatozoa", 1964 Journal of Dairy Science vol. 47 (12), pp. 1407-1411.
Certified Semen Services, CSS Minimum requirements for disease control of semen produced for AI, http://www.naab-css.org/about_css/disease_control-2002.html Sep. 22, 2003.
Culling, "Handbook of Histopathological and Histochemical Techniques, " 3rd Ed., Butterworths, pp. 192.
De Grooth, B. et al., Simple delay monitor for droplet sorters, Cytometry 12:469-472 (1991).
Lodge, J.R., et al., "Carbon Dioxide in Anaerobic Spermatozoan Metabolism" 1968, Journal of Dairy Science, vol. 51(1), pp. 96-103.
Delgado,N. et al., Correlation between sperm membrane destabilization by heparin and aniline blue staining as membrane integrity index, Archives of Andrology40:147-152 (1998).
Denniston, D.J. et al., "Effect of Antioxidants on the Motility and Viability of Cooled Stallion Spermatozoa", Journal Reproduction Supplement 56, 2001, pp. 121-126.
De Pauw M.C. et al. Sperm Binding to Epithelial Oviduct Explants in Bulls with Different Nonreturn Rates Investigated with a new In-Vitro Model Biology of Reproduction, 2002, vol. 67 p. 1073-1079.
Donoghue, A. et al., Effects of water- and lipid-soluble antioxidants on turkey sperm viability, membrane integrity, and motility during liquid storage, Poultry Science 76:1440-1445 (1997).
Durack, Gary; "Cell—Sorting Technology", Emerging Tools for Single-cell Analysis, Chapter 1 pp. 1-359.
Zucker, R. et al., Utility of light scatter in the Morphological analysis of sperm, Cytometry 13:39-47 (1992).
Ericsson, S. et al., Interrelationships among fluorometric analyses of spermatozoal function, classical semen quality parameters and the fertility of frozen-thawed bovine spermatozoal, Theriogenology 39:1009-1024 (1993).

Ericsson, et al. "Flow Cytometric Evaluation of Cryopreserved Bovine Spermatozoa Processed Using a New Antiobiotic Combination", Theriogenology, 1990, vol. 33(6), pp. 1211-1220.

Cho, et al. A microfluidic device for separating motile sperm from nomotile sprem via inter-streamline crossings.

Ericsson, R. et al., Functional differences between sperm bearing the X- or Y-chromosome.

Esteves, S. et al., Improvement in motion characteristics and acrosome status in cryopreserved human spermatozoa by swim-up processing before freezing, Human Reproduction vol. 15 No. 10 pp. 2173-2179 (2000).

Evenson, D.et al., Physiology and Management, Rapid determination on sperm cell concentration in bovine semen by flow cytometry, J Dairy Sci. 76: 86-94 (1993).

Farrell et al., "Quantification of Bull Sperm Characteristics measured by Computer-Assisted Sperm Analysis (CASA) and the Relationship of Fertility", Theriogenology, 1998, vol. 49 (4), pp. 871-879.

Fitzgerald, D., Cell sorting: An enriching Experience, The Scientist Jul. 23, 2001.

Foote,R., The history of artificial insemination: Selected notes and notables, American Society of Animal Science (2002).

Foote, R., Functional differences between sperm bearing the X- or Y-chromosome.

Garner, D., Past, Present and future perspectives on sexing sperm, CSAS Symposium SCSA: 67-78.

Johnson, L. et al., Sex preselection in mammals by DNA: A method for flow separation of X and Y Spermatozoa in humans.

Johnson, L. et al., Recent advances in sex preselection of cattle: Flow cytometric sorting of X-&Y-chromosome bearing sperm based on DNA to produce progeny, Theriogenology 41:51-56 (1994).

Ashwood-Smith, M., Debate Human sperm sex selection, Human Reproduction vol. 9 No. 5 pp. 757-759 ( 1994).

Pinkel,D.et al.,Flow cytometry of mammalian sperm progress in DNA and morphology measurement, The Journal of Histochemical and Cytochemistryvol. 27 No. 1 pp. 353-358 (1979).

Fugger, E. et al., Birth of normal daughters after MicroSort sperm separation and intrauterine insemination, in-vitro fertilization, or intracytoplasmic sperm injection, http://www.microsort.net/HumRepro.htm Mar. 19, 2003.

Johnson, L. et al., Flow sorting of X and Y Chromosome-bearing Mammalian sperm: Activation and pronuclear development of sorted bull, boar, and ram sperm microinjected into hamster oocytes, Gamete Research 21:335-343 (1988).

Salisbury, G.W., et al., Reversal by Metabolic Regulators of $CO_2$-induced Inhibition of Mammalian Spermatozoa, 1959, Proc Soc Exp Biology Med, vol. 101 (1) pp. 187-189.

Centola, G.et al., Cryopreservation of human semen. Comparison of cryopreservatives, sources of variability, and prediction of post-thaw survival. PMID: 1601749 May-Jun. 1992.

Bencic, D.C., et al., "Carbon Dioxide Reversibly Inhibits Sperm Motility and Fertilizing Ability in Steelhead (Oncorhynchus mykiss)" 2000, Fish Physiology and Biochemistry, vol. 23(4), pp. 275-281.

Boatman, D.E. et al., "Bicarbonate Carbon Dioxide Regulation of Sperm Capacitation Hyperactivated Motility and Acrosome Reactions", 1991, Biology of Reproduction vol. 44(5), pp. 806-813.

Garcia, M.A. et al., "Development of a Buffer System for Dialysis of Bovine Spermatozoa Before Freezing III.Effect of Different Inorganic and Organic Salts on Fresh and Frozen-Thawed Semen", 1989, Theriogenology, vol. 31(5),pp. 1039-1048.

Courtens, J. et al., Numerical simulation for freezing and thawing mammalian spermatozoa. Evaluation of cell injuries at different depths in bags or straws during all steps of the technique.

Eiman, M.et al., Trehalose-enhanced fluidity of the goat sperm membrane and its protection during freezing, Biology of Reproduction 69: 1245-1250 (2003).

Foote, R.et al., Physiology and Management, Fertility of bull spermatozoa frozen in whole milk extender with trehalose, taurine, or blood serum, J. Dairy Sci. 76:1908-1913 (1993).

Johnson, L. et al., Storage of bull semen, Animal Reproduction Science 62: 143-172 (2000).

Johnson, L. et al.,Erratum to "Storage of bull semen", Animal Reproduction Science 62: 143-172 (2000).

McNutt,T.et al., Electrophoretic gel analysis of Hoechst 33342 stained and flow cytometrically sorted bovine sperm membrane proteins, Reprod. Dom Anim.31: 703-709 (1996).

Van der Werf, Julius, An overview of animal breeding programs; Animal Breeding Use of New Technologies (This is a Post Graduate Foundation Publication).

Best, T. P. et al. "Nuclear Localization of Pyrrole-Imidazole Ployamide-Flourescein Conjugates in Cell Culture", PNAS, 2003, vol. 100(21), pp. 12063-12068.

Gygi, M.P., et al. "Use of Fluorescent Sequence-Specific Polyamides to Discriminate Human Chromosomes by Microscopy and Flow Cytometry", Nuci Acids Res. 2002, vol. 30(13),pp. 2790-2799.

Young, L.et al., Prolonged feeding of low levels of zearalenone to young boars.

BD Biosciences, BD AccuDrop Potion, www.bdbiosciences.com, Sep. 2002.

Agarwal, A.et al., Filtration of spermatozoa through L4 membrane:a new method, Fertility and Sterility, vol. 6, No. 6, Dec. 1991.

Anzar, M.et al., Optimizing and Quantifing fusion of liposomes to mammalian sperm using resonance energy transfer and flow cytometric methods, Cytometry49:22-27 (2002).

Anzar, M.et al., Sperm Apoptosis in fresh and cryopreserved bull semen detected by flow cytometry and it's relationship with fertility, Biology of Reproduction 66: 354-360 (2002).

Arav, A.et al., New trends in gamete's cryopreservation, Molecular and Cellular Endocrinology 187:77-81 (2002).

Arndt-Jovin et al., "Analysis and Sorting of Living Cells According to Deoxyribonucleic Acid Content", Journal Histochem. And Cytochem., 1977, vol. 25(7), pp. 585-589.

Arts,E.et al.,Evidence for the existence of lipid-diffusion barriers in the equatorial segment of human spermatozoa, Boichem J.384:211-218 (1994).

Garner,D.et al., Spermatozoa and Seminal Plasma, Reproduction in farm animals 7th edition.

Gadella B,et al., Dynamics in the membrain organization of the mammalian sperm cell and functionality in fertilization, Vet Quart. 21:142-146 (1999).

Garner, D.et al., Chromatin stability in sex-sorted sperm, VII International Congress of Andrology.

Garner,D. et al., Morphological and ultrastrutural Characterization of mammalian spermatozoa processed for flow cytometric DNA analyses, Gamete Research 10:339-351 (1984).

Garner, D., et al., Effect of hoechst 33342 staining and laser illumination on the viability of sex-sorted bovine sperm, Theriogenology, vol. 57 No. 1, 1-810 (2002).

Garner, D. et al., Assessment of spermatozoal function using dual fluorescent staining and flow cytometric analyses, Biology of Reproduction 34:, 127-138 (1986).

Gebhard D., Sorting Viability . . . one more time, http://www.cyto.purdue.edu/hmarchiv/1998/2263.htm Feb. 14, 2004.

Givan,A., Flow Cytometry First Principles, (1992).

Gledhill, B.et al., Identifying and separating X- and Y- Chromosome-bearing mammalian sperm by flow cytometry, Lawrence Livermore National Laboratory, Feb. 8, 1984.

Gledhill, B.et al., Identifing X- and Y- chromosome- bearing sperm by DNA content:Retrospective perspectives and prospective opinions'.

Gledhill, B.et al., Flow microflurometric analysis of sperm DNA contemt: Effect of cell shape on the fluorescence distribution, J. Cell Physiol.87: 367-378.

Gledhill, B.et al., Flow cytometry and sorting of sperm and male germ cells, Flow Cytometry and sorting, second edition, pp. 531-551 (1990).

Gordon et al., " Genetic Transformation of Mouse Embryos by Microinjection of Purified DNA", Proc. Natil Acad. Sci., 1980, vol. 77 (12), pp. 7380-7384.

Graham, J.et al.,Analysis of sperm cell viability, Acrosomal integrity, and Mitocondrial function using flow cytometry, Biology of Reproduction 43: 55-64 (1990).

Graham, J.et al., Effect of some Zwitter Ion buffers on freezing and storage of spermatozoa I, Bull, J. Dairy Sci 55: 372-378 ( 1992).

Grogan, W. et al., DNA Analysis and sorting of viable mouse testis cells, The Journal of Histochemistry and Cytochemistry, vol. 29 No. 6 pp. 738-746, (1981).

Guthrie, et al., "Flow Cytometric Sperm Sorting: Effects of Varying laser Power on Embryo Development in Swine", Mol. Reprod. And Develop., 2002,vol. 61 (1), pp. 87-92.

Hacker-Klom, U.B., et al., Effect of doxorubicin and 4'-epi-doxorubicin on mouse spermatogenesis. Mutation Research International Journal on Mutagenesis vol. 159, pp. 39-46. 1986.

Hargrove, T. et al., Special Techniques, Part B Cryopreservation, Chapter 11B.

Hasler, J., Symposium: Reproductive Technology and Genetic improvementJ. Dairy Sci. 75:2857-2879 (1992).

Held, A.et al., Quasi- CW Solid- state lasers Expand their reach, Photonics Spectra, Dec. 2002.

Hinkley, R.et al., Rapid visual detection of sperm-egg fusion using the DNA-Specific Fluorochrome Hoechst 33342, Developmental Biology 118: 148-154 (1986).

Januskauskas, A.et al.,Assessment of sperm quality through Fluorometry and sperm chromatin structure assay in relation to field fertility of frozen-thawed semen from Swedish AI bulls, Theriogenology 55: 947-961 (2001).

Janendran, R.et al., Effect of glycerol and cryopreservation on oocyte penetration by human spermatozoa, PMID: 4025843, Jul. 6, 2006.

Johnson, L., A flow cytometric/ sorting method for sexing mammalian sperm validated by DNA analysis and live births, Cytometry, p. 42 of supplement , Sep. 4, 1990.

Johnson, L., Flow sorting of intact X & Y chromosome-bearingmammalian spermatozoa, The Journal of the Society for Analytical Cytology Cytometry, (1988).

Zhang,M. et al., Development of bovine embryos after in vitro fertilzation of oocytes with a flow cytometrically sorted, stained and unsorted sperm from different bulls, Theriogenology 60: 1657-1663 (2003).

Jones,R.et al., Effect of Osmolality and Phosphate, "Tris", "Tes", "Mes", nd "Herpes" Hydrogen ion buffers on the motility of bull spermatozoa stored at 37 or 5°C, Ausi J. Biol. Sci.25:1047-1055 (1972).

Jones,R., Plasma membrane structures and remodelling during sperm maturation in the epididymis, Journal of Reproduction and Fertility (1998).

Gerrits, Roger J. Application of Biotechnology to Animal Production US Dept. of Agriculture, Beltsville Maryland.

Johnson, L., Separation of X and Y Chromosome-bearing mammalian sperm by DNA content cytometric analysis and sorting, US Department of Agriculture.

Johnson, M.,The Macromolecular Organization of membranes and its bearing on events leading up to Fertilization, Journal of Reproduction and Fertility (1975).

Johnson, L., Verified Sex Pre-Selection in Farm Animals.

Johnson, L., Prograss towards achieving sex preselection in farm animals, USDA Agricultural Research Service, (1989).

Keeler, K.et al., Flow microfluorometric analysis of living spermatozoa stained with Hoechst 33342, J. Reprod.Fert. 68:205-212 (1983).

Keij, J.et al., High speed Photodamage cell sorting: An evaluation of the Zapper Prototype, Methods in cell Biology vol. 42, (1994).

Kirchhoff, C.et al., The Molecular biology of the sperm surface:Post-Testicular Membrane Remodelling, The Fate of the Male Germ Cell, (1997).

Krueger, C.et al.,Low dose Insemination in synchronized gilts, Theriogenology 52: 13631373 (1999).

Landetie,J.,Induction and survival of micronuclei in rat spermatids. Comparison of two meiotic micronucleus techniques using cyclophosphamide, Mutation Research, 203:47-53 (1988).

Laser Innovations—Applications, http://www.laserinnovations.com/488nm.htm Feb. 2, 2004.

Libbus, B.et al.,Incidence of chromosome aberrations in mammalian sperm stained with Hoechst 33342 and UV-laser irradiated during flow sorting, Mutation Research, 182: 265-274 (1987).

Loken, M., Separation of viable T and B lymphocytes using a cytochemical stain, Hoechst 33342, The Journal of Histochemistry and Cytochemistry,vol. 28, No. 1, pp. 36-39 (1980).

Lucas, J.et al., Orientation measurments of microsphere doublets and metaphase chromosomes in flow, Cytometry 7:575-581 (1986).

Luttmer, S.et al.,Examination of living and fixed gametes and early embryos stained with supravital fluorochromes (Hoechst 33342 and 3,3'-dihexyloxacarocyanine Iodide), Gamete Research 15:267-283 (1986).

Masaki, J.et al., Effect of bull seminal plasma on the membrane characteristics of boarepididymal spermatozoa.

Maxwell, W.et al.,Physiology of spermatozoa at high dilution rates:The influence of seminal plasma, Theriogenology 52: 1353-1362 (1999).

Mazur, P., The role of Intracellular freezing in the death of cells cooled at supraoptimal rates, Cryobiology 14:251-272 (1977).

McSweeney,K.et al., Abstract: Insemination of lactating holstein cows with sexed frozen/thawed sperm, http://www.cvmbs.colostate.edu/physio/abstract/ges12.html Mar. 16, 2004.

Medeiros,C. et al., Current status of sperm cryopreservation: Why isn't it better? Theriogenology 57: 327-344 (2002).

Meistrich, M., Potential and limitations of physical methods for separation of sperm bearing an X- or Y- chromosome.

Meistrich, M.et al., "Cytogenetic" studies of spermatids of mice carrying Cattanach's translocation by flow cytometry, Chromosoma 74:141-151 (1979).

Morrell, J. et al., Offspring from inseminations with mammalian sperm stained with Hoechst 33342, either with or without flow cytometry, Mutation Research 224:177-183 (1989).

Morrell et al.,"Sexing of Sperm by Flow Cytometry", The Veterinary Record, 1988, pp. 322-324.

Morrier, A.et al., Glycerol addition and conservation of fresh and crypreserved ram spermatozoa, Canadian Journal of AnimalScience, Sep. 2002http://pubs.nrc-cnrc.gc.ca/aic-journals/2002ab/cjas02/sep02/clas01-045.html.

Moruzzi, J., Selecting a mammalian species for the separationof X- and Y- chromosome-bearing spermatozoa, J. Reprod. Fert. 57:319-323 (1979).

Murthi S. et al., Improved data acquisition system for digital flow cytometry, (2002).

Studt, T., MEMS-based Cell Sorter Speeds Clinical Studies, R& D Magazine, Dec. 2003: pp. 36-37 as currently presented on and printed from http;//www.rdmag.com 2 pgs.

Gwo-Bin, L.et al., Multi-cell-line micro flow cytometers with buried SU-8/SOG Optical waveguides, Feb. 2002.

Shapiro, H. M. et al., Multistation Multparameter Flow Cytometry: Some Influences of Instrumental Factors on System Performance, 1983,pp. 11-19,4,Allan R. Liss, Inc.

OcanaQuero, J.et al., Biological effects of helium-neon irradiation on acrosome reaction in bull, Scisearch Journal of Photochemistry and Photobiology, vol. 40 No. 3, pp. 294-298 (1997).

Pangawkar, G. et al., Physical and biochemical characteristics of semen in relation to fertility of Holstein-Friesian bulls, Indian vet. Med.J. vol. 13: 21-26 (1989).

Papa, S. et al., Chromatin organization in Isolated nuclei: Flow cytometric characterization employing forward and perpendicular light scatter, Cell Biochemistry and Function vol. 6: 31-38 (1988).

Parks, J. et al., Lipids of plasma membrane and outer acrosomal membrane from bovine spermatozoa, Biology of Reproduction 37:1249-1258 (1987).

Parks, J. Processing and handling bull semen for artificial insemination—Don't add insult to injury!, Department of Animal Science Cornell University.

Partec, Taking flow cytometry to the next generation, Catalogue 2001-2002.

Perez-Pe, R.et al., Semen plasma proteins prevent cold shock membrane damage to ram spermatozoa, Theriogenology 56 (3) : 425-434, Aug. 1, 2001, PMID: 11516122 http://www.ncbi.nlm.nih.gov/entrez/query.fcgi?CMD=search&DB=pubmed.

Peter, A. et al., Fractionation of bovine spermatozoa for sex selection: A rapid immunomagnetic technique to remove spermatozoa that contain the H-Y antigen, Theriogenology 40:1177-1185 (1993).

Petersen, Timothy W., et al, Stability of the Breakoff Point in a High-Speed Cell Sorter The Journal of the international society for Analytical Cytology, vol. 56A No. 2, Dec. 2003.

Pinkel Dan, Flow Cytometry and Sorting Analytical Chemistry, Mar. 1982 vol. 54 No. 3.

Pinkel Dan, Cytometric Analysis of Mammalian Sperm for Induced Morphologic and DNA Content Errors; Biological Dosimetry (Cytometric Approaches to Mammalian Systems) 1984.

Pinkel, D. et al; Radiation-Induced DNA Content Variability in Mouse Sperm. Radiation Research An International Journal, vol. 95, No. 3, Sep. 1983.

Piumi, F. et al., Specific cytogenetic labeling of bovine spermatozoa bearing X or Y chromosomes using florescent in situ hybridization (Fish), Genet, Sel. vol. 33: 89-98 (2001).

Polge, C., Low-temperature storage of mammalian spermatozoa, Unit of Reproductive Physiology and Biochemistry, Cambridge. Edited by Bell-Prince, C., NFCR Newsletter, http://www.ls.lanl.gov/NFCR/newsletter-Oc98/oct98.html Jan. 6, 2004.

Rasul, Z.et al., Changes in motion characteristics, plasma membrane integrity, and acrosome morphology during cryopreservation of buffalo spermatozoa, Journal of Andrology, vol. 22 No. 2, Mar. 4, 2001.

Rees, William A., et al,Betaine Can Eliminate the Base Pair Composition Dependence of DNA Melting; Biochemistry 1993, 32, pp. 137-144.

Rens, W.et al.,An X-Y paint set and sperm FISH protocol that can be used for validation of cattle sperm separation procedures, Journals of Reproduction and Fertility, 121: 541-546 (2001).

Reyes-Mereno, C.et al., Characterization of Secretory Proteins from cultured Cauda Epididymal Cells that significantly sustain bovine sperm motility, Molecular Reproduction and Development 63: 500-509 (2002).

Rippel,N. et al., Transcervical insemination: Effects of variation in total sperm number/dose on fertility, 83rd Annual Fall Conference for Veterinarians, Oct. 2002.

Rizzo, W. et al.,Liposome-mediated transfer of simian virus 40 DNA and minichromosome into mammalian cells, J. Gen. Virol 64:911-919 (1983).

Ruch, F., Determination of DNA content by microfluorometry, Introduction to Quanitative Cytochemistry, pp. 281-294 (1966).

Saacke, R.et al., Semen Quality test and their relationship to fertility, 4th National Association of Animal Breeders, (1972).

Salisbury, G.W.,et al."Preservation of Bovine Spermatozoa in Yolk-Citrate Diluent and Field Results from its Use", Journal of Dairy Science, 1941, vol. 24(11),pp. 905-910.

Schroter, S.et al., The glycocalyx of the sperm surface, Human Reproduction Update: vol. 5, No. 4, pp. 302-313 (1999).

Schuster, T. et al., Isolation of motile spermatozoa from semen samples using microfluidics, Reproductive BioMedicine Online,vol. 7 No. 1 75-81,www.rbmonline.com/Article/847, Apr. 16, 2003.

Seidel, George E. Jr. "What about sexed semen?" Hoard's Dairyman, The National Dairy Farm Magazine, May 10, 2001.

Sexing Technologies, Welcome to sexing Technologies, http://www.sexingtechnologies.com/ Dec. 11, 2003.

Shapiro, Howard M. M.D.,Building Flow Cytometers Chapter 9. Practical Flow Cytometry, second edition, Property of Washington University Medical Library.

Sharpe, J. et al., Radially symmetric excitation and collection optics for flow cytometric sorting of aspherical cells, Cytometry, 29:363-370 (1997).

Shapiro, H., Re: cheap laser idea??, http://www.cyto.purdue.edu/hmarchiv/1998/1015.htm Feb. 3, 2004.

Smith, P.et al., Characteristics of a Novel Deep Red/ Infrared Fluorescent Cell-Permeant DNA Probe, DRAQ5, in Intact human Cells Analyzed by Flow Cytometry, Confocal and Multiphoton Microscopy, Cytometry 40:280-291 (2000).

Stanger, J.et al., The Relationship between motility and the FITC-BSA binding Properties of Mouse epididymal spermatozoa, The Journal of Experimental Zoology 227: 323-327 (1983).

Stanic,P. et al.,Comparison of protective media and freezing techniques for cryopreservation of human semen, http://www.ncbi.nlm.nih.gov/entrez/query.fcgi?CMD=search&DB=pubmed , Jul. 11, 2000.

Stewart,R., Georgia Beef Challenge, Livestock Newsletter Jan.-Feb. 2002.

Takacs, T.et al.,Flow Cytometric determination of the sperm cell number in diluted bull semen samples by DNA staining method, Acta Biochim.Biophys.Hung. vol. 22 No. 1, pp. 45-57 (1987).

Thurston,L. et al., Identification of Amplified restriction fragment length polymorphism markers linked to genes controlling boar sperm viability following cryopreservation, Biology of Reproduction 66: 545-554 (2002).

Tone,S.et al., A method of vital staining of mouse eggs using Hoechst dye, Department of Developmential Biology (1986).

Tubman,L.et al., Abstract:Normality of calves resulting from sexed sperm, http://www.cvmbs.colostate.edu/bms/abstract/ges12.html Mar. 16, 2004.

Tucker,K.et al., Sperm separation techniques:Comparison of gradient products, Proceedings 2ed International workshop for Embryologists: Troubleshooting activities in the ART lab. (2002).

Van Dilla, M.et al., Measurement of Mammalian Sperm Deoxyribonucleic acid by Flow Cytometry, The journal of Histochemistry and Cytochemistry vol. 25 No. 7 pp. 763-773 (1977).

Vazquez, J.et al., Nonsurgical Uterotubal Insemination in the Mare, Reproduction: Mare vol. 44 (1998).

Vishwanath,R.et al., Storage of bovine semen in liquid and frozen state, Animal Reproduction Science 62: 23-53 (2000).

Washburn, S., Sex-Sorted Semen; Still several steps short of sensational, http://www.cals.ncsu.edu/an sci/extention/animal/news/apri196/april1965.html Mar. 16, 2004.

Welch,G.et al., Sex preselection: Laboratory Validation of the sperm sex ratio of Flow sorted X- andY- sperm by sort reanal ysis for DNa, Theriogenology 52:1343-1352 (1999).

Welch, G.et al., Fluidic and optical modification to a facs IV for flow sorting of X&Y Chromosomes bearing sperm based on DNA, International Society for Analytical Cytology (1994).

Wiltshire, M.et al., A Novel Deep Red/ Low infrared fluorescent flow cytometric probe DRAQ5NO, For the Discrimination of intact nucleated cells in apoptotic cell populations, Cytometry 39: 217-223 (2000).

Woelders, H. et al., Effects of Trehalose and Sucrose, Osmolality oh the freezing medium, and cooling Rate on Viability and intactness of bull sperm after freezing and thawing, Cryobiology 35: 93-105 (1997).

Wolf, D., Lipid domains in sperm plasma membranes, Molecular Membrane Biology 12: 101-104 (1995).

Wolf, D.et al., Changes in sperm plasma membrane lipid diffusibility after hyperactivation during In vitro capacitation in the mouse, The Journal of Cell Biology, vol. 102: 1372-1377(1986).

Wolf, D.et al., Diffusion and regionalization in membranes of maturing ram spermatozoa,The Journal of Cell Biology, vol. 98:1678-1684 (1984).

XY Files, Issue 1 Jun. 1999.

XY, Inc. , Sex selection Procedure, http://www.xyinc.com/sex select.html, Feb. 21, 2003.

XY Files, Issue 4 Aug. 2000.

XY Files, Issue 2 Oct. 1999.

XY Files, Issue 3 Mar. 2000.

XY Files, Issue 5 Mar. 2001.

XY Files, Issue 6 Mar. 2002.

Lindsey, A. C., et al., Hysteroscopic inseminatin of mares with low numbers of nonsorted or flow sorted spermatozoa; Equine vet. J. (2002) 34(2) 128-132.

European Application No. 00980567.9; Response to Appeal in Opposition T 1199/08-3301 00 980 267.9—2103/1 257 168—Cryopreserving Sperm Cells, filed by Hiltrud Breyer, MEP, Feb. 26, 2009.

Parallel U.S. Appl. No. 11/608,039, Office Action dated Jan. 27, 2009.

Parallel CA Application No. 2391370, Notice of Allowance dated Mar. 10, 2009.

Parallel AU Application No. 2005203165; Letters patent dated Feb. 12, 2009.

METHOD OF CRYOPRESERVING SELECTED SPERM CELLS

CROSS-REFERENCE TO RELATED APPLICATIONS

This application is a continuation of U.S. patent application Ser. No. 10/266,562, filed Oct. 7, 2002, which is a continuation of U.S. patent application Ser. No. 09/577,246, filed May 24, 2000, which is a divisional of U.S. patent application Ser. No. 09/478,299 filed Jan. 5, 2000 which claims the benefit of U.S. Provisional Application No. 60/167,423, filed Nov. 24, 1999, each hereby incorporated by reference herein.

FIELD OF THE INVENTION

The invention relates to a method for freezing sperm selected for a particular characteristic, as well as to a frozen selected sperm sample and methods of using such a sample. The invention is particularly useful for preserving sex-selected sperm.

BACKGROUND OF THE INVENTION

Over half a century ago, artificial insemination was introduced in the United States as a commercial breeding tool for a variety of mammalian species. Although artificial insemination was initially limited to regions relatively close to the site of sperm collection, advances in the cryopreservation and storage of sperm have facilitated widespread distribution and commercialization of sperm intended for artificial insemination or in vitro fertilization.

Further improvements in mammalian sperm collection, selection, cryopreservation, storage, and handling techniques have enhanced the ability of breeders to produce animals having desired traits. For example, advances in selection of mammalian sperm based on slight differences in physical characteristics has made it possible to separate sperm based on sex-type, that is, to select for cells containing either the X or Y chromosome. This technique allows the breeder to manipulate the relative percentage of X- or Y-type sperm in a sample and thereby determine offspring sex. The ability to select sperm based on sex-type or any other desirable characteristic provides an important tool for accelerating genetic progress, increasing production efficiency, and achieving greater flexibility in livestock management. Full exploitation of this tool, however, depends on the ability to freeze and store selected sperm.

A variety of methods are available for selecting cells; however, the selection and subsequent processing of sperm presents unique challenges because sperm are incapable of DNA repair and because of sperm morphology. Each sperm has an acrosome overlying the head and a tail, which are important for fertility and which are relatively susceptible to physical injury. In addition, sperm fertility decreases with increasing time between collection and use. As most of the available selection methods involve physical stresses and take time, selected sperm are typically somewhat compromised compared to non-selected cells. Fertility may be further reduced if the selection technique involves significant dilution. It has been suggested that this "dilution effect" may be due to the loss of protective components in seminal plasma.

Flow cytometry is a particularly efficient selection method that has been employed for sorting sperm by sex-type. However, sorted sperm are subject to stresses beyond those normally encountered in standard artificial insemination or in vitro fertilization protocols. In particular, flow cytometry is time consuming, and, because of the physical constraints of flow cytometers, sperm must be diluted for sorting to levels that are not optimal for storage. (usually to on the order of $10^5$-$10^6$/ml). Furthermore, sorted sperm intended for artificial insemination must be concentrated so that conventional packaging and delivery equipment can be used. The need for a concentration step thus exposes already somewhat compromised sperm to additional physical stresses.

The freezing of sperm also invariably reduces fertility, motility, and/or viability, and, although techniques for freezing unselected sperm are well known, no technique for cryopreservation of selected sperm has been described.

SUMMARY OF THE INVENTION

The present invention provides a method of cryopreserving sperm that have been selected for a specific characteristic. The method is particularly useful for cryopreserving sperm selected by a method that results in dilution of the sperm, since the method provides for the isolation of sperm from a selected sperm sample, followed by addition of a final extender to the isolated sperm to produce a suspension having a desired concentration of sperm. In a preferred embodiment, the method is employed to freeze sex-selected sperm. Although the cryopreservation method of the invention can be used to freeze sperm selected by any number of selection methods, selection using flow cytometry is preferred.

The present invention also provides a frozen sperm sample that has been selected for a particular characteristic, such as sex-type. In preferred embodiments, the frozen sperm sample includes mammalian sperm, such as, for example, human, bovine, equine, porcine, ovine, elk, or bison sperm. Also within the scope of the invention is a container including a frozen sperm sample according to the invention.

The frozen selected sperm sample can be used in a variety of applications. In particular, the sample can be thawed and used for fertilization. Accordingly, the invention also includes a method of using the frozen selected sperm sample for artificial insemination or in vitro fertilization.

DETAILED DESCRIPTION OF THE INVENTION

The present invention allows cryopreservation of sperm that have been selected for a particular characteristic, facilitating storage and/or shipment of selected sperm samples to sites distant from the collection site. Thawing yields viable sperm that can be used in procedures such as artificial insemination ("AI") and in vitro fertilization ("IVF"). This result was surprising because of the well-documented fragility of sperm. Prior researchers had demonstrated that the stresses associated with various selection methods or with cryopreservation resulted in significant losses in fertility and/or viability. The present inventors have demonstrated, for the first time, that pregnancies can be achieved with sperm that have been selected and then frozen.

The invention represents an important advance in livestock management, where selection of sperm for use in such procedures can be used to increase the production of offspring having desirable traits. For example, selection to obtain sperm carrying either the X or the Y chromosome allows control over offspring sex, which is advantageous for producers of animals such as dairy or beef cattle. Sex selection also finds application in breeding valuable (e.g., show or race horses) or endangered animals. The ability to freeze selected sperm, which the invention provides, will enable widespread use of such selection methods to, e.g., increase livestock production efficiency as well as quality.

Definitions

The term "acrosome" or "acrosomal cap" refers to the cap that covers the anterior half of the head of sperm and that contains enzymes necessary for ovum penetration.

The term "sex-type" refers to the type of sex chromosome present in the sperm (i.e., the X or Y chromosome).

The term "capacitation" refers to the specific changes a sperm undergoes to develop the capacity to fertilize ova, such as enzymic changes on the surface of the acrosome that lead to release of acrosomal enzymes that facilitate penetration of the sperm into the ovum.

As used with reference to sperm, the term "cryoprotectant" refers to a molecule that protects sperm during a freeze-thaw cycle, promoting survival and retention of fertilizing capacity.

The term "dilution effect" refers to the rapid decline in motility and/or viability of sperm when highly diluted.

As used herein, the term "selection" refers to a method whereby a sample is subdivided based on presence or absence of a specific characteristic (unless context dictates otherwise). Thus, a "selected sperm sample" is a sample obtained by subjecting a source sample to selection for the specific characteristic. A selected sperm sample is therefore enriched, relative to the source sample, in sperm having the specific characteristic.

The term "sorting" is used herein to describe a selection method carried out using a fluorescence-activated cell sorter (FACS).

The term "extender" refers to any medium that tends to preserve sperm viability.

The term "extension" refers to the dilution of sperm with extender.

The term "initial extender" refers to a medium used to extend sperm prior to the isolation step of the method of this invention.

The term "final extender" refers to a medium used to extend sperm prior to the freezing step of the method of this invention.

An "organic substance" in an extender described herein is any organic substance that tends to reduce cold shock and preserve fertility of sperm.

An "energy source" in an extender described herein is any substance or substrate that sperm can utilize for cell maintenance and/or motility.

The term "osmolality," as used herein, is a measure of the osmotic pressure of dissolved solute particles in a an aqueous solution (e.g., an extender). The solute particles include both ions and non-ionized molecules. Osmolality is expressed as the concentration of osmotically active particles (i.e., osmoles) dissolved in 1 kg of water.

Cryopreservation Method

The invention provides a method of cryopreserving selected sperm includes the following steps:
(1) obtaining a selected sperm sample;
(2) cooling the selected sperm sample;
(3) isolating sperm from the selected sperm sample;
(4) adding final extender to the isolated sperm to produce a suspension of sperm; and
(5) freezing the suspension of sperm.

Obtaining a Selected Sperm Sample

The first step in the cryopreservation method of the invention encompasses obtaining a previously selected sperm sample, as well as subjecting a source sample to any suitable selection method. Sperm from any species can be selected and frozen according to the method of the invention. The method can be carried out with sperm from domesticated animals, especially livestock, as well as with sperm from wild animals (e.g., endangered species). Preferably, the selected sperm sample contains mammalian sperm. Human sperm, bovine, equine, porcine, ovine, elk, and bison sperm are particularly preferred.

Generally, the selected sperm sample contains normal, viable sperm. To this end, the ejaculate from which the sperm are obtained typically has at least about 50%, and preferably at least about 75% morphologically normal sperm. In these embodiments, generally at least about 40%, and preferably at least about 60% of the sperm in the ejaculate exhibit progressive motility.

A wide variety of methods for selecting cells from a mixed populations are available, including, for example, selection based on binding of cells or cell components with antibodies, antibody fragments, or other binding partners and differential staining.

The invention is exemplified herein with selection based on sex-type, and sex-selected sperm for use in the invention can be obtained using any selection strategy that takes advantage of slight differences in characteristics between X- and Y-type sperm. Exemplary sex-selection methods include magnetic techniques (see, e.g., U.S. Pat. No. 4,276,139), columnar techniques (see, e.g., U.S. Pat. No. 5,514,537) gravimetric techniques (see, e.g., U.S. Pat. No. 3,894,529, reissue Pat. No. 32,350, U.S. Pat. Nos. 4,092,229, 4,067,965, and 4,155,831). Sex-selection based on differences in electrical properties is disclosed in U.S. Pat. No. 4,083,957, and techniques that select based on differences in electrical and gravimetric properties are discussed in U.S. Pat. Nos. 4,225,405, 4,698,142. and 4,749,458. U.S. Pat. Nos. 4,009,260 and 4,339,434 describe selection based on differences in motility. Biochemical techniques relying on antibodies are disclosed in U.S. Pat. Nos. 4,511,661, 4,999,283, 3,687,806, 4,191,749, 4,448,767, whereas U.S. Pat. Nos. 5,021,244, 5,346,990, 5,439,362, and 5,660,997 describe selection based on differences in membrane proteins.

Flow cytometry is a preferred method for separating cells from mixed populations based on differential staining with fluorescent dyes or binding to fluorescently labeled molecules, such as antibodies or nucleic acids. In fluorescence activated cell sorting ("FACS"), cells are "sorted" into different populations based on the fluorescence intensity upon irradiation. FACS can be used for sex-selection of sperm because the X chromosome contains slightly more DNA than the Y chromosome. When sperm are stained with a fluorescent DNA-binding dye, X-chromosome bearing sperm absorb more dye than Y chromosome bearing sperm and the two populations can therefore can be separated by FACS. This strategy was discussed in U.S. Pat. No. 4,362,246 and significantly expanded upon in U.S. Pat. No. 5,135,759 (issued to Johnson). Separation has been enhanced through-the use of high-speed flow cytometers, such as the MoFlo® flow cytometer produced by Cytomation, Inc. (Ft. Collins, Colo.) and described in U.S. Pat. Nos. 5,150,313, 5,602,039, 5,602,349, and 5,643,796, as well as in PCT Publication No. WO 96/12171.

The selection method used to obtain the selected sperm sample is preferably one that preserves sperm viability. Because of the relative fragility of sperm, normal flow cytometry techniques should generally be modified for sorting sperm. More specifically, the flow cytometry entails staining, dilution, and interrogation of cells with light. All of these steps represent stresses that can reduce sperm viability. The sensitivity of sperm to these stresses can vary between species and even between individuals within species. Such sensitivities have either been documented or can readily be determined by empirical studies, such as those described in Examples 1-5.

Modifications that enhance viability are described the patent publications discussed above. For instance, procedures that provide improved sheath and collector systems for sorting sperm are disclosed in PCT Publication No. WO 99/33956 (Application No. PCT/US98/27909). Further, Examples 1-7 below describe exemplary procedures for staining and sorting sperm. Example 3 describes a study of the effects of laser intensity and dye concentration of post-thaw motility of sorted frozen sperm. This study indicates that the use of lower laser intensities during sorting can increase post-thaw motility.

The selected sperm sample can contain a variety of components besides sperm and will often contain components added to protect the sperm during the selection process. In the case of FACS, the selected sperm sample can contain component(s) of the solutions used for staining and sorting (e.g., the sheath fluid and the catch buffer).

In addition, the selected sperm sample typically contains an extender or extender fraction. For example, "two-step" extenders including an "A fraction" lacking glycerol and a "B fraction" containing glycerol are well known. The A fraction is added to sperm first, followed by addition of an equal volume of the B fraction. For this step, the B fraction is often divided into at least two aliquots and added sequentially; e.g., the second B fraction aliquot is added 15 minutes after the first.

If no extender components are present, an extender or extender fraction is typically added to the selected sperm sample before the sperm are isolated from the sample. If only some extender components are present, additional components can optionally be added so that selected sperm sample includes a complete extender or an extender fraction before the isolation step. In exemplary embodiments, bovine sperm are flow-sorted so as to produce a selected sperm sample including the A fraction of an extender (see Examples 2, 3, and 4). If desired, the B fraction can then be added to the selected sperm sample before the isolation step (see Example 5). The pre-isolation step extender (or extender fraction) is termed "the initial extender" to distinguish it from the "final extender" employed for the extension of isolated sperm before freezing. If the selected sperm sample was selected using FACS, the initial extender can be matched to the sheath fluid employed for sorting. Exemplary matched sheath fluids and extenders are described in detail in Example 4.

An extender suitable for use in the selected sperm sample includes a physiologically acceptable carrier. The physiologically acceptable carrier is typically aqueous, and, in preferred embodiments, includes deionized water. Suitable extenders commonly comprise one or more of the following additional components: a cryoprotectant, a component that maintains osmolality and buffers pH, an organic substance that prevents cold shock and preserves fertility of sperm, a detergent that acts synergistically with certain organic substances to enhance preservation of sperm, an energy source that can be readily utilized by sperm, an antioxidant, which protects sperm from cold shock, a substance that facilitates sperm capacitation, and one or more antibiotics.

Although cryoprotectants useful in the invention are not limited to those acting by a particular mechanism, most conventional cryoprotectants act, at least in part, by reducing intracellular dehydration. Specifically, freezing is accompanied by an increase in solute concentration in the medium surrounding sperm. This increase in solute concentration draws water out of the cells, which increases intracellular electrolyte concentration. Exemplary cryoprotectants include glycerol, dimethyl sulfoxide, ethylene glycol, propylene glycol, and the like. The cryoprotectant suitable for use in a given extender can vary, depending on the species from which sperm are derived. For example, glycerol is suitable for use in cryopreservation of human and bovine sperm, but is generally not used for cryopreservation of porcine or rabbit sperm. Such preferences are well known for many commercially valuable sperm and can readily be determined empirically for other types of sperm.

The extender useful in the invention optionally includes one or more components that help maintain osmolality and provide buffering capacity. In preferred embodiments of the invention, the osmolality of the extender approximates that of physiological fluids. More preferably, the osmolality of the extender is in the range of about 280 mOsm to about 320 mOsm. The pH is also preferably within a physiologically acceptable range, more preferably in the range of about 6.5 to about 7.5.

Substances helpful in maintaining osmolality and pH within these ranges are well known in the art and can be added to the extender as a solid or already in solution. A buffer containing a salt, a carbohydrate, or a combination thereof can be employed for this purpose. Specific examples include sodium citrate, Tris[hydroxymethyl]aminomethane, and TES (N-Tris [Hydroxymethyl]methyl-2-aminoethanesulfonic acid), and monosodium. glutamate buffers; milk; HEPES-buffered medium; and any combination thereof. The component employed to help maintain osmolality and provide buffering capacity in a particular application can vary depending on the other components of the extender and, in some cases, on the species from which the sperm are derived. The selection of such a component for use in the present invention is, however, within the level of skill in the art.

One or more organic substances that protect sperm against cold shock and help preserve fertilizing capacity can also be included in the extender. Such substances are well known and are sometimes described as "nonpenetrating cryoprotectants." One skilled in the art can readily determine an organic substance suitable for a particular application of the cryopreservation method described herein. For example, organic substances containing protective constituents (e.g., lipoproteins, phospholipids, lecithin) that are believed to reduce the impact of cold shock and the dilution effect can be included in the extender. Suitable organic substances include disaccharides, trisaccharides, and any combination thereof. Exemplary organic substances include egg yolk, an egg yolk extract, milk, a milk extract, casein, albumin, lecithin, cholesterol, and any combination thereof The extender can also include a detergent. Alkyl ionic detergents, such as sodium dodecyl sulfate (SDS), have been reported to act synergistically with egg yolk to enhance protection against cold shock. Other detergents useful in the cryopreservation of cells can also be employed in the extender, and the selection of a particular detergent for a specific application is within the level of skill in the art in light of the guidance provided herein. See, e.g., Example 5.

Preferably, the extender includes an energy source that is readily utilized by sperm. In the absence of an energy source, sperm may oxidize intracellular phospholipids and other cellular components. Thus, the inclusion of an energy source in the extender protects intracellular reserves and cellular components. As is well known in the art, sugars, particularly monosaccharides, provide a convenient energy source, although any conventional energy source can be employed in the extender. Exemplary monosaccharides useful in the extender include glucose, fructose, and/or mannose.

One or more antioxidants can optionally be included in the extender to provide additional protection against cold shock. Exemplary antioxidants include butylated hydroxytoluene (BHT), its derivatives, and the like. However, other antioxidants useful in the cryopreservation of cells can also be employed in the extender, and the selection of a particular antioxidant for a specific application is within the level of skill in the art in light of the guidance provided herein.

The extender can also contain a substance that facilitates sperm capacitation. A variety of capacitation facilitators are known in the art and any can be employed in the extender. Examples include enzymes such as alpha amylase, beta amylase, beta glucuronidase, which can be used in combination, if desired.

Finally, the extender preferably includes an antibiotic, since substantial bacterial growth can threaten sperm viability and increase the risk of infection of the host in artificial insemination or in vitro fertilization procedures. Any of a variety of antibiotics useful in the cryopreservation of cells can also be employed in the extender. The selection of a suitable antibiotic depends on the species from which the sperm was obtained, the procedures involved in obtaining and handling the sperm sample, and the specific microorganism(s) to be targeted. Exemplary antibiotics include tylosin, gentamicin, lincomycin, spectinomycin, linco-spectin (a combination of lincomycin and spectinomycin), penicillin, streptomycin, and ticarcillin, which can be used alone or in combination. However, one skilled in the art can readily determine other antibiotics suitable for use in the extender.

Exemplary extenders are discussed in greater detail below and in the examples.

The sperm concentration is typically lower in the selected sperm sample than in the source sample, and, as indicated above, when FACS is employed, the dilution is significant. A typical sort based on sex-type can produce a sample containing sperm at $6 \times 10^5$ cells/ml catch buffer. As such a low concentration is not optimal for storage (at least for most species tested), the cryopreservation method of the invention generally concentrates the selected sperm sample.

Cooling the Selected Sperm Sample

The second step in the cryopreservation method entails cooling the selected sperm sample, typically, by reducing the temperature at a controlled rate. Cooling too rapidly can cause cold shock, which can result in a loss of membrane integrity and cell function. The severity of the effects of cold shock vary from species to species and depend on factors such as the rate of cooling and the temperature range. Under suitable controlled cooling conditions, the sperm are able to adapt to thermal effects. Example 2, among others, describes conditions for cooling bovine sperm, and determining suitable conditions for cooling sperm of other species is within the level of skill in the art.

In a preferred embodiment of the invention, the selected sperm sample is cooled typically from about 22° Celsius, to about 5 Celsius, and cooling is generally carried out over a period of about 60 minutes to about 24 hours, preferably over a period of about 90 minutes to about 240 minutes, and most preferably over a period of about 90 minutes to about 120 minutes. Cooling can be accomplished by any convenient method, including simply placing the selected sperm sample in a 5° Celsius environment.

Isolation of Sperm Cells from the Selected Sperm Sample

After initial extension of the selected sperm sample, sperm are isolated from the sample using any sufficiently gentle isolation method that provides at least about 50% recovery of sperm, more preferably about 75% to about 90% recovery of sperm, and most preferably about 80% to about 90% recovery of sperm. During the isolation step, the cooled sperm should generally be kept cold, i.e., between about 1 and about 8° Celsius, and preferably close to 4 or 5° Celsius.

Any of a variety of methods suitable for recovering cells from a suspension can be used to isolate the sperm, including for example, filtration, sedimentation, and centrifugation. In an exemplary, preferred embodiment, the selected sperm sample is aliquoted into 50 ml tubes at volumes not exceeding about 27 ml, and preferably between about 20 to about 27 ml. Centrifugation is carried out at about 4° Celsius, at about 850×g, for about 20 minutes. Preferably, the centrifugation step provides at least about 50% to about 90% recovery of sperm, more preferably about 60% to about 90% recovery of sperm, and most preferably about 70% to about 90% recovery of sperm. After isolation, the supernatant is removed and the pellet is suspended by vortexing gently or repeated aspiration at 4° Celsius. The sperm concentration is then typically determined (e.g., using a hemacytometer).

Final Extension of Isolated Sperm Cells

After isolation, the sperm are pooled, if desired, and extended with final extender to an appropriate concentration for freezing. The concentration of sperm after the final extension and prior to freezing is preferably in the range of about $1 \times 10^6$/ml to about $300 \times 10^6$/ml, more preferably about $10 \times 10^6$/ml to about $50 \times 10^6$/ml, and most preferably about $10 \times 10^6$/ml to about $20 \times 10^6$/ml.

The description of the initial extender above also applies to the final extender, which can be the same as or different from the initial extender. In particular embodiments, the composition of the sperm sample extended with the final extender is substantially similar to (if not the same as) the composition of the sperm sample after addition of the initial extender.

In a preferred embodiment of the invention, an egg yolk-Tris extender is used. After the addition of the extender, the sperm suspension comprises glycerol (cryoprotectant); citric acid and Tris[hydroxymethyl]aminomethane (buffer); egg yolk (organic substance); fructose (energy source); tylosin, gentamicin, and linco-spectin (antibiotics). The typical approximate concentrations of these components after addition of the final extender to the isolated sperm are:

| Components of Egg Yolk-Tris Extender | |
|---|---|
| Glycerol: | 4-8% vol/vol |
| Citric Acid: | 55-75 mM |
| Tris [hydroxymethyl]aminomethane: | 190-210 mM |
| Egg yolk: | 5-25% vol/vol |
| Fructose: | 45-65 mM |
| Tylosin: | 25-100 µg/ml |
| Gentamicin: | 200-300 µg/ml |
| Linco-spectin: | 100-400 µg/ml* |

*100-400 µg/ml lincomycin and 100-400 µg/ml spectinomycin

In a variation of this embodiment particularly suitable for freezing bovine sperm, the concentrations of these components after addition of the final extender to the isolated sperm are about 6% (vol/vol) glycerol, about 65 mM citric acid, about 200 mM Tris[hydroxymethyl]aminomethane, about 20% (vol/vol) egg yolk, about 56 mM fructose, about 50 µg/ml tylosin, about 250 µg/ml gentamicin, and about 150/

300 µg/ml linco-spectin (i.e., 150 µg/ml lincomycin and 300 µg/ml spectinomycin), in deionized water.

In an alternative embodiment, an egg yolk-citrate extender is employed. After the addition of the extender, the sperm suspension comprises glycerol (cryoprotectant); sodium citrate (buffer); egg yolk (organic substance); tylosin, gentamicin, and linco-spectin (antibiotics). The typical approximate concentrations of these components after addition of the final extender to the isolated sperm are:

| Components of Egg Yolk-Citrate Extender | |
|---|---|
| Glycerol: | 4-8% vol/vol |
| Sodium Citrate: | 60-80 mM |
| Egg yolk: | 5-25% vol/vol |
| Tylosin: | 25-100 µg/ml |
| Gentamicin: | 200-300 µg/ml |
| Linco-spectin: | 100-400 µg/mL* |

*100-400 µg/ml lincomycin and 100-400 µg/ml spectinomycin

Exemplary, preferred concentrations for freezing bovine sperm are about 7% (vol/vol) glycerol, about 72 mM sodium citrate, about 20% (vol/vol) egg yolk, about 50 µg/ml tylosin, about 250 µg/ml gentamicin, and about 250/300 µg/ml linco-spectin.

In another alternative embodiment, an egg yolk-TES-Tris ("EY TEST") extender is employed. After the addition of the extender, the sperm suspension comprises glycerol (cryoprotectant); egg yolk and heated milk, e.g., homogenized milk containing 1.25% fructose with 10% glycerol (organic substances); tylosin, gentamicin, and linco-spectin (antibiotics). The typical approximate concentrations of these components after addition of the final extender to the isolated sperm are:

| Components of Egg Yolk TES-Tris Extender | |
|---|---|
| Glycerol: | 3-7% vol/vol |
| Tris [hydroxymethy-methyl]-2-aminoethanesulfonic acid: | 140-170 mM |
| Tris [hydroxymethyl]aminomethane; | 60-80 mM |
| Egg yolk: | 5-25% vol/vol |
| Fructose: | 5-12 mM |
| Tylosin: | 50-150 µg/ml |
| Gentamicin: | 400-600 µg/ml |
| Linco-spectin: | 200-700 µg/mL* |

*200-700 µg/ml lincomycin and 200-700 µg/ml spectinomycin

Exemplary, preferred concentrations for freezing bovine sperm are about 5% (vol/vol) glycerol, about 158 mM Tris [hydroxymethy-methyl]-2-aminoethanesulfonic acid, about 72 mM Tris[hydroxymethyl]aminomethane, about 20% (vol/vol) egg yolk, about 8 mM fructose, about 100 µg/mL tylosin, about 500 µg/ml gentamicin, and about 300/600 µg/ml linco-spectin.

In yet another alternative embodiment of the invention, a Milk extender is employed. After the addition of the extender, the sperm suspension comprises glycerol (cryoprotectant); heated homogenized milk (organic substance); fructose (energy source); and tylosin, gentamicin, and linco-spectin (antibiotics). The typical approximate concentrations of these components after addition of the final extender to the isolated sperm are:

| Components of Milk Extender | |
|---|---|
| Homogenized Milk | 90% (Vol/Vol) |
| Glycerol: | 3-7% (vol/vol) |
| Fructose: | 1.25% (wt/vol) |
| Tylosin: | 50 µg/ml |
| Gentamicin: | 250 µg/ml |
| Linco-spectin: | 250/300 µg/ml* |

*250-300 µg/ml lincomycin and 250-300 µg/ml spectinomycin

Exemplary preferred concentrations for freezing bovine sperm are about 90% milk, about 10% (vol/vol) glycerol, about 1.25% fructose (wt/vol?), about 50 µg/ml tylosin, about 250 µg/ml gentamicin, and about 250/300 µg/ml linco-spectin.

Other extenders standardly used to freeze sperm can also be employed as the final extender in freezing selected sperm. A variety of extenders optimized for use in freezing sperm from various species have been described, and many are commercially available. Freezing extenders for equine sperm typically consist of milk, egg yolk, various sugars, electrolytes and a cryoprotectant. Exemplary freezing extenders are described by Squires, E. L., et al., *Cooled and Frozen Stallion Semen Animal Reprod. and Biotechnology Laboratory*, Bulletin No. 69, Chapter 8, "Seminal Extenders" pp. 49-51 (July, 1999).

Equilibration and Freezing of Sperm

Extension of the sperm sample produces a suspension of sperm, which is then transferred into containers for freezing. If the sperm are intended for use in fertilization, the cells are conveniently aliquoted into individual doses sufficient to achieve fertilization. The required dose can vary substantially from one species to the next and is either well-known (e.g., for cattle and horses) or can readily be determined. In the case of sex-selected bovine sperm, convenient doses range from about $1.0 \times 10^6$ sperm to about $3.0 \times 10^6$ sperm.

Any suitable container can be employed for freezing, including, for example, an ampule, a vial, and a straw. Sperm intended for AI are typically frozen in straws (e.g., 0.25 ml or 0.50 ml straws) designed for use with an insemination gun. Preferably, a bolus of extender is drawn into the straw, followed, in sequence, by air, sperm, air, and extender, so that the sperm are flanked on either side by an air space, which separates the sperm from a bolus of extender at either end of the straw.

Prior to freezing, the sperm are generally allowed to equilibrate at about 5° C. Preferably, the sperm are allowed to equilibrate for a period in the range of about 1 hour to about 18 hours, more preferably between about 3 hours and about 18 hours, and most preferably between about 3 hours and about 6 hours (see Example 2). Following equilibration, any standard freezing method can be employed, provided the freezing rate is not too rapid (i.e., not in excess of about 0.5° C./minute). Preferably, the freezing rate is about 0.5° C./minute. In an exemplary, preferred embodiment, the sperm are placed in static liquid nitrogen vapor, and freezing is carried out in three distinct stages over a period of about 10 minutes. In the first stage of freezing, the sperm are cooled from about 5° C. to about −15° C. at a rate of about 40° C./minute to about 65° C./minute. In the second stage of freezing, the sperm are cooled from about −15° C. to about −60° C. at a rate of about 25° C./minute to about 35° C./minute. In the third stage, the sperm are plunged into liquid nitrogen at about −100° C.

Selected Sperm Samples

In addition to a freezing method, the invention provides a frozen sperm sample including sperm selected from a source sample for a particular characteristic. The sperm can be from any species, including any of those discussed above with reference to the freezing method. The invention encompasses frozen sperm selected for any characteristic by any suitable method, such as those described above. Preferred embodiments include frozen sex-selected human, bovine, equine, porcine, ovine, elk, or bison sperm. Sex-selection is preferably carried out using flow cytometry as described generally above.

Also within the scope of the invention is a container containing a frozen sperm sample according to the invention. The container can be formed from any material that does not react with the frozen sperm sample and can have any shape or other feature that facilitates use of the sample for the intended application. For samples intended for use in AI, for example, the container is conveniently a straw (e.g., 0.25 ml or 0.5 ml straw) designed for use with an insemination gun. The container is sealed in any manner suitable for preserving the sample at the intended storage temperature, which is typically below −80° Celsius. 0.25 ml straws can be sealed, for instance, with PVC powder, ultrasonically, or with a cotton-polyvinyl plug and/or a stainless steel ball (BB).

As the frozen sperm sample of the invention is typically thawed before use, the invention also provides a thawed, previously frozen, selected sperm sample and a container including such a thawed sample.

Methods of Using the Selected Sperm Sample

The frozen selected sperm sample of the invention is suitable for use in any method in which sperm are used. The sample can be thawed and used in any conventional fertilization method, such as artificial insemination or in vitro fertilization. Thawing is carried out in the same manner as for frozen, non-selected sperm. Briefly, the straw containing the frozen sperm is submerged in a water bath maintained at a temperature of about 35° C. to about 37° C. for a period of about 20 to about 30 seconds. After thawing, semen deposition (e.g., insemination) is carried out according to standard procedures, taking care to protect the sperm from environmental fluctuations.

EXAMPLES

Example 1

Effects of Dilution on Sperm

Objective: to determine the effect of sperm concentration on sperm motility for non-frozen, non-sorted, but highly diluted sperm.

A. Effects of Dilution on Non-washed Sperm

1. Collection of Source Sample. Sperm were collected from bulls on a routine collection schedule using an artificial vagina as described in Schenk J., Proc 17th NAAB, p. 48-58 (1998), and Saacke RG, Proc NAAB Tech Conf AI Reprod. 41:22-27 (1972). All ejaculates used contained greater than 50% progressively motile and greater than 75% morphologically normal sperm. Antibiotics were added to the raw ejaculate as described by Shin S., Proc NAAB Tech Conf AI Reprod. 11:33-38 (1986) within 15 minutes of collection, and the concentration of sperm was determined using a spectrophotometer.

2. Methods. Sperm from 4 bulls were diluted to 1.25, 2.5, 5, 10, 15, and $20 \times 10^6$/ml using an egg yolk-citrate extender (EYC) prepared with 20% egg yolk (vol/vol) in 72 mM sodium citrate, 50 μg/ml tylosin, 250 μg/ml gentamicin, and 250/300 μg/ml linco-spectin. Each sample was prepared in duplicate (2 tubes/dilution/bull) and comprised 8 ml total volume per tube. All samples were incubated for 60 minutes at 22° C., after which they were centrifuged using a swinging bucket centrifuge (Eppendorf, Model # 5810R) at 600×g for 10 minutes to concentrate the sperm. After centrifugation, the supernatant from one set of the duplicate tubes was not removed; the sperm were resuspended in the same medium and at the original concentration by repeated gentle aspiration using a 5-ml serological pipette. (The second set of the duplicate tubes were used in Example 1B.) Sperm samples were then cooled to 5° C. at 0.2° C./min over 90 minutes. These sperm were termed "non-washed sperm." All samples were incubated at 5° C. for 24 or 48 h post-collection.

3. Evaluation of Motility. After incubation, the samples were warmed to 37° C. using a dry block incubator for 10 minutes prior to determination of motility. For this experiment, a single, blind estimate of the percentage of progressively motile sperm was determined for each sample. Progressive sperm motility was determined subjectively for each subclass by a single observer (×200, phase-contrast microscopy); another person prepared the microscope slides in a randomized manner so the observer was unaware of treatments.

4. Statistical Analysis. Data were analyzed by analysis of variance (SAS Institute, Cary, N.C.) with factors bulls and initial dilution concentration. Separate analyses were done for each incubation time. Dilution trends were tested using (log) linear contrasts.

5. Results. Data for non-washed sperm (Table 1) revealed (log) linear relationships (P<0.01) for both incubation times. Percentages of motile sperm increased as sperm concentration increased from $1.25 \times 10^6$/ml to $10 \times 10^6$/ml, but there was little difference thereafter. The cubic term was significant (P<0.05) for 24-h and marginally significant (P<0.1) for 48-h incubations. There was a bull effect (P<0.01) at both times.

TABLE 1

Effects of cooling on non-washed sperm motility (%) after cooling to 5° C.

| Dilution | Incubation at 5° C. | |
|---|---|---|
| ($10^6$/ml) | 24 h[a] | 48 h[b] |
| 1.25 | 18[c] | 0[c] |
| 2.5 | 38[c,d] | 6[c,d] |
| 5.0 | 56[d] | 31[d,e] |
| 10.0 | 61[d] | 42[e] |
| 15.0 | 55[d] | 44[e] |
| 20.0 | 58[d] | 41[e] |
| S.E.[f] | 5.6 | 6.4 |

[a](log) linear (P < 0.01) and cubic effects (P < 0.05).
[b](log) linear (P < 0.01) and cubic effects (P < 0.1).
[c,d,e]Means within columns without common superscripts differ (P < 0.05).
[f]$\sqrt{\text{error mean square of ANOVA}} \div \sqrt{N}$ (SAS Institute, Cary, NC, USA)

B. Effects of Dilution on Washed Sperm

1. Collection of Source Sample. The second set of the duplicate tubes containing samples prepared in Example 1A were used in this experiment.

2. Methods. The sperm were diluted, incubated and concentrated by centrifugation as in Example 1A. Following centrifugation, 7.1 ml of the supernatant was aspirated from each tube, removing most of the seminal plasma and leaving the sperm in a 900-μl pellet. The sperm were diluted with EYC (see Example 1A) to make $10\times10^6$/ml or $20\times10^6$/ml sperm suspensions. The samples were then cooled to 5° C. over 90 minutes as in Example 1A.

3. Evaluation of Motility. The samples were warmed and evaluated for progressive motility as in Example 1A.

4. Statistical Analysis. Data were analyzed as in Example 1A. In addition, data in Example 1B were analyzed for incubation concentration at 5° C.

5. Results. Data for washed sperm (Table 2) revealed no significant treatment effects when sperm were evaluated after 24 h. However, after storage for 48 h at 5° C., there were bull, initial dilution, incubation concentration and bull by incubation effects (P<0.05). More sperm remained motile when held at $20\times10^6$/ml than at $10\times10^6$/ml (31% vs. 20%; P<0.05). Initial dilutions of 1.25, 2.5, and $5\times10^6$ sperm/ml resulted in lower progressive motility than $10\times10^6$ sperm/ml (P<0.05), with respective main effect means of 19, 20, 27, and 37% motile sperm.

TABLE 2

Cumulative effects of washing, dilution, concentration and cooling on progressive sperm motility (%)

| Sperm conc ($10^6$/ml) during 1 h preincubation at 37° C. | Storage at 5° C. - Sperm Concentration and Duration | | | |
|---|---|---|---|---|
| | 24 h | | 48 h[a] | |
| | $20\times10^6$/ml | $10\times10^6$/ml | $20\times10^6$/ml | $10\times10^6$/ml[b] |
| 1.25 | 45 | 49 | 24 | 15 |
| 2.5 | 51 | 40 | 29 | 11 |
| 5.0 | 54 | 54 | 32 | 21 |
| 10.0 | 51 | 50 | 40 | 34 |
| 15.0 | 60 | | 41 | |
| 20.0 | 55 | | 40 | |

[a]Concentration to $20\times10^6$ sperm/ml was superior (P < 0.05) to $10\times10^6$ sperm/ml after 48 h storage.
Also, initial dilution to $10\times10^6$ was superior to lower dilutions (P < 0.05).
Pooled standard errors ($\sqrt{\text{error mean square of ANOVA}} \div \sqrt{N}$) were 4.0 for 24 h, and 2.8 for 48 h incubations.
[b]Significant (log) linear trend (P < 0.06).

C. Conclusion

High sperm dilution and cooling resulted in a substantial reduction in the percentage of motile sperm, regardless of the presence or removal of seminal plasma. However, this dilution effect was greatly attenuated by concentrating the diluted sperm to $10\times10^6$/ml and even more, to $20\times10^6$/ml before storage at 5° C. Sperm from some bulls tolerated dilution better than sperm from other bulls; however, the bull differences found are typical. Extremely dilute sperm might be compromised during sorting, in part, by removal of protective compounds in seminal plasma.

Example 2

Effects of Equilibration Time Before Freezing Sorted Sperm

Objective: to evaluate the effect of equilibration times (3, 6 and 18 h, 5° C.) before freezing on flow-sorted sperm.

The following experiment was replicated in its entirety using the same bulls:

1. Collection of Source Sample. Sperm of 4 bulls were collected and prepared as described in Example 1A.

2. Methods.
   a) Staining and Preparation for Sort.
      i) Preparation of Stain Stock Solution: a stock solution of 8.89 mM Hoechst 33342 (bis-Benzimide H-33342; #190305, ICN Biomedicals Inc., Aurora, Ohio) was prepared in deionized water.
      ii) Sperm Stain Procedure: sperm were diluted in a modified TALP buffer (Table 3) to $400\times10^6$ sperm/ml. Following dilution, Hoechst 33342 dye was added to the sperm suspensions at a concentration of 224 μM. After the stain was added to the sperm suspensions, the samples were incubated for 60 minutes at 34° C. Following incubation, sperm were diluted to $100\times10^6$/ml with TALP containing 2.67% clarified egg yolk and 0.002% food coloring dye (FD& C #40) which quenches the fluorescence of Hoechst 33342 in sperm with compromised cell membranes, allowing them to be gated out during the sorting process. Just prior to flow sorting, samples were filtered at unit gravity through a 40-μm nylon mesh filter to remove any debris and/or clumped sperm.
   b) Sorting. A two-line argon laser operating at 351 and 364 nm and 150 mW was used to excite the Hoechst 33342 dye. The flow cytometer/cell sorter used was an SX MoFlo® (Cytomation, Inc., Fort Collins, Colo., USA) operating at 50 psi, A Tris-based sheath fluid was used, consisting of Tris (hydroxymethyl) aminomethane (Tris; 197.0 mM; #T-1503, Sigma Chemical Co., St. Louis, Mo., USA), citric acid monohydrate (55.4 mM; #C-7129, Sigma Chemical Co., St. Louis, Mo., USA) and fructose (47.5 mM; #F-0127, Sigma Chemical Co., St. Louis, Mo., USA). Baseline antibiotics were also added to the Tris-based sheath fluid consisting of 0.58 g/L of penicillin and 0.05 g/L of streptomycin sulfate.

The sperm were sorted by a process referred to as "bulk sorting" which permits rapid accumulation of large numbers of sperm so that large-scale examples can be done within a reasonable time. The sperm pass through the flow cytometer under the standard operating conditions with the exception that all droplets containing viable sperm were collected into a single tube rather than being sorted into 2 tubes based upon specific characteristics (e.g., sorting by sex-type). Sperm were sorted on the basis of viability; hence, sperm that have compromised plasma membranes were excluded during bulk sorting.

Stained sperm were maintained at 22±1° C. during sorting. Bulk sorted sperm were collected in 50-ml plastic tubes containing 2 ml of 20% egg yolk-Tris extender prepared with 20% egg yolk (vol/vol) in 200 mM Tris, 65 mM citric acid, 56 mM fructose, 50 μg/ml tylosin, 250 μg/ml gentamicin, and 150/300 μg/ml linco-spectin in deionized water. The egg yolk-Tris extender was termed "Tris-A fraction" to denote the lack of glycerol at this point in the procedure. Sperm were collected in tubes to contain 12 ml and approximately $6\times10^6$ sperm. The sperm were subsequently incubated at 22° C. for 1 to 3 h to simulate conditions of a sort based on sex-type.

c) Preparation for Freezing. Following incubation, the sorted sperm were cooled to 5° C. over the period of 70 minutes. After cooling, the contents of the two tubes were pooled and transferred to a refrigerated, swinging bucket centrifuge set at 5° C. and centrifuged at 850×g for 20 minutes. After removing the supernatant, processing continued at 5° C. by adding about 150 μl of Tris-A fraction extender to about 150-μl of sperm pellet to bring the sperm concentration to approximately $40\times10^6$/ml. The sperm of individual bulls were pooled and diluted immediately with an equal volume of egg yolk-Tris extender containing 12% (v/v) glycerol ("Tris-B fraction"). The Tris-B fraction was added to the sperm suspension as 2 equal volumes at 15-minute intervals to adjust the final sperm concentration to $20 \times 10^6$/ml. The final glycerol concentration of the complete egg yolk-Tris extender containing the sperm was 6% (v/v).

d) Equilibration and Freezing. Extended sperm were then packaged into 0.25-ml polyvinylchloride straws to be frozen by routine procedures on racks in static liquid nitrogen vapor. Two straws from each of 4 bulls were frozen after 3, 6 and 18 h of total equilibration time at 5° C.

3. Evaluation of Post-Thaw Motility. Straws were thawed in a 37° C. water bath for 30 sec. Blind estimates of progressive motility were made after incubating samples at 37° C. for 0, 1 and 2 h post-thawing. Each of two observers estimated progressive sperm motility from each of two straws of semen. These four blind estimates for each experimental unit represent subsampling.

4. Statistical Analysis. Statistically, the subsamples were analyzed as a subplot to the main plot least-squares ANOVAs to analyze effects of any observer and observer×treatment interaction. N refers to the number of experimental units, not subsamples; standard errors were calculated on the basis of means of the 4 subsamples from error mean squares of ANOVAs and the numbers of experimental units; least-squares means are presented.

Treatment effects were evaluated via separate ANOVAs for each incubation time. The model included bulls as a random effect and equilibration time and observer as fixed effects; the subplot consisted of the observer term and related interactions.

5. Results. The 3- or 6-h equilibration times were superior to 18-h (Table 4), based on the percentage of progressively motile sperm, for 0 and 1 h (P<0.01) but not 2 h of post-thaw incubation. Effects of bull were evident at 1 and 2 h incubation times (P<0.05), but not at 0 h. There was no significant (P>0.1) bull by equilibration time interaction nor was there a significant observer effect for any response.

TABLE 3

Modified TALP Buffer

| Ingredient | Concentration |
| --- | --- |
| NaCl | 95.0 mM |
| KCl | 3.0 mM |
| NaHPO$_4$ | 0.3 mM |
| NaHCO$_3$ | 10.0 mM |
| MgCl$_2$•6H$_2$O | 0.4 mM |
| Na Pyruvate | 2.0 mM |
| Glucose | 5.0 mM |
| Na lactate | 25.0 mM |
| HEPES[a] | 40.0 mM |
| Bovine serum albumin[b] | 3.0 mg/ml |
| Gentamycin Sulfate | 30.0 µg/ml |

[a]#H3375, Sigma Chemical Co., St. Louis, MO, USA
[b]#US70195, fraction V; Amersham/Life Science, Cleveland, OH, USA

TABLE 4

Effect of pre-freeze equilibration time on post-thaw progressive motility (%)

| Equilibration at 5° C. | Post-thaw incubation at 37° C. | | |
| --- | --- | --- | --- |
| | 0 h | 1 h | 2 h |
| 3 h | 41[a] | 36[a,b] | 16 |
| 6 h | 41[a] | 37[a] | 18 |
| 18 h | 35[b] | 31[b] | 12 |
| S.E.[c] | 1.5 | 0.8 | 2.0 |

[a,b]Within columns, means without common superscripts differ (P < 0.05), Tukey's HSD.
[c]Pooled standard errors, $\sqrt{\text{error mean square of ANOVA}} \div \sqrt{N}$ 6. Conclusion. The results indicated no differences in post-thaw sperm motility between 3 and 6 h of total equilibration time at 5° C., but there was a significant decline in sperm motility following 18 h of equilibration at 5° C. before freezing. The 3- to 6-h range permits pooling 2 consecutive 3-h sorting batches for freezing sperm without decreasing post-thaw motility.

As the bull by equilibration-time interaction was not significant, 3 to 6 h equilibration was adequate, with the caveat that only 4 bulls were used. The optimum equilibration time for a minority of bulls is expected to be >6 h.

Example 3

Effects of Stain Concentration and Laser Power on Sorted Sperm

Objective: to evaluate the effects of Hoechst 33342 dye concentration in combination with laser intensity on flow-sorted sperm.

1. Collection of Source Sample. Sperm of 6 bulls were collected and prepared as described in Example 1A.

2. Methods.
  a) Experimental Design. One ejaculate (2 bulls) and 2 ejaculates on different days (4 bulls) were used in a 2 by 2 design plus control.
  b) Staining and Sorting. Staining, preparation for sorting and sorting sperm were achieved as described in Example 2 except that the Hoechst 33342 dye was added to sperm suspensions at a final concentration of 149 µM or 224 µM; and sperm were bulked-sorted with the laser operating at 100 mW or 150 mW of incident power. Bulk-sorted sperm were collected into 50-ml plastic tubes as described in Example 2. Four tubes containing approximately $15 \times 10^6$ total sperm/tube were collected over 1 h for each bull. The sorted sperm were incubated for 1 h at 22° C. to simulate a longer sorting time.
  c) Preparation for Freezing. Following incubation, the sperm were cooled as in Example 2. The sperm were then concentrated by centrifugation at 5° C. at 850×g for 20 minutes. After removing the supernatant, 150 µl of Tris-A fraction extender was added to each 150-µl sperm pellet at 5° C. All of the sperm pellets were suspended by gentle repeated aspiration and the sperm of individual bulls were pooled. Tris B-fraction extender was added stepwise as described in Example 2. A non-stained, non-sorted control for each bull was prepared at $20 \times 10^6$ sperm/ml in Tris extender containing 6% glycerol and cooled to 5° C. while the bulk-sorted sperm were being prepared.
  d) Equilibration and Freezing. The control and sorted sperm were packaged into 0.25-ml polyvinylchloride straws as described in Example 2, equilibrated at 5° C. for 3 h and then frozen conventionally.

3. Evaluation of Post-Thaw Motility. Straws were thawed and evaluated as described in Example 2.

4. Statistical Analysis. A general description of statistical analyses is provided in Example 2. Specifically, treatment effects were evaluated via ANOVA. The model included dye concentration, laser intensity and bulls in the main plot, and observer and related interactions in the subplot. Bulls were considered a random effect and the other factors as fixed.

5. Results. Bull effects were significant for percentages of progressively motile sperm immediately after thawing ($P<0.1$) and after 1 h and 2 h of incubation at 37° C. ($P<0.05$). There was no effect of dye concentration or bull by dye concentration on sperm motility at any incubation time. With bulls considered as a random effect, 150 mW of laser power resulted in lower post-thaw motility of sperm than 100 mW at 0 h of incubation ($P<0.1$), but not at other incubation times (Table 5). If bulls are considered as fixed effects, 150 mW of power resulted in lower sperm motility than 100 mW ($P<0.05$) at all 3 incubation times. There was an effect of bull by laser power ($P<0.05$) on sperm motility at 1 h, but not at 0-h or 2-h incubation times. Also, the higher laser power resulted in lower sperm motility than the control ($P<0.05$) at 0- and 1-h incubation times (Table 5). There was a significant observer effect at 1-h, but not at 0-h or 2-h, incubation times. There was no observer by treatment interaction ($P>0.1$).

TABLE 5

Effects of laser intensity and dye concentration on post-thaw motility (%).

| Main effect means | Incubation at 37° C. | | |
|---|---|---|---|
| | 0 h | 1 h | 2 h |
| Control | 49 | 44 | 33 |
| Dye Concentration | | | |
| 149 μM | 41 | 39 | 30 |
| 224 μM | 42 | 39 | 30 |
| Laser Intensity | | | |
| 100 mW | 46 | 42 | 33 |
| 150 mW | 38[a] | 35[b] | 27 |
| S.E.[c] | 2.2 | 1.2 | 1.3 |

[a]Significant main effect ($P < 0.1$) and differs from control ($P < 0.05$).
[b]Differs from control ($P < 0.05$).
[c]Pooled standard errors, $\sqrt{\text{error mean square of ANOVA}} \div \sqrt{N}$ 6. Conclusion. Percentages of progressively motile sperm post-thaw were diminished by the staining and sorting process. Higher laser intensity was more damaging than the lower laser intensity. There was no effect of dye concentration on post-thaw sperm motility. Thus, excitation of the sperm-bound Hoechst 33342 dye at lower laser intensities is less damaging and that staining sperm at the higher dye concentration had no detrimental effect on post-thaw motility. The damage observed was presumably to the sperm-motility apparatus.

Example 4

Evaluation of Pre-Sort Staining Procedures and Selection of Extenders for the Cryopreservation of Sperm Objective: (1) to evaluate three pre-sort treatments for sperm; and, (2) and to evaluate sheath fluid and extender combinations for the cryopreservation of flow-sorted sperm.

The following experiment was replicated in its entirety:

1. Collection of Source Sample. Sperm from 4 bulls were collected and prepared as described in Example 1A.

2. Methods.
   a) Experimental Design. A 3 (pre-sort treatments) by 3 (extenders) by 2 (sheath fluids) by 4 (bulls) by 2 (observers) factorial experiment was designed to determine the best procedure to hold sperm prior to sorting, and to evaluate three extenders for cryopreserving the sorted sperm.
   b) Sample Preparation and Staining. Freshly collected sperm from each of 4 bulls were treated as follows:
      (1) diluted to $400\times10^6$/ml in modified TALP (see Example 2, Table 3) and stained for 1 h at 34° C. before bulk-sorting ("Dilute—0 h");
      (2) incubated neat at 22° C. for 3 h before dilution, staining and sorting ("Neat—3 h"); or,
      (3) diluted and stained as "Dilute-0 h and then incubated at 22° C. for 3 h before bulk-sorting ("Diluted—3 h").
   c) Extenders. The following freezing extenders were compared: EYC (see Example 1) containing 7% glycerol, egg yolk-Tris (see Example 2) containing 6% glycerol, and egg yolk-TES-Tris (TEST) containing 5% glycerol. EYC "A Fraction" refers to the EYC extender containing no glycerol, and EYC "B Fraction" refers to EYC extender containing twice the final, desired glycerol concentration (i.e., 14%). Thus, when EYC A and B fractions are combined in equal volume, the final EYC extender contains 7% glycerol. Tris A and B fractions are similarly named, and described in Example 2. TEST extender is prepared as a complete extender containing 5% glycerol; hence, there were no "A" and "B" fractions for TEST.
   d) Sheath Fluid. Sheath fluid was either 98.6 mM sodium citrate dihydrate (#S279-3, Fisher Scientific, Fair Lawn, N.J.) or Tris as described in Example 2. Both types of sheath fluid were adjusted to pH 6.8; osmolality was about 270 to 280 mOsm/kg. Tris sheath fluid was used to collect sperm that were later extended in egg yolk-Tris and TEST freezing extenders. Sheath fluid containing 98.6 mM sodium citrate dihydrate was used to collect sperm to later be extended in EYC freezing extender.
   e) Sorting. Approximately $58\times10^6$ sperm for each combination of pre-sort treatment, sheath fluid and extender were bulk-sorted as described in Example 2 using 150 mW of incident laser power. For each sort, sperm were collected over approximately 1 h. After sorting, the samples were incubated at 22° C. for 2 h to simulate a 3 h sort.
   f) Preparation for Freezing. Following incubation, the sperm were cooled as described in Example 2. After cooling, the samples were centrifuged at 5° C. at 850×g for 20 min. Each sample comprised about 28 ml total volume and was contained in a 50-ml plastic tube After the supernatant was removed, the sperm were returned to a 5° C. cold room for extension. Samples were extended to $40\times10^6$/ml by depositing 131 μl of the sperm suspension into 69 μl of A-fraction EYC, A-fraction egg yolk Tris, or TEST extender. Immediately, suspensions were adjusted to $20\times10^6$ sperm/ml with the addition of the matched glycerol containing extender (i.e., B-fraction EYC, B-fraction Tris) or TEST. B-fraction extenders were added to their respective samples stepwise (2×) at 15-min intervals as described in Example 2. The TEST was added to sperm stepwise in the same manner as B fraction EYC and Tris extenders.

g) Equilibration and Freezing. Sperm were packaged into 0.25-ml polyvinylchloride straws, equilibrated for 3 h at 5° C. and then frozen in static liquid nitrogen vapor.

3. Evaluation of Post-Thaw Motility. Thawing and post-thaw evaluations of sperm were done as described for Example 2.

4. Statistical Analysis. A general description of statistical analyses is provided in Example 2. Specifically, treatment effects were evaluated via separate analyses of variance for each post-thaw incubation time. The main plot included pre-sort treatment, extenders, and bulls; the subplot consisted of observers and associated interactions. Bulls were considered a random effect, and the other factors, fixed. The entire experiment was replicated twice. Tukey's HSD test was used to separate means.

5. Results. Post-thaw progressive motility of bulk-sorted sperm was affected (P<0.05) by extender and bulls at each post-thaw incubation time and by pre-sort procedure at 0 h of incubation (Table 6). There were no differences due to sheath fluids (P>0.05). At 0-h post-thaw incubation, use of the neat-3 h treatment resulted in more motile sperm after freezing and thawing than the other 2 pre-sort staining treatments (P<0.05; Table 6). However, pre-sort procedures were not statistically significant after post-thaw incubation of sperm for 1 or 2 h with bulls considered as a random effect. Importantly, at these 2 incubation times, there were significant pre-sort treatment by bull interactions (P<0.05). Furthermore, pre-sort treatment would have been a significant effect at all post-thaw incubation times had bulls been considered as fixed effects.

Immediately after thawing (0 h), TEST was the best extender, but after 1 or 2 h of incubation of 37° C., Tris was the best extender. Importantly, there was no pre-sort treatment by extender interaction for any response. There were observer effects (P<0.01) at all incubation times, but no observer by treatment interactions. There was a bull by extender interaction (P<0.05) at all 3 incubation times.

TABLE 6

Main effects of pre-sort treatment and freezing extenders on post-thaw progressive motility (%)

| | | Incubation at 37° C. | | |
|---|---|---|---|---|
| Pre-sort procedure | Extender | 0 h | 1 h | 2 h |
| Dilute - 0 h | Mean | 39$^a$ | 32 | 22 |
| Neat - 3 h | Mean | 43$^b$ | 36 | 25 |
| Dilute - 3 h | Mean | 38$^a$ | 31 | 19 |
| Mean | EYC | 36$^a$ | 29$^a$ | 17$^a$ |
| Mean | Tris | 40$^b$ | 39$^b$ | 29$^b$ |
| Mean | TEST | 44$^c$ | 33$^c$ | 20$^a$ |
| S.E.$^d$ | | 0.8 | 0.8 | 0.7 |

$^{a,b,c}$Means within columns, within main effects, without common superscripts differ (P < 0.05).
$^d$Pooled standard errors $\sqrt{\text{error mean square of ANOVA}} \div \sqrt{N}$ 6. Conclusion. This study showed that holding sperm neat for 3 h before dilution, staining and sorting was better than immediate dilution and staining 0 h or 3 h later. Thus, by 3 h into the sort, it is best to continue with a new aliquot of the original ejaculate that was held neat 3 h and then stained, rather than continuing with the original sample of sperm stained and held at $400 \times 10^6$ sperm/ml.

Even though TEST extender provided higher pott-thaw motility at 0 h, Tris was the superior extender when sperm were stressed by incubation at 37° C. Either sheath fluid worked equally well for each extender. Based on these results, we have incorporated the use of Tris sheath fluid in combination with Tris freezing extender into our standard operating procedure.

Example 5

Effects of Extender Additives on Sorted Sperm

Objective: to evaluate the effect of adding sodium dodecyl sulfate ("SDS") to the freezing extender on flow-sorted sperm.

A. Evaluation of Effect of Concentration of SDS in Freezing Extender

1. Collection of Source Sample. Sperm of 6 bulls were collected and prepared as described in Example 1A.

2. Methods. Sperm from each of 6 bulls were extended to $20 \times 10^6$/ml in 20% whole egg Tris ("WET") extender containing 0, 0.03, 0.06, 0.09, or 0.12 percent SDS, packaged into straws and frozen. WET extender was prepared using 3.028 g of Tris[hydroxymethyl]aminomethane, 1.78 g of citric acid monohydrate, and 1.25 g of fructose per 100 ml of double distilled water, to which 20% whole egg (vol/vol) was added. The WET extender was prepared at a pH of about 7.0 and contained a final glycerol concentration of about 6% (vol/vol). The WET extender also contained 1000 IU of penicillin "G" sodium and 100 μg of streptomycin sulfate/ml.

3. Results. The respective means (n=1 sample from each of 6 bulls) were 51, 51, 50, 51, and 48% progressive motile sperm approximately 10 minutes post-thaw. Based on these results, 0.06 percent SDS was used in Example 5B.

B. Evaluation of the Effects of 0.06 Percent SDS in Various Freezing Extenders on Post-Thaw Motility of Flow-Sorted Sperm 1. Collection of Source Sample. Sperm of 8 bulls were collected and prepared as described in Example 1A.

2. Methods. Post-thaw motility was studied for sperm frozen in egg yolk-Tris (see Example 2) and WET extenders (see Example 5A) with and without 0.06% SDS. Final glycerol content for both extenders was 6%.

a) Staining Preparation for Sort, Sorting. Stained sperm samples were prepared from an ejaculate from each of 8 bulls as described in Example 2. Stained sperm were bulked-sorted using Tris sheath fluid as described in Example 2 except that the sort was achieved using 135 mW of incident laser power. Sorted sperm were collected in a 50-ml plastic tube containing 2 ml of A-fraction freezing buffer for each extender; $15 \times 10^6$ total sorted sperm (25 ml) for each treatment were collected and incubated for 1 h at 22° C. to simulate longer sorting.

b) Preparation for Freezing. Diluted sperm were then cooled to 5° C. over minutes. An equal volume of appropriate B-fraction extender was added stepwise (2×) at 15-minute intervals to each 50-ml plastic tube containing sorted sperm. Aliquots, of 25 ml/extender treatment were concentrated by centrifugation for 20 minutes at 850×g in a refrigerated centrifuge. The supernatant was removed leaving a 600 μL sperm pellet, which was suspended by gentle vortexing for 15 seconds. No additional extender was added to the sperm pellet since the suspension containing the pellet already contained glycerol. The concentration of the sperm suspension was approximately $20 \times 10^6$/ml. A non-stained, non-sorted control for each bull was prepared at $20 \times 10^6$ sperm/ml in egg-yolk-Tris extender containing 6% glycerol. The control was placed in a 5° C. cold room while bulk-sorting occurred.

c) Equilibration and Freezing. All control and bulk-sorted sperm were packaged and frozen at the same time. Sperm were packaged into 0.25-ml polyvinylchloride straws, equilibrated for about 3 h to about 6 h at 5° C. and then frozen in static liquid nitrogen vapor.

3. Evaluation of Post-Thaw Motility. Thawing and post-thaw evaluations of sperm were done as described for Example 2 with the exception that progressive motility was evaluated 0.5 and 2.0 h after incubation.

4. Statistical Analysis. A general description of statistical analyses is provided in Example 2. Specifically, treatment effects were evaluated via separate analyses of variance for each incubation time; the model included bull and extender in the main plot and observer and related interactions in the subplot. Differences in means were determined by the least significant difference test.

5. Results. Extender affected (P<0.05) progressive motility of sperm after 0.5 or 2 h post-thaw incubation (Table 7). At 0.5 h, WET plus SDS resulted in lower motility than Tris with SDS. At 2 h, all treatments with bulk-sorted sperm were worse than the non-sorted control sperm. There were significant bull and observer effects (P<0.01) at both incubation times, but no observer by treatment interactions.

TABLE 7

Effect of extender on post-thaw progressive motility (%)

| Extender | Incubation at 37° C. | |
|---|---|---|
| | 0.5 h | 2 h |
| Tris (non-sort) | 42[a] | 41[a] |
| Tris w/o SDS | 40[a,b] | 35[b] |
| Tris w/SDS | 42[a] | 37[b] |
| WET w/o SDS | 40[a,b] | 35[b] |
| WET w/SDS | 38[b] | 35[b] |
| S.E.[c] | 1.0 | 1.2 |

[a,b]Means within columns without common superscripts differ (P < 0.05).
[c]√error mean square of ANOVA ÷ √N 6. Conclusion. The inclusion of SDS in Tris or WET extenders did not benefit sperm quality as determined by visual estimates of motility after thawing. Also, results using WET and Tris extenders were similar; hence, WET appeared as efficacious as Tris for cryopreserving sorted bovine sperm.

Example 6

Quality of Sperm Sexed by Flow Sorting for Field Trials

Objective: to evaluate post-thaw quality of sorted sperm based on acrosomal integrity.

1. Collection of Source Sample. Sperm of 3 bulls were collected and prepared as described in Example 1A.

2. Methods. Sorted and non-sorted control sperm from the same ejaculate were stained, processed, and sorted as described in Example 2 except the sperm were sorted for sex-type at a 90% purity level. Sorted sperm were collected to a volume of approximately 20 ml and were cooled to 5° C. for 90 minutes (0.2° C./min). After cooling, an equal volume of egg yolk-Tris B extender (see Example 2) was added to the sorted sperm in 2 equal volumes at 15-minute intervals. Centrifugation and aspiration of the supernatant were achieved as described in Example 5. After centrifugation and aspiration, egg yolk-Tris extender containing 6% glycerol (v/v) was added to the sperm pellet to bring the concentration of sperm to about $20 \times 10^6$/ml. Freezing and thawing were done as described in Example 2 except that equilibration time was about 3 h.

3. Evaluation of Post-Thaw Motility. Visual estimates of the percentage of progressively motile sperm at 37° C. were made approximately 10 minutes after thawing. The acrosomal integrity of sperm was assessed using differential interference-contrast microscopy (×1000) after 2 h of incubation at 37° C. Sperm were treated with 40 mM sodium fluoride, a wet was smear made, and 100 sperm per treatment were examined. Acrosomes were classified as: (a) intact acrosome, (b) swollen or damaged acrosome, or (c) missing acrosome (non-intact).

4. Statistical Analysis. The data analyzed were from 19 different freeze dates balanced across 3 bulls used in field trials. Treatment effects (sort vs. control) were evaluated via analysis of variance with bulls as a fixed effect.

5. Results. The percentage of progressively motile sperm post-thaw was significantly higher (P<0.05) for non-sorted sperm (50%) than for sorted sperm (46%; Table 8), despite removal of dead sperm during sorting. However, the percentage of sperm with an intact acrosome was not different. Sorting increased the percentage of sperm missing an acrosome, but also reduced the percentage of sperm with a damaged acrosome, relative to control sperm (P<0.05). There were significant differences among bulls for percent of intact acrosomes (P<0.05), percent of non-intact acrosomes (P<0.01), and post-thaw progressive motility (P<0.01). There was a bull by sorting effect for post-thaw motility (p<0.01) but not for the other responses. From bulls A and B, differences in post-thaw motility between sorted and unsorted sperm were near zero; for bull C, sorted sperm were 10 percentage points (19%) lower in motility than control sperm.

TABLE 8

Effect of sorting on post-thaw motility (%) and acrosomal status (%)

| | Acrosomal status | | | |
|---|---|---|---|---|
| | Intact | Damaged | Non-intact | Post-thaw motility |
| Control | 64[a] | 20[a] | 15[a] | 50[a] |
| Sorted | 65[a] | 14[b] | 21[b] | 46[b] |

[a,b]Column means with different superscripts differ (P < 0.05).

6. Conclusion. Visual estimates of progressive motility for sorted, frozen sperm on average were slightly lower (4 percentage points; 8%) than for control sperm, although this difference was larger for one bull. These evaluations were made approximately 10 minutes after thawing. The small average difference is consistent with that for non-intact acrosomes after 2 h of incubation. Sperm with a damaged or missing acrosome are likely to be immotile. The increased percentage of sperm with a non-intact acrosome, for sorted samples, indicates damage associated with sorting or with cryopreservation before or after actual sorting. Presumably, sorting converted damaged acrosomes to missing acrosomes. Based on standard procedures for evaluation of sperm quality, there is no basis for assuming that fertilizing potential of these flow-sorted sperm should be severely compromised for most bulls.

Example 7

Sex-Selection and Cryopreservation of Bull Sperm Using 20% Egg Yolk-Tris Extender Objective: to provide a protocol for the cryopreservation of flow-sorted bull sperm.

1. Collection and Ejaculate Assessment. Collect and prepare ejaculates as described in Example 1A. Select ejaculates from those bulls with >75% morphologically normal sperm. Visually estimate the percentage of progressively motile sperm (ejaculates that have progressive motility >60% are best for sorting). Add antibiotics to raw semen as follows: tylosin at a final concentration 100 μg/ml, gentamicin at a final concentration of 500 μg/ml, and linco-spectin at a final concentration of 300/600 μg/ml.

2. Staining and Preparation for Sort. Following the addition of the antibiotics to the raw semen sample, allow 15-20 minutes before staining. Stain samples as described in Example 2.

3. Sorting. Sort for both X— and Y— type sperm, setting the sorting gates for 90% purity. Sort sperm into 50-ml Falcon tubes containing 2 ml 20% egg yolk-Tris A-fraction extender (see Example 2) until each tube contains a maximum of 20 ml total volume (or a maximum of 2 h per sort) and final sorted sperm concentration is $6 \times 10^5$/ml. Note that additional 20% egg yolk-Tris-A fraction catch buffer must be added after the sort and prior to cooling so that the final percentage of egg yolk is at least 3%.

4. Preparation for Freezing. Following the sort, cool the sorted samples to 5° C. over a period of 90 minutes. After cooling, add 20% egg yolk-Tris B-fraction extender (see Example 2) stepwise (2x) at 15 minutes intervals. The final volume of Tris B-fraction extender added to the sperm sample should be equal to the volume of Tris A-fraction extender. The total volume of sperm sample after the Tris B-fraction extender is added should not exceed 27 ml total volume.

After the Tris B-fraction extender is added to the sperm sample, concentrate the sample by centrifugation for 20 minutes at 850×g. Aspirate the supernatant leaving approximately 150 μl sperm pellet. Resuspend the sperm and pool the sperm for each individual bull.

5. Freezing. Add complete egg yolk-Tris extender (6% glycerol) to achieve a final sperm concentration of $20 \times 10^6$/ml. Package the extended sperm into 0.25-ml polyvinylchloride straws for freezing as described in Example 2.

Example 8

Evaluation of the Fertility of Flow-Sorted, Frozen Bull Sperm in Field Studies

Materials and Methods

Semen Collection and Processing

Semen from young bulls of unknown fertility was collected via artificial vagina (see Example 1A). After determining sperm concentration with a spectrophotometer and subjective evaluation of progressive sperm motility, semen was processed and sorted as described in Example 2 except that the sperm were sorted by sex-type at 90% purity using a laser incident power of about 135 to about 150 mW. Processing and freezing was achieved as in Example 2 except that the equilibration time was about 3 h. Cornell Universal Extender (Seidel G E Jr., Theriogenology 1997; 48:1255-1264) was used for liquid semen in field trials 1, 2, and 3. For frozen semen in field trials 2 and 3, the extender used was 2.9% Na citrate+20% egg yolk with a final glycerol concentration of 7% (see Example 1). For field trials 4 through 11, sperm were frozen in a Tris-based extender composed of 200 mM Tris, 65 mM citric acid, 56 mM fructose, 20% egg yolk, and a final glycerol concentration of 6% (see Example 2). The sheath fluid used in the flow cytometer was 2.9% Na citrate (see Example 4) for trials 1, 2, and 3, and a Tris buffer for the remaining trials (see Example 2).

Sperm were packaged in 0.25-ml French straws in columns as small as 50 μl in the center of the straw. To minimize dilution effects, low volumes were used so there were at least $10^7$ sperm/ml. In most trials, a column of extender without sperm was aspirated into the straw first to wet the cotton plug, followed by a small column of air, and then the sexed sperm. When sperm were frozen, one straw from each batch was thawed in 35° C. water for 30 sec for quality control, and batches with less than 25% progressive motility post thaw were discarded. A sample of sexed sperm from each batch was sonicated and analyzed by flow cytometry to determine the accuracy of sexing.

Heifer Management and Artificial Insemination

The heifers used were in 6 widely scattered production units with different management practices. Seasonal and breed differences contributed further to the heterogeneity of the experiments (Table 9). Insofar as possible, treatments and controls were alternated systematically within bulls within inseminators as heifers entered the insemination facilities.

Estrus was synchronized in one of 4 ways (Table 9): (1) 500 mg of melengesterol acetate (MGA) fed daily in 2.3 kg of grain for 14 days followed by an i.m. injection of 25 mg prostaglandin $F_2\alpha$ (Lutalyse, Upjohn, Kalamazoo, Mich., USA) 17, 18 or 19 days after the last day of feeding MGA (MGA/PG); (2) a single injection of 25 mg of prostaglandin $F_2\alpha$ (PG); (3) 20 or 25 mg of prostaglandin $F_2U$ injected i.m. at 12-day intervals (PG/PG) or (4) 50 or μg of GnRH injected i.m., followed by 25 mg of prostaglandin $F_2\alpha$ 7 days later (GnRH/PG).

Heifers were inspected visually for standing estrus mornings and evenings, but inseminated only in the evenings after 16:00, approximately ½ or 1 day after onset of estrus. Insemination was either into the uterine body conventionally, or half into each uterine horn using atraumatic embryo transfer sheaths (IMV, Minneapolis, Minn., USA). In the latter case, semen was deposited past the greater curvature of the uterine horn as far anterior as could be accomplished without trauma, identically to nonsurgical embryo transfer. In most cases, semen was deposited between the anterior third and mid-cornua.

Most experiments included a frozen sperm control inseminated into the uterine body with 20 or $40 \times 10^6$ sperm/dose from the same bulls used for sperm sorted for sex-type ("sexed"). This control served as a composite estimate of the intrinsic, normal fertility of the heifers under the specific field-trial conditions as well as the fertility of the bulls used and the skills of the inseminators. Some trials also included a low-dose, unsexed control group. Sometimes numbers of control inseminations were planned to be ½ or ⅔ the number used for each treatment to obtain more information on sexed sperm. Frozen sexed and control sperm were thawed for 20 to 30 sec in a 35 to 37° C. water bath. Various other details are summarized in Table 9.

Pregnancy was diagnosed by ultrasound 28 to 37 d post insemination and/or 56 to 92 d post-insemination, at which time fetal sex was determined in most trials, as described in Curran, S., Theriogenology 1991; 36:809-814, without the operator's knowing insemination treatments of controls. Sexes of calves born were nearly identical to the fetal-sex diagnosis. Data were analyzed by single-degree-of-freedom Chi square corrected for continuity; 2-tail tests were used unless 1-tail is specified. Fewer than 5% of the inseminations were culled due to errors of insemination treatment, frank infection of the reproductive tract, failure to traverse the cervix, etc. Decisions to cull animals from experiments were made shortly after insemination and were never based on the pregnancy diagnosis.

differences in pregnancy rates between inseminators in any trial, but numbers of breedings per inseminator were low, and differences likely would be detected with larger numbers of inseminations.

Estrus synchronization methods were not compared within trials, so it was not possible to compare pregnancy rates among these methods. Pregnancy rates appeared to be satisfactory for all four synchronization procedures used.

Since inseminations were done once a day, heifers in estrus evenings were inseminated approximately 24 h after estrus was detected. The pregnancy rate for these heifers with sexed sperm pooled over all trials was 203/414 (49.0%), which was not significantly different (P>0.1) from that of heifers in estrus mornings and thus inseminated half a day after estrus

TABLE 9

Procedural details of field trials

| Trial | Insemination dates | Breeds of heifers | Bulls used | Inseminators | Estrus synchronization | Comments |
|---|---|---|---|---|---|---|
| 1 | 5/20-23, 1997 | Angus | N1, N2, AN4 | A, B | MGA/PG | Included low-dose controls |
| 2 | 2/18-5/22, 1998 | Angus crossbred | N3, N4, N5, N6 | C, D | PG/PG | Low dose but no normal-dose controls; some heifers pregnant and aborted when synchronized |
| 3 | 6/2-6/5, 1998 | Angus | AN4, AN5, N7, N8 | B, D | MGA/PG | |
| 4 | 2/10-13, 1999 | Holstein | J2, J4 | C, D | PG | Very severe mud, snow, wind, and cold, driving rain |
| 5 | 2/24-26, 1999 | Holstein | J2, J4, J5 | C, B, D | PG/PG | |
| 6 | 4/14-16, 1999 | Holstein | J2, J3, J4, J5 | C, D | PG | Some heifers were reproductive culls |
| 7 | 4/27-5/1, 1999 | Hereford & Angus crossbred | AN1, AN4 | C | MGA/PG | Semen for 1 bull shipped 6 h before sorting; severe weather |
| 8 | 4/21-5/1 1999 | Angus crossbred | H1, H2 | L | MGA/PG | Feedlot heifers |
| 9 | 5/5-8, 1999 | Red Angus | AR1, AR2 | C, F | MGA/PG | |
| 10 | 5/31-6/2 1999 | Angus | AN4, AN7, AN8 | B, D | GnRH/PG | |
| 11 | 7/28-30 1999 | Holstein | H2, H3 | C, D | PG/PG | First replicate available in a much larger trail |

Results and Discussion

The data presented are from 11 consecutive, heterogeneous field trials, constrained by logistical aspects of the studies, such as having to match bulls to genetic needs of the herds, unavailability of fertility information on bulls, limited numbers of heifers, unavailability of the same inseminators across trials, severe weather in some trials, limited amounts of sexed semen in early trials, 2 sets of heifers in which some turned out to be pregnant up to about 55 days at the time of estrus synchronization, etc. Up to 4 bulls and 3 inseminators were involved with each trial; this enabled us to sample populations to ensure that results applied to more than one bull or technician; however, insufficient data were produced to evaluate bull-to-bull differences in fertility rigorously.

Most sets of heifers were from breeding herds located 140 to 250 km from our laboratory. There were no significant detection 266/586 (45.4%). This tendency for higher fertility with later insemination is in agreement with findings from other research that it is preferable to inseminate later than normally recommended with lower fertility bulls, when low sperm numbers are used, or when conditions are otherwise suboptimal.

Pregnancy rates by treatments and, when available, fetal or calf sex are presented in Tables 10 to 20. The objective was to obtain female offspring, except in trial 8; accuracy was 95%, 83%, 90%, 83%, 82%, and 94% in Trials 1, 3, 8, 9, 10, and 11, respectively. In the remainder of the trials, fetal or birth sexes were not available because of timing of pregnancy diagnosis, unavailability of persons skilled in sexing fetuses, and/or because calves have not yet been born. This was not a major concern because the main objective of this research was to determine fertility of flow-sorted sperm inseminated at low doses.

The accuracy of sexing can be adjusted to virtually any level desired between 50 and 95+% by adjusting the sorting parameters. However, higher accuracy results in lower numbers of sperm sorted per unit time, particularly for Y-chromosome sperm. 90% accuracy is sufficient for routine work.

The main findings from each field trial will be summarized in turn. Note that total sperm numbers are given in table headings; numbers of progressively motile sperm usually were 30 to 50% of these values. Field trial 1 (Table 10) confirmed that pregnancy rates with uterine horn insemination using low numbers of unsexed sperm were similar to controls with normal sperm numbers. The day 64 to 67 pregnancy rate with unfrozen sexed sperm (42%) was 12 percentage points below the unsexed liquid control with sperm diluted, stained, and centrifuged identically to the sorted sperm. Accuracy of sexing was 95%; the sex of calves born from sexed sperm matched the sex diagnosis of fetuses exactly; there was one mistake in sexing fetuses of controls. There were no abortions between 2 months of gestation and term, and all 19 calves from the sexed sperm treatment were normal and survived. For the sexed semen treatment, the 2-month pregnancy rates for bulls N1, N2, and N3 were 41, 44, and 40%, respectively; 39% (13/33) of heifers in estrus in the morning and 50% (6/12) in estrus in the evening became pregnant.

between 2 months of gestation and term. Pregnancy rates averaged over sexed, unfrozen and sexed, frozen sperm for bulls N8, N9, AN5, and AN4 were 24, 31, 50, and 60%, respectively (P<0.1).

TABLE 12

Results of field trial 3 - Angus heifers in Wyoming, 1998

| Treatment/site | No. sperm | No. heifers | No. pregnant day 62 to 65 | No. ♀ calves |
|---|---|---|---|---|
| Sexed, 18° C./horns | $5 \times 10^5$ | 37 | 11 (30%)$^a$ | 10 (91%)$^c$ |
| Sexed, frozen/horns | $1 \times 10^6$ | 35 | 18 (51%)$^{a,b}$ | 14 (78%)$^c$ |
| Frozen, control/body | $40 \times 10^6$ | 37 | 27 (73%)$^b$ | 16 (59%)$^d$ |

$^{a,b}$Means without common superscripts differ (P < 0.05).
$^{c,d}$The percentage of ♀ calves from the sexed treatments (83%) differed from the control group, P > 0.05, 1-tail, $\chi^2$.

Field trials 4, 5, and 6 (Tables 13, 14, 15) were done at the same location with 3 different groups of heifers. Unfortunately, it was not possible to replicate each trial similarly due to vagaries of field trials, such as scheduling personnel, availability of sexed semen from each bull, etc. The widely different pregnancy rates between trials 5 and 6 illustrate that conditions were different among trials. Some of the heifers in trial 6 were available because they failed to get pregnant after

TABLE 10

Results of field trial 1 - Angus heifers in Wyoming, 1997

| Treatment/site | No. sperm | No. heifers | No. pregnant day 31 to 33 | No. pregnant day 64 to 67 | No. ♀ calves |
|---|---|---|---|---|---|
| Sexed, 5° C./horns | $3 \times 10^5$ | 45 | 20(44%) | 19(42%) | 18(95%)$^a$ |
| Control, 5° C./horns | $3 \times 10^5$ | 28 | 15(54%) | 15(54%) | 5(53%)$^b$ |
| Frozen control/body | $40 \times 10^6$ | 29 | 16(55%) | 15(52%) | 11(73%)$^{a,b}$ |

$^{a,b}$Sex ratios without common superscripts differ (P < 0.02).

Field trial 2 (Table 11) provided the first evidence that results with sexed, frozen sperm are similar to sexed, unfrozen sperm if adjustment is made for numbers of sperm killed during cryopreservation. There also was no difference in pregnancy rates between sexed sperm stored at 5 versus 18° C. Pregnancy rates at 2+months after insemination for sexed semen from individual bulls ranged from 22 to 42% pregnant (P>0.05). Embryonic loss between 1 and 2 months of gestation was very similar for sexed and control pregnancies. Calving data were available from 39 heifers from this trial; each of these heifers (30 sexed pregnancies, 9 controls) pregnant at 2 months calved after a normal-length gestation.

TABLE 11

Results of field trial 2 - Crossbred beef heifers in Colorado, 1998

| Treatment/site | No. sperm | No. heifers | No. pregnant day 30 to 35$^a$ | No. pregnant day 59 to 92$^a$ |
|---|---|---|---|---|
| Control, 5° C./horns | $5 \times 10^5$ | 58 | 27 (47%) | 24 (41%) |
| Sexed, 5° C./horns | $5 \times 10^5$ | 51 | 17 (33%) | 16 (31%) |
| Sexed, 18° C./horns | $5 \times 10^5$ | 46 | 16 (35%) | 12 (26%) |
| Sexed, frozen/horns | $1 \times 10^6$ | 87 | 29 (33%) | 28 (32%) |

$^a$No significant differences, $\chi^2$

Field trial 3 (Table 12) confirmed that sexed, frozen sperm results in reasonable pregnancy rates. The accuracy of sexing sperm was confirmed again; however, there were 4 errors in sexing fetuses relative to the calves born; the actual sexes of calves born are presented. Again, there were no abortions a month of natural mating. Under conditions of these trials, pregnancy rates were very similar between 1.5 and $3.0 \times 10^6$ sexed, frozen sperm/dose. Furthermore, there was no advantage to uterine-horn insemination. There were no significant differences (P>0.05) in pregnancy rates among bulls except in Trial 5 in which the pregnancy rate of J2, 20/28 (71%), was higher than that of J4, 15/39 (38%) (P<0.05). This difference was not consistent from trial to trial, as J4 had numerically but not significantly (P>0.1) higher pregnancy rates than J2 in Trials 4 and 6.

TABLE 13

Results of field trial 4 - Holstein heifers in Colorado, 1999

| Treatment/site | No. sperm | No. heifers | No. pregnant day 30 to 33 | No. pregnant day 64 to 67* |
|---|---|---|---|---|
| Sexed, frozen/body | $1.5 \times 10^6$ | 55 | 36 (65%)$^{a,b}$ | 36 (65%)$^{a,b}$ |
| Sexed, frozen/body | $3 \times 10^6$ | 52 | 27 (52%)$^a$ | 26 (50%)$^a$ |
| Control, frozen/body | $20 \times 10^6$ | 55 | 45 (82%)$^b$ | 43 (78%)$^b$ |

$^{a,b}$Means without common superscripts differ (P < 0.01).
*Six heifers pregnant at d 30 to 33 were sold before the second pregnancy diagnosis; these were assumed to have remained pregnant.

TABLE 14

Results of field trial 5 - Holstein heifers in Colorado, 1999

| Treatment/site | No. sperm | No. heifers | No. pregnant day 33 to 35[a] | No. pregnant day 60 to 62[a] |
|---|---|---|---|---|
| Sexed, frozen/body | $1.5 \times 10^6$ | 23 | 12 (52%) | 12 (52%) |
| Sexed, frozen/body | $3.0 \times 10^6$ | 25 | 15 (60%) | 14 (56%) |
| Sexed, frozen/horns | $1.5 \times 10^6$ | 25 | 15 (60%) | 12 (48%) |
| Sexed, frozen/horns | $3.0 \times 10^6$ | 25 | 17 (68%) | 15 (60%) |
| Control, frozen/body | $20 \times 10^6$ | 30 | 20 (67%) | 19 (63%) |

[a]No significant differences.

TABLE 15

Results of field trial 6 - Holstein heifers in Colorado, 1999

| Treatment/site | No. sperm | No. heifers | No. pregnant day 31 to 34 | No. pregnant day 60 to 63 |
|---|---|---|---|---|
| Sexed, frozen/body | $1.5 \times 10^6$ | 27 | 11 (41%)[a] | 9 (33%)[a] |
| Sexed, frozen/body | $3.0 \times 10^6$ | 25 | 10 (40%)[a] | 9 (36%)[a] |
| Sexed, frozen/horns | $1.5 \times 10^6$ | 24 | 8 (33%)[a] | 7 (29%)[a] |
| Sexed, frozen/horns | $3.0 \times 10^6$ | 24 | 10 (42%)[a] | 8 (33%)[a] |
| Control, frozen/body | $20 \times 10^6$ | 24 | 18 (75%)[b] | 17 (71%)[b] |

[a,b]Means without common superscripts differ (P < 0.05).

For trial 7 (Table 16), only one inseminator was available due to rescheduling. This is the only trial that showed a convincing advantage of uterine-horn over uterine-body insemination. For this inseminator under the conditions of the trial, 55% more heifers (22 percentage points) became pregnant with sexed, frozen semen inseminated into the uterine horns than into the uterine body. The true difference could be smaller because there are wide confidence intervals on these means. In all the other trials (5, 6, 9, and 11) in which body- and horn-insemination were compared, pregnancy rates were very similar for both methods for this technician as well as for other technicians.

Semen from one of the bulls used in Trial 7 was shipped without dilution from Montana by air in an insulated box at −20° C. before sorting; shipping time was 6 h. Pregnancy rates for the sexed sperm from the two bulls were virtually identical, 49% for the unshipped and 52% for the shipped semen. Semen was not diluted with extender and not cooled for shipping because staining properties of sperm with Hoechst 33342 are altered by dilution with extenders. Furthermore, in other studies (see Example 4), storing semen neat at ambient temperature between collection and flow-sorting was found to be superior to diluting it.

TABLE 16

Results of field trial 7 - Crossbred beef heifers in Colorado, 1999

| Treatment/site | No. sperm | No. heifers | No. pregnant day 33 to 37 |
|---|---|---|---|
| Sexed, frozen/body | $1.5 \times 10^6$ | 86 | 34 (40%)[a] |
| Sexed, frozen/horns | $1.5 \times 10^6$ | 86 | 53 (62%)[b] |
| Control, frozen/body | $20 \times 10^6$ | 35 | 18 (51%)[a,b] |

[a,b]Means without common superscripts differ (P < 0.01).

Field trial 8 (Table 17) concerned feedlot heifers not implanted with growth promotants; at the time pregnancy was diagnosed they were aborted, so calving data was not available. This experiment illustrates that efficacious sexing also can be done in the male direction. Pregnancy rates for the 2 bulls were 50 and 61%.

TABLE 17

Results of field trial 8 - Angus heifers in Nebraska, 1999

| Treatment/site | No. sperm | No. heifers | No. pregnant[a] day 74 to 76 | No. ♂ fetuses |
|---|---|---|---|---|
| Sexed, frozen 72 mW laser/body | $1 \times 10^6$ | 18 | 7 (39%) | 6 (86%) |
| Sexed, frozen, 135 mW laser/body | $1 \times 10^6$ | 18 | 13 (78%) | 12 (92%) |

[a]No significant differences.

Field trial 9 (Table 18) was the only trial to show a convincing advantage of 3.0 versus $1.5 \times 10^6$ sexed, frozen sperm/insemination dose. This advantage was true for both inseminators. Pregnancy rates for sexed sperm from the 2 bulls were 62 and 75%.

TABLE 18

Results of field trial 9 - Red Angus heifers in Nebraska, 1999

| Treatment/site | No. sperm | No. heifers | No. pregnant day 60 to 63[a] | No. ♀ fetuses |
|---|---|---|---|---|
| Sexed, frozen/body | $1.5 \times 10^6$ | 15 | 8 (53%) | 7 (88%) |
| Sexed, frozen/body | $3.0 \times 10^6$ | 14 | 12 (86%) | 9 (75%) |
| Sexed, frozen/horns | $1.5 \times 10^6$ | 16 | 9 (56%) | 7 (78%) |
| Sexed, frozen/horns | $3.0 \times 10^6$ | 16 | 12 (75%) | 11 (92%) |
| Control, frozen/body | $20 \times 10^6$ | 30 | 21 (70%) | 13 (62%) |

[a]$3.0 \times 10^6$ sexed sperm had a higher pregnancy rate (80%) than $1.5 \times 10^6$ sexed sperm (55%), P < 0.05, 1-tail $\chi^2$.

Pregnancy rates in field trial 10 (Table 19) with sexed, frozen semen, were similar to controls; the accuracy of sexing sperm on this trial was only 82%, which, however, is not significantly different from the targeted 90% accuracy. Pregnancy rates for sexed semen were 54, 66, and 50% for bulls AN4, AN7, and AN8, respectively (P>0.1). Eighteen of the heifers inseminated in this trial were the calves resulting from sexed sperm in field trial 1.

TABLE 19

Results of field trial 10 - Angus heifers in Wyoming, 1999

| Treatment/site | No. sperm | No. heifers | No. pregnant day 61 to 63[a] | No. ♀ fetuses |
|---|---|---|---|---|
| Sexed, frozen/body | $1 \times 10^6$ | 44 | 26 (59%) | 23 (85%) |
| Sexed, frozen/body | $3.0 \times 10^6$ | 43 | 23 (53%) | 17 (74%) |
| Control, frozen/body | $20 \times 10^6$ | 35 | 20 (57%) | 12 (57%) |

[a]No significant differences.

TABLE 20

Results of field trial 11 - Holstein heifers in Colorado, 1999

| Treatment/site | No. sperm | No. heifers | No. pregnant day 28 to 30[a] | No. pregnant day 56 to 58[a,b] |
|---|---|---|---|---|
| Sexed, frozen/body | $1 \times 10^6$ | 12 | 8 (67%) | 7 (58%) |
| Sexed, frozen/body | $3 \times 10^6$ | 12 | 6 (50%) | 4 (33%) |
| Sexed, frozen/horns | $1 \times 10^6$ | 7 | 4 (57%) | 4 (57%) |
| Sexed, frozen/horns | $3 \times 10^6$ | 7 | 4 (57%) | 4 (57%) |
| Control, frozen/body | $20 \times 10^6$ | 9 | 4 (44%) | 3 (33%) |

[a]No significant differences, $\chi^2$.
[b]16 of 17 (94%) fetuses from the sexed semen treatments were female; 2 were too deep in the body cavity to sex with ultrasound.

Data from trials were combined in which treatments were identical except 1×10 and 1.5×10⁶ sperm doses were pooled (Table 21).

TABLE 21

Meta-summary from combining trials with sexed, frozen semen and frozen controls.

| Trials combined | Sperm no./site | No. heifers | No. pregnant |
|---|---|---|---|
| 5, 6, 9, 11 | 1.0-1.5 × 10⁶/body | 77 | 36 (47%) |
|  | 3.0 × 10⁶/body | 76 | 38 (50%) |
|  | 1.0-1.5 × 10⁶/horns | 72 | 32 (44%) |
|  | 3.0 × 10⁶/horns | 72 | 39 (54%) |
|  | 20 × 10⁶/body, control | 93 | 61 (66%) |
| 4, 5, 6, 9, 10, 11 | 1.0-1.5 × 10⁶/body | 176 | 98 (56%) |
|  | 3.0 × 10⁶/body | 171 | 88 (51%) |
|  | 20 × 10⁶/body, control | 183 | 124 (68%) |
| 5, 6, 7, 9, 11 | 1.5 × 10⁶/body | 163 | 70 (43%) |
|  | 1.5 × 10⁶/horn | 158 | 85 (54%) |
|  | 20 × 10⁶/body, control | 128 | 79 (62%) |

Pregnancy rates with sexed sperm were generally 70-90% of unsexed controls within experiments with 7 to 20 times more sperm. This difference was less in the more recent trials, possibly reflecting improved sexing and sperm-processing procedures.

In some trials, heifers were examined for pregnancy by ultrasound at both 1 and 2 months after insemination. Pregnancy losses in this interval were similar ($P>0.1$) for sexed (23/261; 8.8%) versus control (9/145; 6.2%) sperm treatments, which is one measure that genetic damage due to sexing is minimal. Calving information was obtained from only a few of the pregnant heifers because most cattle from the earlier trials were sold, and those from later trials have not calved yet. The population of calves produced to date from sexed semen appears to be no different from the population of controls.

CONCLUSION

Sex ratios in cattle can be distorted to about 90% of either sex by sorting sperm on the basis of DNA content with a flow cytometer/cell sorter followed by cryopreservation and relatively routine artificial insemination. Calves resulting from sexed sperm appear to be normal. For most bulls in these studies, pregnancy rates with 1.0 to 1.5×10⁶ sexed, frozen sperm were 70 to 90% of unsexed controls with 20 or 40×10⁶ frozen sperm inseminated conventionally. These results apply to well-managed heifers bred by well-trained inseminators using properly processed semen. There may be a small advantage to inseminating sexed sperm bilaterally into the uterine horns compared to standard uterine body insemination.

The present invention has of necessity been discussed herein by reference to certain specific methods and materials. It is to be understood that the discussion of these specific methods and materials in no way constitutes any limitation on the scope of the, present invention, which extends to any and all alternative materials and methods suitable for accomplishing the ends of the present invention.

All patents and publications described are herein incorporated by reference in their entirety.

What is claimed is:

1. A method of freezing separated sperm cells, comprising the steps of:
   a. obtaining sperm cells from a male of a species of non-human mammal;
   b. differentiating said sperm cells based upon at least one property which allows a portion of said sperm cells to be identified as bearing either an X-chromosome or a Y-chromosome;
   c. separating said sperm cells into a discrete population based upon said at least one property;
   d. establishing from said discrete population a selected sperm sample having a sufficient number of sperm cells to fertilize an egg of a female of said species of non-human mammal;
   e. freezing said selected sperm sample.

2. A method of freezing separated sperm cells as described in claim 1 wherein said step of differentiating said sperm cells based upon a property which allows a portion of said sperm cells to be identified as either an X chromosome bearing sperm cell or a Y chromosome bearing sperm cell comprises assessing the amount of DNA within each sperm cell.

3. A method of freezing separated sperm cells as described in claim 2 further comprising the step of staining said sperm cells a fluorochrome which binds to DNA within said sperm cells.

4. A method of freezing separated sperm cells as described in claim 3 wherein said step of assessing the amount of DNA within each sperm cell comprises the steps of:
   a. exciting said fluorochrome which binds to DNA within said sperm cells; and
   b. analyzing light emitted by said fluorochrome bound to DNA within said sperm cells.

5. A method of freezing separated sperm cells as described in claim 1 wherein said step of separating said sperm cells having at least one desired sperm cell characteristic into a discrete population, further comprises:
   a. entraining sperm cells within a fluid stream;
   b. oscillating said fluid stream to generate droplets containing one of said sperm cells;
   c. charging each of said droplets based upon said at least one property differentiated; and
   d. deflecting said droplets based upon droplet charge.

6. A method of freezing separated sperm cells as described in claim 1 further comprising the step of removing fluid suspending said discrete population of sperm cells.

7. A method of freezing separated sperm cells as described in claim 6 further comprising the step of equilibrating said discrete population of sperm cells in a final extender.

8. A method of freezing separated sperm cells as described in claim 7 wherein said step of equilibrating said discrete population of sperm cells in a final extender has a duration of not less than about 3 hours and not more than about 6 hours.

9. A method of freezing separated sperm cells as described in claim 7 wherein said final extender comprises egg-yolk-Tris containing about 6% glycerol.

10. A method of freezing separated sperm cells as described in claim 7 wherein said final extender comprises egg-yolk-TES-Tris containing about 5% glycerol.

11. A method of freezing separated sperm cells as described in claim 7 wherein said final extender comprises a cold shock treatment, an energy source, an antibiotic, and a cryoprotectant.

12. A method of freezing separated sperm cells as described in claim 11 wherein said energy source is selected from the group consisting of a saccharide, a glucose, a fructose, a 56 mM fructose, a 45 mM to 60 mM fructose, a mannose, and any combination thereof.

13. A method of freezing separated sperm cells as described in claim 11 wherein said antibiotic is selected from the group consisting of tylosin, gentamicin, lincomycin, linco-spectin, spectinomycin, penicillin, streptomycin, and any combination thereof.

14. A method of freezing separated sperm cells as described in claim 11 wherein said cryoprotectant is selected from the group consisting of a disaccharide, a trisaccharide, and any combination thereof.

15. A method of freezing separated sperm cells as described in claim 11 wherein said cryoprotectant is selected from the group consisting of glycerol, 6% glycerol, between 5% to 7% glycerol, dimethyl sulfoxide, ethylene glycol, propylene glycol, and any combination thereof.

16. A method of freezing separated sperm cells as described in claim 7 wherein said final extender comprises a mixture of sodium citrate, egg yolk, glycerol, and at least one antibiotic.

17. A method of freezing separated sperm cells as described in claim 16 wherein said mixture further comprises fructose.

18. A method of freezing separated sperm cells as described in claim 16 wherein said mixture further comprises milk.

19. A method of freezing separated sperm cells as described in claim 16 wherein said mixture further comprises Tris [hydroxymehtyl]aminomethane.

20. A method of freezing separated sperm cells as described in claim 16 wherein said mixture further comprises Tris[hydroxymehtyl]-2-aminoethanesulfonic acid.

21. A method of freezing separated sperm cells as described in claim 7 wherein said final extender further comprises a component which maintains osmolality and buffers pH.

22. A method of freezing separated sperm cells as described in claim 21 wherein said component which maintains osmolality and buffers pH is selected from the group consisting of a buffer comprising a salt, a buffer containing a carbohydrate, and any combination thereof.

23. A method of freezing separated sperm cells as described in claim 21 wherein said component which maintains osmolality and buffers pH is selected from the group consisting of sodiumcitrate, Tris[hydroxymethyl]aminomethane, 200 mM Tris [hydroxymethyl]aminomethane, 175 mM to 225 mM Tris[hydroxymethyl]aminomethane, 200 mM Tris[hydroxymethyl]aminomethane/65 mM citric acid monohydrate, 175 mM to 225 mM Tris[hydroxymethyl]aminomethane/50 mM to 70 mM citric acid monohydrate, N-Tris [hydroxymethyl]methyl-2-aminoethanesulfonic acid, 200 mM Tris[hydroxymethyl]methyl1-2-aminoethanesulfonic acid, 175 mM to 225 mM Tris[hydroxymethyl]methyl-2-aminoethanesulfonic acid, 200 mM Tris[hydroxymethyl]methyl-2-aminoethanesulfonic acid/65 mM citric acid monohydrate, 175 mM to 225 mM Tris[hydroxymethyl]methyl1-2-aminoethanesulfonic acid/50 mM to 70 mM citric acid monohydrate, monosodium glutamate, milk, HEPES buffered medium, and any combination thereof.

24. A method of freezing separated sperm cells as described in claim 11 wherein said cold shock treatment is selected from the group consisting of egg yolk, 20% egg yolk, 15% to 25% egg yolk, an egg yolk extract, milk, a milk extract, casein, albumin, lecithin, and any combination thereof.

25. A method of freezing separated sperm cells as described in claim 1 wherein said step of freezing said discrete population of sperm cells having at least one desired sperm cell characteristic comprises establishing an insemination sample having a sufficient number of sperm cells to inseminate a female of said species of mammal and to fertilize at least one egg.

26. A method of freezing separated sperm cells as described in claim 25 wherein said discrete population of sperm cells having at least one desired sperm cell characteristic comprises sex-selected sperm cells.

27. A method of freezing separated sperm cells as described in claim 26 wherein said insemination sample contains between about one million and about three million sex-selected sperm cells.

28. A method of freezing separated sperm cells as described in claim 1 wherein said sperm cells are bovine sperm cells.

29. A method of freezing separated sperm cells as described in claims 1 wherein said sperm cells are equine sperm cells.

30. A method of freezing separated sperm cells as described in claim 1 wherein said sperm cells are porcine sperm cells.

31. A frozen separated cell sample in accordance with the method of claim 1.

32. A method of freezing separated sperm cells as described in claim 1 wherein said step of separating said sperm cells having at least one desired sperm cell characteristic into said discrete population comprises the step of separating said sperm cells by a separation method selected from a group consisting of flow cytometry and fluorescence-activated cell sorting.

33. A method of freezing separated sperm cells as described in claim 1 and further comprising the step of cooling said sperm cells.

34. A method of freezing separated sperm cells as described in claim 33 wherein said step of cooling said sperm cells comprises the step of reducing the temperature of said sperm cells to about 5° Celsius.

* * * * *